US007972823B2

(12) United States Patent
Fukui et al.

(10) Patent No.: US 7,972,823 B2
(45) Date of Patent: Jul. 5, 2011

(54) SUCCINIC ACID-PRODUCING BACTERIUM AND PROCESS FOR PRODUCING SUCCINIC ACID

(75) Inventors: Keita Fukui, Kawasaki (JP); Jun Nakamura, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1076 days.

(21) Appl. No.: 11/561,011

(22) Filed: Nov. 17, 2006

(65) Prior Publication Data

US 2008/0293112 A1    Nov. 27, 2008

Related U.S. Application Data

(63) Continuation of application No. PCT/JP2005/009232, filed on May 20, 2005.

(30) Foreign Application Priority Data

May 20, 2004    (JP) ................. 2004-150658

(51) Int. Cl.
    C12P 7/46    (2006.01)
    C12N 9/14    (2006.01)
    C12N 15/55   (2006.01)
(52) U.S. Cl. ................... 435/145; 435/195; 536/23.2
(58) Field of Classification Search ................... None
    See application file for complete search history.

(56) References Cited

U.S. PATENT DOCUMENTS

| | | | |
|---|---|---|---|
| 4,489,160 A | 12/1984 | Katsumata et al. |
| 4,500,640 A | 2/1985 | Katsumata et al. |
| 4,514,502 A | 4/1985 | Miwa et al. |
| 4,617,267 A | 10/1986 | Katsumata et al. |
| 5,034,105 A | 7/1991 | Berglund et al. |
| 5,132,456 A | 7/1992 | King et al. |
| 5,142,834 A | 9/1992 | Laclave et al. |
| 5,143,833 A | 9/1992 | Datta |
| 5,143,834 A | 9/1992 | Glassner et al. |
| 5,168,055 A | 12/1992 | Datta et al. |
| 5,185,262 A | 2/1993 | Kohama et al. |
| 5,504,004 A | 4/1996 | Guettler et al. |
| 5,770,435 A | 6/1998 | Donnelly et al. |
| 5,827,700 A | 10/1998 | Felman et al. |
| 5,869,301 A | 2/1999 | Nghiem et al. |
| 5,958,744 A | 9/1999 | Berglund et al. |
| 5,977,331 A | 11/1999 | Asakura et al. |
| 6,265,190 B1 | 7/2001 | Yedur et al. |
| 6,448,061 B1 | 9/2002 | Pan et al. |
| 6,455,284 B1 | 9/2002 | Gokarn et al. |
| 6,696,561 B1 | 2/2004 | Pompejus et al. |
| 2002/0055152 A1 | 5/2002 | Farwick et al. |
| 2002/0150999 A1 | 10/2002 | Dusch et al. |
| 2002/0197605 A1 | 12/2002 | Nakagawa et al. |
| 2003/0017559 A1 | 1/2003 | Donnelly et al. |
| 2003/0069354 A1 | 4/2003 | Oyasato et al. |
| 2003/0087381 A1 | 5/2003 | Gokarn et al. |
| 2003/0100079 A1 | 5/2003 | Mockel et al. |
| 2005/0196848 A1 | 9/2005 | Dusch et al. |
| 2006/0046288 A1 | 3/2006 | Ka-Yiu et al. |
| 2006/0172401 A1 | 8/2006 | Yamagishi |
| 2006/0205048 A1 | 9/2006 | Murase et al. |
| 2006/0228712 A1 | 10/2006 | Nakagawa et al. |
| 2006/0276674 A1 | 12/2006 | Kushiku et al. |
| 2006/0281156 A1 | 12/2006 | Aoyama et al. |
| 2007/0087423 A1 | 4/2007 | Murakami et al. |
| 2007/0154999 A1 | 7/2007 | Fukui et al. |
| 2008/0293113 A1 | 11/2008 | Koseki et al. |

FOREIGN PATENT DOCUMENTS

| | | |
|---|---|---|
| CA | 2322553 | 4/2001 |
| EP | 0075612 | 4/1983 |
| EP | 0078537 | 5/1983 |
| EP | 0389103 | 9/1990 |
| EP | 0410728 | 1/1991 |
| EP | 1096013 | 5/2001 |
| EP | 1108790 | 6/2001 |
| EP | 1748062 | 1/2007 |
| JP | 57-134500 | 8/1982 |
| JP | 57-183799 | 11/1982 |
| JP | 58-35197 | 3/1983 |
| JP | 58-77895 | 5/1983 |
| JP | 58-192900 | 11/1983 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 1-191686 | 8/1989 |
| JP | 2-072876 | 3/1990 |
| JP | 2-283289 | 11/1990 |
| JP | 3-072891 | 3/1991 |
| JP | 3-151884 | 6/1991 |
| JP | 3-210184 | 9/1991 |
| JP | 5-260985 | 10/1993 |
| JP | 06-14781 | 1/1994 |
| JP | 07-67683 | 3/1995 |
| JP | 7-304389 | 11/1995 |
| JP | 11-113588 | 4/1999 |
| JP | 11-130852 | 5/1999 |

(Continued)

OTHER PUBLICATIONS

English Language Abstract of JP 11-196887.
English Language Abstract of JP 2003-235592.
English Language Abstract of JP 2003-235593.
Database UniProt, "Acetyl-CoA Hydrolase", Accession No. Q8NMK4, Oct. 1, 2002.
Database EPO Proteins, "Sequence 32 from International Publication No. WO 03/040290", Accession No. AX771820, Jul. 2, 2003.
Database EMBL, "Sequence 31 from International Publication No. WO 03/040290", Accession No. AX771819, Jul. 2, 2003.
Database Geneseq, "C-Glutamicum Protein Fragment SEQ ID No. 6326", Accession No. AAG92572, Sep. 26, 2001.

(Continued)

Primary Examiner — Rebecca E. Prouty
(74) Attorney, Agent, or Firm — Greenblum & Bernstein, P.L.C.

(57) ABSTRACT

Coryneform bacterium is modified so that an activity of acetyl-CoA hydrolase is decreased, and succinic acid is produced by using the bacterium.

7 Claims, 7 Drawing Sheets

FOREIGN PATENT DOCUMENTS

| | | |
|---|---|---|
| JP | 11-196887 | 7/1999 |
| JP | 11-196888 | 7/1999 |
| JP | 11-206385 | 8/1999 |
| JP | 2000-500333 | 1/2000 |
| JP | 2000-037196 | 2/2000 |
| JP | 2001-161386 | 6/2001 |
| JP | 2001-190297 | 7/2001 |
| JP | 2001-514900 | 9/2001 |
| JP | 2002-511250 | 4/2002 |
| JP | 2002-191370 | 7/2002 |
| JP | 2002-291477 | 10/2002 |
| JP | 2003-171448 | 6/2003 |
| JP | 2003-199522 | 7/2003 |
| JP | 2003-235592 | 8/2003 |
| JP | 2003-235593 | 8/2003 |
| JP | 2005-095169 | 4/2005 |
| JP | 2006-238843 | 9/2006 |
| JP | 2006-320208 | 11/2006 |
| WO | 95/34672 | 12/1995 |
| WO | 97/16528 | 5/1997 |
| WO | 99/06532 | 2/1999 |
| WO | 99/09196 | 2/1999 |
| WO | 99/53035 | 10/1999 |
| WO | 01/66508 | 9/2001 |
| WO | 02/29020 | 4/2002 |
| WO | 02/36797 | 5/2002 |
| WO | 02/072855 | 9/2002 |
| WO | 03/040290 | 5/2003 |
| WO | 2005/005649 | 1/2005 |
| WO | 2005/010182 | 2/2005 |
| WO | 2005/021770 | 3/2005 |
| WO | 2005/026349 | 3/2005 |
| WO | 2005/030973 | 4/2005 |
| WO | 2005/113744 | 12/2005 |
| WO | 2005/113745 | 12/2005 |
| WO | 2006/020663 | 2/2006 |
| WO | 2006/031424 | 3/2006 |
| WO | 2006/069174 | 6/2006 |
| WO | 2007/046389 | 4/2007 |
| WO | 2007/099867 | 9/2007 |

OTHER PUBLICATIONS

Database EMBL, "Sequence 2826 from EP 1 108 790", Accession No. AX122910, May 10, 2001.
Database UniProt, "Butyryl-CoA: Acetate Coenzyme A Transferase", Accession No. Q6M2R3, Jul. 5, 2004.
Kalinowski et al., "The Complete *Corynebacterium glutamicum* ATCC 13032 Genome Sequence and its Impact on the Production of L-Aspartate-Derived Amino Acids and Vitamins", J. of Biotech., vol. 104, Nos. 1-3, pp. 5-25 (2003).
Inui et al., "Metabolic Analysis of *Corynebacterium glutamicum* During Lactate and Succinate Productions under Oxygen Deprivation Conditions", J. of Mol. Microbiol. and Biotech., vol. 7, No. 4, pp. 182-196 (2004).
Kirchner et al., "Tools for Genetic Engineering in the Amino Acid-Producing Bacterium *Corynebacterium glutamicum*", J. of Biotech., vol. 104, Nos. 1-3, pp. 287-299 (2003).
Chotani et al., "The Commercial Production of Chemicals Using Pathway Engineering", Biochimica et Biophysica Acta, Protein Structure and Molecular Enzymology, vol. 1543, No. 2, pp. 434-455 (2000).
English language Abstract of JP 11-206385.
English language Abstract of JP 06-014781.
English language Abstract of JP 07-067683.
English language Abstract of JP 11-113588, 1999.
English language Abstract of JP 2002-291477.
English language Abstract of JP 11-196888, 1999.
Reinscheid et al., Cloning, Sequence Analysis, Expression and Inactivation of the *Corynebacterium glutamicum* pta-ack Operon Encoding Phosphotransacetylase and Acetate Kinase, Microbiology, vol. 145, pp. 503-513 (1999).
Guettler et al., *Actinobacillus succinogenes* sp. nov., A Novel Succinic-Acid-Producing Strain from the Bovin Rumen, International Journal of Systematic Bacteriology, vol. 49, pp. 207-216 (1999).
NP_601767, NCBI Sequence Viewer, Acetyl-CoA hydrolase, Dec. 2006.
NP_601811, NCBI Sequence Viewer, Pyruvate Dehyrogenase, Dec. 2006.
English Language Abstract of JP 1-191686, 1989.
English Language Abstract of JP 2-072876, 1990
English Language Abstract of JP 3-072891, 1991.
English Language Abstract of JP 3-210184, 1991.
English Language Abstract of JP 5-260985, 1993.
English Language Abstract of JP 7-304839, 1995
English Language Abstract of JP 11-130852, 1999.
English Language Abstract of JP 57-134500, 1982.
English Language Abstract of JP 57-183799, 1982.
English Language Abstract of JP 58-035197, 1983.
English Language Abstract of JP 58-077895, 1983.
English Language Abstract of JP 58-192900, 1983.
English Language Abstract of JP 61-209596, 1986.
English Language Abstract of JP 62-048394, 1987.
English Language Abstract of JP 62-238231, 1987.
English Language Abstract of JP 62-238232, 1987.
English Language Abstract of JP 2000-037196.
English Language Abstract of JP 2001-161386.
English Language Abstract of JP 2001-190297.
English Language Abstract of JP 2002-191370.
English Language Abstract of JP 2003-171448.
English Language Abstract of JP 2003-199522.
English Language Abstract of JP 2005-095196.
English Language Abstract of JP 2006-238843.
English Language Abstract of JP 2006-320208.
Arikawa et al. *J. Biosci. Bioeng.* 87(1):28-36, 1999.
Ba et al. *Biomacromolecules* 4:1827-1834, 2003.
Bott et al. *Journal of Biotechnology* 104:129-153, 2003.
Branden et al. *Introduction to Protein Structure*, Garland Publishing Inc., New York, p. 247, 1991.
Calvary et al. *Microchemical Journal* 23(4):473-480, 1978.
Chang et al. *J. Bacteriol.* 151:1279-1289, 1982.
Dunn et al. *J. Bacteriol.* 178:5960-5970, 1996.
Gergely et al. *J. Biol. Chem.* 198:323-334, 1952.
Gokarn et al. *Biotechnology Letters* 20(8):795-798, 1998.
Gokarn et al. *Applied and Environmental Microbiology* 66(5):1844-1850, 2000.
Gokarn et al. *Appl. Microbiol. Biotechnol.* 56:188-195, 2001.
Goldberg et al. *Applied and Environmental Microbiology* 45(6):1838-1847, 1983.
Gong et al. *Applied Biochemistry and Biotechnology* 57/58:481-487, 1996.
Hong et al. *Biotechnology and Bioengineering* 74(2):89-95, 2001.
Hong et al. *Applied Microbiology and Biotechnology* 58:286-290, 2002.
Jaurin et al. GenBank accession No. J01611, Feb. 2000.
Kanarek et al. *J. Biol. Chem.* 239:4202-4206, 1964.
KEGG Database on-line, NCg10359, 2006.
KEGG Database on-line, NCg10360, 2006.
KEGG Database on-line, NCg10361, 2006.
Klotzsch et al., *Meth. Enzymol.* 12:381-386, 1969.
Kondo et al. *Gene* 191:47-50, 1997.
Kurokawa et al. *Arch. Microbiol.* 183:317-324, 2005.
Lehn et al. *Gene* 165:331-332, 1995.
Liebl et al. *International Journal of Systemic Bacteriology* 41:255-260, 1991.
Lin et al. *Applied Genetics and Molecular Biotechnology*, published online: Nov. 24, 2004, total pp. 16.
MacKay et al. *Biochem. Biophys. Res. Comm.* 202:1000-1014, 1994.
Mat-Jan et al. *Journal of Bacteriology* 171(1):342-348, 1989.
Maxa et al. *Mitteilungen Klosterneuburg* 41(6):223-237, 1991.
Millard et al. *Applied and Environmental Microbiology* 62(5):1808-1810, 1996.
Peters-Windisch et al. *Microbiology* 144:915-927, 1998.
Ramponi, *Meth. Enzymol.* 42:409-426, 1975.
Schafer et al., *Gene* 145:69-73, 1994.
Schnorpfeil et al. *Eur. J. Biochem.* 268:3069-3074, 2001.
Seffernick et al. *J. Bacteriol.* 183(8):2405-2410, 2001.
Shiio et al. *Agric. Biol. Chem.* 44(8):1897-1904, 1980.

Song et al. *Enzyme Microbiol. Technol.* 309:352-361, 2006.
Stols et al. *Applied and Environmental Microbiology* 63(7):2695-2701, 1997.
Stucka et al. *Mol. Gen. Genet.* 229:307-315, 1991.
Tomar et al. *Appl. Microbiol. Biotechnol.* 62:76-82, 2003.
Torino et al. *J. Appl. Microbiol.* 91:846-852, 2001.
Uematsu et al. *Plant Cell Reports* 10:286-290, 1991.
Usuda et al. *Microbiology* 142:3347-3354, 1996.
Vertes et al. *Res. Microbiol.* 144:181-185, 1993.
Wang et al. *Applied Biochemistry and Biotechnology* 70-72:919-928, 1998.
Whisstock et al. *Q. Rev. Biophysics* 36(3):307-340, 2003.
Witkowski et al. *Biochemistry* 38:11643-11650, 1999.
Zeikus et al. *Appl. Microbiol. Biotechnol.* 51:545-552, 1999.
Zhang et al. *Proc. Natl. Acad. Sci. USA* 90:1766-1770, 1993.
U.S. Appl. No. 12/090,431 to Koseki et al., filed Apr. 16, 2008, now abandoned.
U.S. Appl. No. 12/280,426 to Murase et al., filed Dec. 9, 2008.

SEQUENCE LISTING

```
<160> NUMBER OF SEQ ID NOS: 47

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgggatcctt tttaacccat caca                                            24

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatcttc aaaaggttag gaatacggt                                       29

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 cctttttgaag atcgaccagt tgg                                            23

<210> SEQ ID NO 4
```

```
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tacctggaat gctgttttcc cagggatcgc agtggtgagt aacc                    44

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctgggaaaa cagcattcca ggtattag                                      28

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgcaggtcga ctctagagga tcc                                           23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cactgcacgg ccctgcgaac                                               20

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgccaactag gcgccaaaaa ttcctgattt ccctaaccgg ac                      42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtccggttag ggaaatcagg aattttttggc gcctagttgg cg                     42

<210> SEQ ID NO 10
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 10
tgtgggcctt cggcgaggac                                                    20

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagtcgaccg caccccattt ttcata                                             26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggtcgacgt gaatgctcgg cgggatcc                                           28

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttccatctt cctcatggtg ctgc                                               24

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccaggagagc taagcgaact ccattagctg cgtcctcctg cctg                         44

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caggcaggag gacgcagcta atggagttcg cttagctctc ctgg                         44

<210> SEQ ID NO 16
<211> LENGTH: 31
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 16
gcgtctagac ctttaggagt gcgatgtccc c                                            31

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcgtctagac gactgtgctg ttaacccgaa ccc                                          33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgtctagag agttaggccc ttagaagcga ttc                                          33

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctcaaagcg tggaattgag atcg                                                    24

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccaggagagc taagcgaact ttcggcgctc atgactggtt cg                                42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgaaccagtc atgagcgccg aaagttcgct tagctctcct gg                                42

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 22
gcgtctagag tacgcaaggc ggacgaacgc                                              30

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccttgatat cttcccgcaa acc                                                     23

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttgtggtcc tggaaacaca caccgaagtg aatttcgcag agattgc                           47

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcaatctct gcgaaattca cttcggtgtg tgtttccagg accacaag                          48

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggtttctcgg ggtctaaacc gg                                                      22

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggaatctag accacgccaa tggaaatttc tcc                                          33

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```

```
gggaatctag acgtgacaag atctggcgaa atcgc                               35
```

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
gcttctgcgc aaagcaagcc tccg                                           24
```

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gtccgattac ctgaggaggt attcccatga aggcataagt ttttcttgg                50
```

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
ccaagaaaaa acttatgcct tcatgggaat acctcctcag gtaatcggac                50
```

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ggtcatgtgc atggttttct cattgc                                         26
```

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ggcctctaga cctgcaccga tcaggatgag tgg                                 33
```

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gcgctctaga ctcaacaaga gcacgcgcag tcacc                               35
```

<210> SEQ ID NO 35
<211> LENGTH: 2014
<212> TYPE: DNA
<213> ORGANISM: Bacillus subtilis
<220> FEATURE:
<221> NAME/KEY: CDS
<222> LOCATION: (464)..(1882)

<400> SEQUENCE: 35

| | |
|---|---|
| gatccttttt aacccatcac atataccgtc cgttcactat tatttagtga aatgagatat | 60 |
| tatgatattt tctgaattgt gattaaaaag gcaactttat gcccatgcaa cagaaactat | 120 |
| aaaaaataca gagaatgaaa agaaacagat agatttttta gttctttagg cccgtagtct | 180 |
| gcaaatcctt ttatgatttt ctatcaaaca aagaggaaaa atagaccagt tgcaatccaa | 240 |
| acgagagtct aatagaatga ggtcgaaaag taaatcgcgc gggtttgtta ctgataaagc | 300 |
| aggcaagacc taaatgtgt aaagggcaaa gtgtatactt tggcgtcacc ccttacatat | 360 |
| tttaggtctt tttttattgt gcgtaactaa cttgccatct tcaaacagga gggctggaag | 420 |
| aagcagaccg ctaacacagt acataaaaaa ggagacatga acg atg aac atc aaa | 475 |
| Met Asn Ile Lys | |
| 1 | |

```
aag ttt gca aaa caa gca aca gta tta acc ttt act acc gca ctg ctg     523
Lys Phe Ala Lys Gln Ala Thr Val Leu Thr Phe Thr Thr Ala Leu Leu
  5                  10                  15                  20 gca gga ggc gca act caa gcg ttt gcg aaa gaa acg aac caa aag cca     571
Ala Gly Gly Ala Thr Gln Ala Phe Ala Lys Glu Thr Asn Gln Lys Pro
                 25                  30                  35 tat aag gaa aca tac ggc att tcc cat att aca cgc cat gat atg ctg     619
Tyr Lys Glu Thr Tyr Gly Ile Ser His Ile Thr Arg His Asp Met Leu
             40                  45                  50 caa atc cct gaa cag caa aaa aat gaa aaa tat caa gtt cct gaa ttc     667
Gln Ile Pro Glu Gln Gln Lys Asn Glu Lys Tyr Gln Val Pro Glu Phe
         55                  60                  65 gat tcg tcc aca att aaa aat atc tct tct gca aaa ggc ctg gac gtt     715
Asp Ser Ser Thr Ile Lys Asn Ile Ser Ser Ala Lys Gly Leu Asp Val
     70                  75                  80 tgg gac agc tgg cca tta caa aac gct gac ggc act gtc gca aac tat     763
Trp Asp Ser Trp Pro Leu Gln Asn Ala Asp Gly Thr Val Ala Asn Tyr
 85                  90                  95                 100 cac ggc tac cac atc gtc ttt gca tta gcc gga gat cct aaa aat gcg     811
His Gly Tyr His Ile Val Phe Ala Leu Ala Gly Asp Pro Lys Asn Ala
                105                 110                 115 gat gac aca tcg att tac atg ttc tat caa aaa gtc ggc gaa act tct     859
Asp Asp Thr Ser Ile Tyr Met Phe Tyr Gln Lys Val Gly Glu Thr Ser
            120                 125                 130 att gac agc tgg aaa aac gct ggc cgc gtc ttt aaa gac agc gac aaa     907
Ile Asp Ser Trp Lys Asn Ala Gly Arg Val Phe Lys Asp Ser Asp Lys
        135                 140                 145 ttc gat gca aat gat tct atc cta aaa gac caa aca caa gaa tgg tca     955
Phe Asp Ala Asn Asp Ser Ile Leu Lys Asp Gln Thr Gln Glu Trp Ser
    150                 155                 160 ggt tca gcc aca ttt aca tct gac gga aaa atc cgt tta ttc tac act    1003
Gly Ser Ala Thr Phe Thr Ser Asp Gly Lys Ile Arg Leu Phe Tyr Thr
165                 170                 175                 180 gat ttc tcc ggt aaa cat tac ggc aaa caa aca ctg aca act gca caa    1051
Asp Phe Ser Gly Lys His Tyr Gly Lys Gln Thr Leu Thr Thr Ala Gln
                185                 190                 195 gtt aac gta tca gca tca gac agc tct ttg aac atc aac ggt gta gag    1099
Val Asn Val Ser Ala Ser Asp Ser Ser Leu Asn Ile Asn Gly Val Glu
```

```
                      200                 205                 210
gat tat aaa tca atc ttt gac ggt gac gga aaa acg tat caa aat gta        1147
Asp Tyr Lys Ser Ile Phe Asp Gly Asp Gly Lys Thr Tyr Gln Asn Val
        215                 220                 225 cag cag ttc atc gat gaa ggc aac tac agc tca ggc gac aac cat acg        1195
Gln Gln Phe Ile Asp Glu Gly Asn Tyr Ser Ser Gly Asp Asn His Thr
    230                 235                 240 ctg aga gat cct cac tac gta gaa gat aaa ggc cac aaa tac tta gta        1243
Leu Arg Asp Pro His Tyr Val Glu Asp Lys Gly His Lys Tyr Leu Val
245                 250                 255                 260 ttt gaa gca aac act gga act gaa gat ggc tac caa ggc gaa gaa tct        1291
Phe Glu Ala Asn Thr Gly Thr Glu Asp Gly Tyr Gln Gly Glu Glu Ser
                265                 270                 275 tta ttt aac aaa gca tac tat ggc aaa agc aca tca ttc ttc cgt caa        1339
Leu Phe Asn Lys Ala Tyr Tyr Gly Lys Ser Thr Ser Phe Phe Arg Gln
            280                 285                 290 gaa agt caa aaa ctt ctg caa agc gat aaa aaa cgc acg gct gag tta        1387
Glu Ser Gln Lys Leu Leu Gln Ser Asp Lys Lys Arg Thr Ala Glu Leu
        295                 300                 305 gca aac ggc gct ctc ggt atg att gag cta aac gat gat tac aca ctg        1435
Ala Asn Gly Ala Leu Gly Met Ile Glu Leu Asn Asp Asp Tyr Thr Leu
    310                 315                 320 aaa aaa gtg atg aaa ccg ctg att gca tct aac aca gta aca gat gaa        1483
Lys Lys Val Met Lys Pro Leu Ile Ala Ser Asn Thr Val Thr Asp Glu
325                 330                 335                 340 att gaa cgc gcg aac gtc ttt aaa atg aac ggc aaa tgg tac ctg ttc        1531
Ile Glu Arg Ala Asn Val Phe Lys Met Asn Gly Lys Trp Tyr Leu Phe
                345                 350                 355 act gac tcc cgc gga tca aaa atg acg att gac ggc att acg tct aac        1579
Thr Asp Ser Arg Gly Ser Lys Met Thr Ile Asp Gly Ile Thr Ser Asn
            360                 365                 370 gat att tac atg ctt ggt tat gtt tct aat tct tta act ggc cca tac        1627
Asp Ile Tyr Met Leu Gly Tyr Val Ser Asn Ser Leu Thr Gly Pro Tyr
        375                 380                 385 aag ccg ctg aac aaa act ggc ctt gtg tta aaa atg gat ctt gat cct        1675
Lys Pro Leu Asn Lys Thr Gly Leu Val Leu Lys Met Asp Leu Asp Pro
    390                 395                 400 aac gat gta acc ttt act tac tca cac ttc gct gta cct caa gcg aaa        1723
Asn Asp Val Thr Phe Thr Tyr Ser His Phe Ala Val Pro Gln Ala Lys
405                 410                 415                 420 gga aac aat gtc gtg att aca agc tat atg aca aac aga gga ttc tac        1771
Gly Asn Asn Val Val Ile Thr Ser Tyr Met Thr Asn Arg Gly Phe Tyr
                425                 430                 435 gca gac aaa caa tca acg ttt gcg cca agc ttc ctg ctg aac atc aaa        1819
Ala Asp Lys Gln Ser Thr Phe Ala Pro Ser Phe Leu Leu Asn Ile Lys
            440                 445                 450 ggc aag aaa aca tct gtt gtc aaa gac agc atc ctt gaa caa gga caa        1867
Gly Lys Lys Thr Ser Val Val Lys Asp Ser Ile Leu Glu Gln Gly Gln
        455                 460                 465 tta aca gtt aac aaa taaaaacgca aagaaaatg ccgatatcct attggcattt         1922
Leu Thr Val Asn Lys
    470 tcttttatt cttatcaaca taaggtgaa tcccatatga actatataaa agcaggcaaa        1982
tggctaaccg tattcctaac cttttgaaga tc                                    2014

<210> SEQ ID NO 36
<211> LENGTH: 473
<212> TYPE: PRT
<213> ORGANISM: Bacillus subtilis
```

```
<400> SEQUENCE: 36

Met Asn Ile Lys Lys Phe Ala Lys Gln Ala Thr Val Leu Thr Phe Thr
 1               5                  10                  15

Thr Ala Leu Leu Ala Gly Gly Ala Thr Gln Ala Phe Ala Lys Glu Thr
             20                  25                  30

Asn Gln Lys Pro Tyr Lys Glu Thr Tyr Gly Ile Ser His Ile Thr Arg
         35                  40                  45

His Asp Met Leu Gln Ile Pro Glu Gln Gln Lys Asn Glu Lys Tyr Gln
     50                  55                  60

Val Pro Glu Phe Asp Ser Ser Thr Ile Lys Asn Ile Ser Ser Ala Lys
 65                  70                  75                  80

Gly Leu Asp Val Trp Asp Ser Trp Pro Leu Gln Asn Ala Asp Gly Thr
                 85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415
```

```
            Pro Gln Ala Lys Gly Asn Asn Val Val Ile Thr Ser Tyr Met Thr Asn
                        420                 425                 430

Arg Gly Phe Tyr Ala Asp Lys Gln Ser Thr Phe Ala Pro Ser Phe Leu
                        435                 440                 445

Leu Asn Ile Lys Gly Lys Lys Thr Ser Val Val Lys Asp Ser Ile Leu
                        450                 455                 460

Glu Gln Gly Gln Leu Thr Val Asn Lys
            465                 470

<210> SEQ ID NO 37
<211> LENGTH: 2820
<212> TYPE: DNA
<213> ORGANISM: Corynebacterium glutamicum
<220> FEATURE:
<221> NAME/KEY: CDS
<222> LOCATION: (898)..(1851)

<400> SEQUENCE: 37
tgcagaatta tgcaagatgc gccgcaacaa aacgcgatcg gccaaggtca aagtggtcaa       60
tgtaatgacc gaaaccgctg cgatgaaact tatccacggc ggtaaaaacc tctcaattag      120
gagcttgacc tcattaatac tgtgctgggt taattcgccg gtgatcagca gcgcgccgta      180
ccccaaggtg ccgacactaa tgcccgcgat cgtctccttc ggtccaaaat tcttctgccc      240
aatcagccgg atttgggtgc gatgcctgat caatcccaca accgtggtgg tcaacgtgat      300
ggcaccagtt gcgatgtggg tggcgttgta aattttcctg ataccccgcc ggttggttct      360
ggggaggatc gagtggattc ccgtcgctgc cgcatgcccc accgcttgta aaacagccag      420
gttagcagcc gtaacccacc acggtttcgg caacaatgac ggcgagagag cccaccacat      480
tgcgatttcc gctccgataa agccagcgcc catatttgca gggaggattc gcctgcggtt      540
tggcgacatt cggatccccg gaactagctc tgcaatgacc tgcgcgccga gggaggcgag      600
gtgggtggca ggttttagtg cgggtttaag cgttgccagg cgagtggtga gcagagacgc      660
tagtctgggg agcgaaacca tattgagtca tcttggcaga gcatgcacaa ttctgcaggg      720
cataggttgg ttttgctcga tttacaatgt gattttttca acaaaaataa cacttggtct      780
gaccacattt tcggacataa tcgggcataa ttaaaggtgt aacaaaggaa tccgggcaca      840
agctcttgct gattttctga gctgcttgtg gggttgtccg gttagggaaa tcaggaa         897 gtg gga tcg aaa atg aaa gaa acc gtc ggt aac aag att gtc ctc att        945
Val Gly Ser Lys Met Lys Glu Thr Val Gly Asn Lys Ile Val Leu Ile
 1               5                  10                  15 ggc gca gga gat gtt gga gtt gca tac gca tac gca ctg atc aac cag        993
Gly Ala Gly Asp Val Gly Val Ala Tyr Ala Tyr Ala Leu Ile Asn Gln
                20                  25                  30 ggc atg gca gat cac ctt gcg atc atc gac atc gat gaa aag aaa ctc       1041
Gly Met Ala Asp His Leu Ala Ile Ile Asp Ile Asp Glu Lys Lys Leu
            35                  40                  45 gaa ggc aac gtc atg gac tta aac cat ggt gtt gtg tgg gcc gat tcc       1089
Glu Gly Asn Val Met Asp Leu Asn His Gly Val Val Trp Ala Asp Ser
        50                  55                  60 cgc acc cgc gtc acc aag ggc acc tac gct gac tgc gaa gac gca gcc       1137
Arg Thr Arg Val Thr Lys Gly Thr Tyr Ala Asp Cys Glu Asp Ala Ala
65                  70                  75                  80 atg gtt gtc att tgt gcc ggc gca gcc caa aag cca ggc gag acc cgc       1185
Met Val Val Ile Cys Ala Gly Ala Ala Gln Lys Pro Gly Glu Thr Arg
                85                  90                  95 ctc cag ctg gtg gac aaa aac gtc aag att atg aaa tcc atc gtc ggc       1233
Leu Gln Leu Val Asp Lys Asn Val Lys Ile Met Lys Ser Ile Val Gly
                100                 105                 110
```

```
gat gtc atg gac agc gga ttc gac ggc atc ttc ctc gtg gcg tcc aac      1281
Asp Val Met Asp Ser Gly Phe Asp Gly Ile Phe Leu Val Ala Ser Asn
            115                 120                 125 cca gtg gat atc ctg acc tac gca gtg tgg aaa ttc tcc ggc ttg gaa      1329
Pro Val Asp Ile Leu Thr Tyr Ala Val Trp Lys Phe Ser Gly Leu Glu
    130                 135                 140 tgg aac cgc gtg atc ggc tcc gga act gtc ctg gac tcc gct cga ttc      1377
Trp Asn Arg Val Ile Gly Ser Gly Thr Val Leu Asp Ser Ala Arg Phe
145                 150                 155                 160 cgc tac atg ctg ggc gaa ctc tac gaa gtg gca cca agc tcc gtc cac      1425
Arg Tyr Met Leu Gly Glu Leu Tyr Glu Val Ala Pro Ser Ser Val His
                165                 170                 175 gcc tac atc atc ggc gaa cac ggc gac act gaa ctt cca gtc ctg tcc      1473
Ala Tyr Ile Ile Gly Glu His Gly Asp Thr Glu Leu Pro Val Leu Ser
            180                 185                 190 tcc gcg acc atc gca ggc gta tcg ctt agc cga atg ctg gac aaa gac      1521
Ser Ala Thr Ile Ala Gly Val Ser Leu Ser Arg Met Leu Asp Lys Asp
        195                 200                 205 cca gag ctt gag ggc cgt cta gag aaa att ttc gaa gac acc cgc gac      1569
Pro Glu Leu Glu Gly Arg Leu Glu Lys Ile Phe Glu Asp Thr Arg Asp
    210                 215                 220 gct gcc tat cac att atc gac gcc aag ggc tcc act tcc tac ggc atc      1617
Ala Ala Tyr His Ile Ile Asp Ala Lys Gly Ser Thr Ser Tyr Gly Ile
225                 230                 235                 240 ggc atg ggt ctt gct cgc atc acc cgc gca atc ctg cag aac caa gac      1665
Gly Met Gly Leu Ala Arg Ile Thr Arg Ala Ile Leu Gln Asn Gln Asp
                245                 250                 255 gtt gca gtc cca gtc tct gca ctg ctc cac ggt gaa tac ggt gag gaa      1713
Val Ala Val Pro Val Ser Ala Leu Leu His Gly Glu Tyr Gly Glu Glu
            260                 265                 270 gac atc tac atc ggc acc cca gct gtg gtg aac cgc cga ggc atc cgc      1761
Asp Ile Tyr Ile Gly Thr Pro Ala Val Val Asn Arg Arg Gly Ile Arg
        275                 280                 285 cgc gtt gtc gaa cta gaa atc acc gac cac gag atg gaa cgc ttc aag      1809
Arg Val Val Glu Leu Glu Ile Thr Asp His Glu Met Glu Arg Phe Lys
    290                 295                 300 cat tcc gca aat acc ctg cgc gaa att cag aag cag ttc ttc              1851
His Ser Ala Asn Thr Leu Arg Glu Ile Gln Lys Gln Phe Phe
305                 310                 315 taaatctttg gcgcctagtt ggcgacgcaa gtgtttcatt ggaacacttg cgctgccaac   1911
tttttggttt acgggcacaa tgaaactgtt ggatggaatt tagagtgttt gtagcttaag   1971
gagctcaaat gaatgagttt gaccaggaca ttctccagga gatcaagact gaactcgacg   2031
agttaattct agaacttgat gaggtgacac aaactcacag cgaggccatc gggcaggtct   2091
ccccaaccca ttacgttggt gcccgcaacc tcatgcatta cgcgcatctt cgcaccaaag   2151
acctccgtgg cctgcagcaa cgcctctcct ctgtgggagc tacccgcttg actaccaccg   2211
aaccagcagt gcaggcccgc tcaaggccg cccgcaatgt tatcggagct ttcgcaggtg   2271
aaggcccact ttatccaccc tcagatgtcg tcgatgcctt cgaagatgcc gatgagattc   2331
tcgacgagca cgccgaaatt ctccttggcg aacccctacc ggatactcca tcctgcatca   2391
tggtcaccct gcccaccgaa gccgccaccg acattgaact tgtccgtggc ttcgccaaaa   2451
gcggcatgaa tctagctcgc atcaactgtg cacacgacga tgaaaccgtc tggaagcaga   2511
tgatcgacaa cgtccacacc gttgcagaag aagttggccg ggaaatccgc gtcagcatgg   2571
acctcgccgg accaaaagta cgcaccgcg aaatcgcccc aggcgcagaa gtaggtcgcg   2631
cacgagtaac ccgcgacgaa accggaaaag tactgacgcc cgcaaaactg tggatcaccg   2691
```

-continued

```
cccacggctc cgaaccagtc ccagcccccg aaagcctgcc cggtcgcccc gctctgccga    2751
ttgaagtcac cccagaatgg ttcgacaaac tagaaatcgg cagcgtcatc aacgtcccag    2811
acacccgcg                                                           2820
```

```
<210> SEQ ID NO 38
<211> LENGTH: 318
<212> TYPE: PRT
<213> ORGANISM: Corynebacterium glutamicum

<400> SEQUENCE: 38
```

| | | | | | | | | | | | | | | |
|---|---|---|---|---|---|---|---|---|---|---|---|---|---|---|
| Val | Gly | Ser | Lys | Met | Lys | Glu | Thr | Val | Gly | Asn | Lys | Ile | Val | Leu | Ile |
| 1 | | | | 5 | | | | | 10 | | | | | 15 | |
| Gly | Ala | Gly | Asp | Val | Gly | Val | Ala | Tyr | Ala | Tyr | Ala | Leu | Ile | Asn | Gln |
| | | | 20 | | | | | 25 | | | | | 30 | | |
| Gly | Met | Ala | Asp | His | Leu | Ala | Ile | Ile | Asp | Ile | Asp | Glu | Lys | Lys | Leu |
| | | 35 | | | | | 40 | | | | | 45 | | | |
| Glu | Gly | Asn | Val | Met | Asp | Leu | Asn | His | Gly | Val | Val | Trp | Ala | Asp | Ser |
| | 50 | | | | | 55 | | | | | 60 | | | | |
| Arg | Thr | Arg | Val | Thr | Lys | Gly | Thr | Tyr | Ala | Asp | Cys | Glu | Asp | Ala | Ala |
| 65 | | | | | 70 | | | | | 75 | | | | | 80 |
| Met | Val | Val | Ile | Cys | Ala | Gly | Ala | Ala | Gln | Lys | Pro | Gly | Glu | Thr | Arg |
| | | | | 85 | | | | | 90 | | | | | 95 | |
| Leu | Gln | Leu | Val | Asp | Lys | Asn | Val | Lys | Ile | Met | Lys | Ser | Ile | Val | Gly |
| | | | 100 | | | | | 105 | | | | | 110 | | |
| Asp | Val | Met | Asp | Ser | Gly | Phe | Asp | Gly | Ile | Phe | Leu | Val | Ala | Ser | Asn |
| | | 115 | | | | | 120 | | | | | 125 | | | |
| Pro | Val | Asp | Ile | Leu | Thr | Tyr | Ala | Val | Trp | Lys | Phe | Ser | Gly | Leu | Glu |
| | 130 | | | | | 135 | | | | | 140 | | | | |
| Trp | Asn | Arg | Val | Ile | Gly | Ser | Gly | Thr | Val | Leu | Asp | Ser | Ala | Arg | Phe |
| 145 | | | | | 150 | | | | | 155 | | | | | 160 |
| Arg | Tyr | Met | Leu | Gly | Glu | Leu | Tyr | Glu | Val | Ala | Pro | Ser | Ser | Val | His |
| | | | | 165 | | | | | 170 | | | | | 175 | |
| Ala | Tyr | Ile | Ile | Gly | Glu | His | Gly | Asp | Thr | Glu | Leu | Pro | Val | Leu | Ser |
| | | | 180 | | | | | 185 | | | | | 190 | | |
| Ser | Ala | Thr | Ile | Ala | Gly | Val | Ser | Leu | Ser | Arg | Met | Leu | Asp | Lys | Asp |
| | | 195 | | | | | 200 | | | | | 205 | | | |
| Pro | Glu | Leu | Glu | Gly | Arg | Leu | Glu | Lys | Ile | Phe | Glu | Asp | Thr | Arg | Asp |
| | 210 | | | | | 215 | | | | | 220 | | | | |
| Ala | Ala | Tyr | His | Ile | Ile | Asp | Ala | Lys | Gly | Ser | Thr | Ser | Tyr | Gly | Ile |
| 225 | | | | | 230 | | | | | 235 | | | | | 240 |
| Gly | Met | Gly | Leu | Ala | Arg | Ile | Thr | Arg | Ala | Ile | Leu | Gln | Asn | Gln | Asp |
| | | | | 245 | | | | | 250 | | | | | 255 | |
| Val | Ala | Val | Pro | Val | Ser | Ala | Leu | Leu | His | Gly | Glu | Tyr | Gly | Glu | Glu |
| | | | 260 | | | | | 265 | | | | | 270 | | |
| Asp | Ile | Tyr | Ile | Gly | Thr | Pro | Ala | Val | Val | Asn | Arg | Arg | Gly | Ile | Arg |
| | | 275 | | | | | 280 | | | | | 285 | | | |
| Arg | Val | Val | Glu | Leu | Glu | Ile | Thr | Asp | His | Glu | Met | Glu | Arg | Phe | Lys |
| | 290 | | | | | 295 | | | | | 300 | | | | |
| His | Ser | Ala | Asn | Thr | Leu | Arg | Glu | Ile | Gln | Lys | Gln | Phe | Phe | | |
| 305 | | | | | 310 | | | | | 315 | | | | | |

```
<210> SEQ ID NO 39
<211> LENGTH: 4200
<212> TYPE: DNA
<213> ORGANISM: Corynebacterium glutamicum
```

```
<220> FEATURE:
<221> NAME/KEY: CDS
<222> LOCATION: (956)..(1942)
<220> FEATURE:
<221> NAME/KEY: CDS
<222> LOCATION: (1945)..(3135)

<400> SEQUENCE: 39
```

| | | | | | |
|---|---|---|---|---|---|
| cctgctggac | ctgcaccgac | aacggcaaca | cgcaaagggc | gagacatata | aagttcgatt | 60 |
| ccttaaaggg | gttctaaaaa | atgtggagta | tgtgagcggg | ggttccactt | gtagattcga | 120 |
| ctcctatcgg | ggtgcgactg | ctaatggtgc | cctgctatca | accctccatg | atacgtggta | 180 |
| agtgcagact | aataaaggcc | agtcggggag | tattgggggc | tttgctgggg | tcagatttgt | 240 |
| cacgctgcgc | gctttcatag | accccattaa | tggggggtga | agagctgtaa | agtaccgcta | 300 |
| aaaactttgc | aaagggtgct | tcgcaacttg | taaccgctcc | gtattgtttt | ctacggcaat | 360 |
| aagcatttgt | gctgctcaaa | gcgtggaatt | gagatcggtt | tgaaaattac | aaaataaaac | 420 |
| tttgcaaacc | gggctgtacg | caaggcggac | gaacgctaaa | ctatgtaaga | aatcacaacc | 480 |
| tccctcatt | agtgccagga | ggcacaagcc | tgaagtgtca | tcaatgagaa | ggttcaggct | 540 |
| gaaattagaa | aggcgatgta | tgtctgacac | accgacctca | gctctgatca | ccacggtcaa | 600 |
| ccgcagcttc | gatggattcg | atttggaaga | agtagcagca | gaccttggag | ttcggctcac | 660 |
| ctacctgccc | gacgaagaac | tagaagtatc | caaagttctc | gcggcggacc | tcctcgctga | 720 |
| ggggccagct | ctcatcatcg | gtgtaggaaa | cacgtttttc | gacgcccagg | tcgccgctgc | 780 |
| cctcggcgtc | ccagtgctac | tgctggtaga | caagcaaggc | aagcacgttg | ctcttgctcg | 840 |
| cacccaggta | aacaatgccg | gcgcagttgt | tgcagcagca | tttaccgctg | aacaagagcc | 900 |
| aatgccggat | aagctgcgca | aggctgtgcg | caaccacagc | aacctcgaac | cagtc atg | 958 |
| | | | | | Met | |
| | | | | | 1 | |

```
agc gcc gaa ctc ttt gaa aac tgg ctg ctc aag cgc gca cgc gca gag    1006
Ser Ala Glu Leu Phe Glu Asn Trp Leu Leu Lys Arg Ala Arg Ala Glu
        5                  10                  15 cac tcc cac att gtg ctg cca gaa ggt gac gac gac cgc atc ttg atg    1054
His Ser His Ile Val Leu Pro Glu Gly Asp Asp Asp Arg Ile Leu Met
    20                  25                  30 gct gcc cac cag ctg ctt gat caa gac atc tgt gac atc acg atc ctg    1102
Ala Ala His Gln Leu Leu Asp Gln Asp Ile Cys Asp Ile Thr Ile Leu
35                  40                  45 ggc gat cca gta aag atc aag gag cgc gct acc gaa ctt ggc ctg cac    1150
Gly Asp Pro Val Lys Ile Lys Glu Arg Ala Thr Glu Leu Gly Leu His
50                  55                  60                  65 ctt aac act gca tac ctg gtc aat ccg ctg aca gat cct cgc ctg gag    1198
Leu Asn Thr Ala Tyr Leu Val Asn Pro Leu Thr Asp Pro Arg Leu Glu
                70                  75                  80 gaa ttc gcc gaa caa ttc gcg gag ctg cgc aag tca aag agc gtc act    1246
Glu Phe Ala Glu Gln Phe Ala Glu Leu Arg Lys Ser Lys Ser Val Thr
            85                  90                  95 atc gat gaa gcc cgc gaa atc atg aag gat att tcc tac ttc ggc acc    1294
Ile Asp Glu Ala Arg Glu Ile Met Lys Asp Ile Ser Tyr Phe Gly Thr
        100                 105                 110 atg atg gtc cac aac ggc gac gcc gac gga atg gta tcc ggt gca gca    1342
Met Met Val His Asn Gly Asp Ala Asp Gly Met Val Ser Gly Ala Ala
    115                 120                 125 aac acc acc gca cac acc att aag cca agc ttc cag atc atc aaa act    1390
Asn Thr Thr Ala His Thr Ile Lys Pro Ser Phe Gln Ile Ile Lys Thr
130                 135                 140                 145 gtt cca gaa gca tcc gtc gtt tct tcc atc ttc ctc atg gtg ctg cgc    1438
```

```
Val Pro Glu Ala Ser Val Val Ser Ser Ile Phe Leu Met Val Leu Arg
            150                 155                 160 ggg cga ctg tgg gca ttc ggc gac tgt gct gtt aac ccg aac cca act    1486
Gly Arg Leu Trp Ala Phe Gly Asp Cys Ala Val Asn Pro Asn Pro Thr
            165                 170                 175 gct gaa cag ctt ggt gaa atc gcc gtt gtg tca gca aaa act gca gca    1534
Ala Glu Gln Leu Gly Glu Ile Ala Val Val Ser Ala Lys Thr Ala Ala
            180                 185                 190 caa ttt ggc att gat cct cgc gta gcc atc ttg tcc tac tcc act ggc    1582
Gln Phe Gly Ile Asp Pro Arg Val Ala Ile Leu Ser Tyr Ser Thr Gly
            195                 200                 205 aac tcc ggc gga ggc tca gat gtg gat cgc gcc atc gac gct ctt gca    1630
Asn Ser Gly Gly Gly Ser Asp Val Asp Arg Ala Ile Asp Ala Leu Ala
210                 215                 220                 225 gaa gca cgc cga ctt aac cca gaa cta tgc gtc gat gga cca ctt cag    1678
Glu Ala Arg Arg Leu Asn Pro Glu Leu Cys Val Asp Gly Pro Leu Gln
                230                 235                 240 ttc gac gcc gcc gtc gac ccg ggt gtg gcg cgc aag aag atg cca gac    1726
Phe Asp Ala Ala Val Asp Pro Gly Val Ala Arg Lys Lys Met Pro Asp
            245                 250                 255 tct gac gtc gct ggc cag gca aat gtg ttt atc ttc cct gac ctg gaa    1774
Ser Asp Val Ala Gly Gln Ala Asn Val Phe Ile Phe Pro Asp Leu Glu
            260                 265                 270 gcc gga aac atc ggc tac aaa act gca caa cgc acc ggt cac gcc ctg    1822
Ala Gly Asn Ile Gly Tyr Lys Thr Ala Gln Arg Thr Gly His Ala Leu
            275                 280                 285 gca gtt ggt ccg att ctg cag ggc cta aac aaa cca gtc aac gac ctt    1870
Ala Val Gly Pro Ile Leu Gln Gly Leu Asn Lys Pro Val Asn Asp Leu
290                 295                 300                 305 tcc cgt ggc gca aca gtc cct gac atc gtc aac aca gta gcc atc aca    1918
Ser Arg Gly Ala Thr Val Pro Asp Ile Val Asn Thr Val Ala Ile Thr
                310                 315                 320 gca att cag gca gga gga cgc agc ta atg gca ttg gca ctt gtt ttg     1965
Ala Ile Gln Ala Gly Gly Arg Ser     Met Ala Leu Ala Leu Val Leu
            325                         330                 335 aac tcc ggt tca tct tcc atc aaa ttc cag ctg gtc aac ccc gaa aac    2013
Asn Ser Gly Ser Ser Ser Ile Lys Phe Gln Leu Val Asn Pro Glu Asn
            340                 345                 350 tct gcc atc gac gag cca tat gtt tct ggt ctt gtg gag cag att ggt    2061
Ser Ala Ile Asp Glu Pro Tyr Val Ser Gly Leu Val Glu Gln Ile Gly
            355                 360                 365 gag cca aac ggc cgc atc gta ctc aaa ata gag ggt gaa aaa tat acc    2109
Glu Pro Asn Gly Arg Ile Val Leu Lys Ile Glu Gly Glu Lys Tyr Thr
            370                 375                 380 cta gag aca ccc atc gca gat cac tcc gaa ggc cta aac ctg gcg ttc    2157
Leu Glu Thr Pro Ile Ala Asp His Ser Glu Gly Leu Asn Leu Ala Phe
385                 390                 395                 400 gat ctc atg gac cag cac aac tgt ggt cct tcc caa ctg gaa atc acc    2205
Asp Leu Met Asp Gln His Asn Cys Gly Pro Ser Gln Leu Glu Ile Thr
                405                 410                 415 gca gtt gga cac cgc gtg gtc cac ggc gga atc ttg ttc tcc gca ccg    2253
Ala Val Gly His Arg Val Val His Gly Gly Ile Leu Phe Ser Ala Pro
            420                 425                 430 gaa ctt atc act gat gaa atc gtg gaa atg atc cgc gat ctc att cca    2301
Glu Leu Ile Thr Asp Glu Ile Val Glu Met Ile Arg Asp Leu Ile Pro
            435                 440                 445 ctc gca cca ctg cac aac cct gca aac gtt gac ggc att gat gtt gct    2349
Leu Ala Pro Leu His Asn Pro Ala Asn Val Asp Gly Ile Asp Val Ala
450                 455                 460 cga aaa att ctc ccc gat gtc cca cac gta gct gtc ttt gac acc ggt    2397
```

-continued

| | | |
|---|---|---|
| Arg Lys Ile Leu Pro Asp Val Pro His Val Ala Val Phe Asp Thr Gly<br>465                    470                  475                    480 | | |
| ttc ttc cac tca ctt cca cca gca gct gcg ctg tat gcc atc aac aag<br>Phe Phe His Ser Leu Pro Pro Ala Ala Ala Leu Tyr Ala Ile Asn Lys<br>                        485                  490                  495 | 2445 |
| gat gtc gca gct gaa cac gga atc agg cgc tat ggt ttc cac ggc acc<br>Asp Val Ala Ala Glu His Gly Ile Arg Arg Tyr Gly Phe His Gly Thr<br>                  500                    505                  510 | 2493 |
| tcc cat gaa ttt gtg tcc aag cgc gtg gtg gaa att ctg gaa aag ccc<br>Ser His Glu Phe Val Ser Lys Arg Val Val Glu Ile Leu Glu Lys Pro<br>           515                    520                  525 | 2541 |
| acc gaa gac atc aac acc atc acc ttc cac ctg ggc aac ggc gca tcc<br>Thr Glu Asp Ile Asn Thr Ile Thr Phe His Leu Gly Asn Gly Ala Ser<br>530                    535                  540 | 2589 |
| atg gct gct gtt caa ggt ggc cgt gcg gta gat act tcc atg ggt atg<br>Met Ala Ala Val Gln Gly Gly Arg Ala Val Asp Thr Ser Met Gly Met<br>545                    550                  555                  560 | 2637 |
| aca cct ctc gcg ggc ctt gtc atg ggt acc cga agc ggt gac att gat<br>Thr Pro Leu Ala Gly Leu Val Met Gly Thr Arg Ser Gly Asp Ile Asp<br>                  565                    570                  575 | 2685 |
| cca ggt atc gtc ttc cac ctt tcc cgc acc gct ggc atg agc atc gat<br>Pro Gly Ile Val Phe His Leu Ser Arg Thr Ala Gly Met Ser Ile Asp<br>                  580                    585                  590 | 2733 |
| gag atc gat aat ctg ctg aac aaa aag tcg ggt gta aag gga ctt tcc<br>Glu Ile Asp Asn Leu Leu Asn Lys Lys Ser Gly Val Lys Gly Leu Ser<br>           595                    600                  605 | 2781 |
| ggt gtt aat gat ttc cgt gaa ctg cgg gaa atg atc gac aac aat gat<br>Gly Val Asn Asp Phe Arg Glu Leu Arg Glu Met Ile Asp Asn Asn Asp<br>610                    615                  620 | 2829 |
| caa gat gcc tgg tcc gcg tac aac att tac ata cac caa ctc cgc cgc<br>Gln Asp Ala Trp Ser Ala Tyr Asn Ile Tyr Ile His Gln Leu Arg Arg<br>625                    630                  635                  640 | 2877 |
| tac ctc ggt tcc tac atg gtg gca ctg gga cgg gta gac acc atc gtg<br>Tyr Leu Gly Ser Tyr Met Val Ala Leu Gly Arg Val Asp Thr Ile Val<br>                  645                    650                  655 | 2925 |
| ttc acc gcc ggt gtc ggt gaa aat gcc cag ttt gtc cgt gag gat gcc<br>Phe Thr Ala Gly Val Gly Glu Asn Ala Gln Phe Val Arg Glu Asp Ala<br>                  660                    665                  670 | 2973 |
| ttg gca ggt ttg gaa atg tac gga att gag atc gat cca gag cgt aac<br>Leu Ala Gly Leu Glu Met Tyr Gly Ile Glu Ile Asp Pro Glu Arg Asn<br>           675                    680                  685 | 3021 |
| gca ttg cca aac gat ggt cct cga ttg att tcc acc gat gcc tcc aag<br>Ala Leu Pro Asn Asp Gly Pro Arg Leu Ile Ser Thr Asp Ala Ser Lys<br>690                    695                  700 | 3069 |
| gtg aag gtg ttt gtt att cca act aat gaa gag tta gct atc gct agg<br>Val Lys Val Phe Val Ile Pro Thr Asn Glu Glu Leu Ala Ile Ala Arg<br>705                    710                  715                  720 | 3117 |
| tac gcg gtg aag ttc gct tagctctcct ggttaggatc caccacaaat<br>Tyr Ala Val Lys Phe Ala<br>           725 | 3165 |
| cgctctgatc agcggttttg tggtggattt ttgcgttttt aagggtgaa actgcacgga | 3225 |
| tccaccacag atcccagttt tcctttggaa cgtggtggat ccttgccctg gagcttcaca | 3285 |
| ggaatcgctt gttggcccct agacctcttg gggttgcgaa ttttcgtccc caccgaacat | 3345 |
| taaaaggccg gttttggtcg aaatttgct ctaacacctt gctattatgc gaatattcgt | 3405 |
| tccatttcat cgaattccag caacccgtaa cgagaagttg aacaggaaac ctgcagtaac | 3465 |
| cccgcagaaa tcatcagc cccaattgtc caaaagtaa ctcccccaga atcgcttcta | 3525 |
| agggcctaac tcgcccaaag tcaaactagg ggacatcgca ctcctaaagg cccttaaatc | 3585 |

```
gccacctacc aaatagcccc aagtcaaaac agctagaacc aactcagtgg ccgcacggca   3645
ttcgccatat ccacaagtgc gtaacggtgg tgcgggaacg gtgcagaacg tgcctgaatg   3705
cggagtgcct cggagatgcc ggtgcgcagg ccttttgggg agaacgggta ttcaaacaaa   3765
gggttcgcgg aggcggaagc tttgagtttt cgctctcgaa gccagctgag gcctgccgac   3825
atgatggcaa ttttgatttg gttgaagcgg ggttcgtttg tggggatttc ggtgagtcgg   3885
cgggcagccc gtcggatgcg ggattcactc aaattggagc tgaccagcaa caagatggtg   3945
gtgagggtgg ccattcggta gtgggtggat gattgggga gtttgtctag ggcttggact   4005
gcgagttcga tttggttttc ggccatgagt tggcgggcga cccgaacgc ggaggacacg   4065 gtggtggggt tggttgccca gacaagtgcg tagaggcgca gtgaatggaa gcggactacg   4125
tgtgggtcgc tggagatgtg ggaccaggtg tcgctgagtg attcgaaggc ggaggcgtcg   4185
aggtcttcga aatct                                                    4200
```

<210> SEQ ID NO 40
<211> LENGTH: 329
<212> TYPE: PRT
<213> ORGANISM: Corynebacterium glutamicum

<400> SEQUENCE: 40

```
Met Ser Ala Glu Leu Phe Glu Asn Trp Leu Leu Lys Arg Ala Arg Ala
  1               5                  10                  15

Glu His Ser His Ile Val Leu Pro Glu Gly Asp Asp Arg Ile Leu
                 20                  25                  30

Met Ala Ala His Gln Leu Leu Asp Gln Asp Ile Cys Asp Ile Thr Ile
             35                  40                  45

Leu Gly Asp Pro Val Lys Ile Lys Glu Arg Ala Thr Glu Leu Gly Leu
         50                  55                  60

His Leu Asn Thr Ala Tyr Leu Val Asn Pro Leu Thr Asp Pro Arg Leu
 65                  70                  75                  80

Glu Glu Phe Ala Glu Gln Phe Ala Glu Leu Arg Lys Ser Lys Ser Val
                 85                  90                  95

Thr Ile Asp Glu Ala Arg Glu Ile Met Lys Asp Ile Ser Tyr Phe Gly
                100                 105                 110

Thr Met Met Val His Asn Gly Asp Ala Asp Gly Met Val Ser Gly Ala
            115                 120                 125

Ala Asn Thr Thr Ala His Thr Ile Lys Pro Ser Phe Gln Ile Ile Lys
        130                 135                 140

Thr Val Pro Glu Ala Ser Val Val Ser Ser Ile Phe Leu Met Val Leu
145                 150                 155                 160

Arg Gly Arg Leu Trp Ala Phe Gly Asp Cys Ala Val Asn Pro Asn Pro
                165                 170                 175

Thr Ala Glu Gln Leu Gly Glu Ile Ala Val Val Ser Ala Lys Thr Ala
            180                 185                 190

Ala Gln Phe Gly Ile Asp Pro Arg Val Ala Ile Leu Ser Tyr Ser Thr
        195                 200                 205

Gly Asn Ser Gly Gly Gly Ser Asp Val Asp Arg Ala Ile Asp Ala Leu
    210                 215                 220

Ala Glu Ala Arg Arg Leu Asn Pro Glu Leu Cys Val Asp Gly Pro Leu
225                 230                 235                 240

Gln Phe Asp Ala Ala Val Asp Pro Gly Val Ala Arg Lys Lys Met Pro
                245                 250                 255

Asp Ser Asp Val Ala Gly Gln Ala Asn Val Phe Ile Phe Pro Asp Leu
```

```
                    260                 265                 270
Glu Ala Gly Asn Ile Gly Tyr Lys Thr Ala Gln Arg Thr Gly His Ala
            275                 280                 285
Leu Ala Val Gly Pro Ile Leu Gln Gly Leu Asn Lys Pro Val Asn Asp
            290                 295                 300
Leu Ser Arg Gly Ala Thr Val Pro Asp Ile Val Asn Thr Val Ala Ile
305                 310                 315                 320
Thr Ala Ile Gln Ala Gly Gly Arg Ser
                325

<210> SEQ ID NO 41
<211> LENGTH: 397
<212> TYPE: PRT
<213> ORGANISM: Corynebacterium glutamicum

<400> SEQUENCE: 41

Met Ala Leu Ala Leu Val Leu Asn Ser Gly Ser Ser Ile Lys Phe
1               5                   10                  15
Gln Leu Val Asn Pro Glu Asn Ser Ala Ile Asp Glu Pro Tyr Val Ser
                20                  25                  30
Gly Leu Val Glu Gln Ile Gly Glu Pro Asn Gly Arg Ile Val Leu Lys
            35                  40                  45
Ile Glu Gly Glu Lys Tyr Thr Leu Glu Thr Pro Ile Ala Asp His Ser
        50                  55                  60
Glu Gly Leu Asn Leu Ala Phe Asp Leu Met Asp Gln His Asn Cys Gly
65                  70                  75                  80
Pro Ser Gln Leu Glu Ile Thr Ala Val Gly His Arg Val His Gly
                85                  90                  95
Gly Ile Leu Phe Ser Ala Pro Glu Leu Ile Thr Asp Glu Ile Val Glu
                100                 105                 110
Met Ile Arg Asp Leu Ile Pro Leu Ala Pro Leu His Asn Pro Ala Asn
            115                 120                 125
Val Asp Gly Ile Asp Val Ala Arg Lys Ile Leu Pro Asp Val Pro His
        130                 135                 140
Val Ala Val Phe Asp Thr Gly Phe Phe His Ser Leu Pro Pro Ala Ala
145                 150                 155                 160
Ala Leu Tyr Ala Ile Asn Lys Asp Val Ala Ala Glu His Gly Ile Arg
                165                 170                 175
Arg Tyr Gly Phe His Gly Thr Ser His Glu Phe Val Ser Lys Arg Val
            180                 185                 190
Val Glu Ile Leu Glu Lys Pro Thr Glu Asp Ile Asn Thr Ile Thr Phe
        195                 200                 205
His Leu Gly Asn Gly Ala Ser Met Ala Ala Val Gln Gly Gly Arg Ala
    210                 215                 220
Val Asp Thr Ser Met Gly Met Thr Pro Leu Ala Gly Leu Val Met Gly
225                 230                 235                 240
Thr Arg Ser Gly Asp Ile Asp Pro Gly Ile Val Phe His Leu Ser Arg
                245                 250                 255
Thr Ala Gly Met Ser Ile Asp Glu Ile Asp Asn Leu Leu Asn Lys Lys
            260                 265                 270
Ser Gly Val Lys Gly Leu Ser Gly Val Asn Asp Phe Arg Glu Leu Arg
        275                 280                 285
Glu Met Ile Asp Asn Asn Asp Gln Asp Ala Trp Ser Ala Tyr Asn Ile
    290                 295                 300
Tyr Ile His Gln Leu Arg Arg Tyr Leu Gly Ser Tyr Met Val Ala Leu
```

```
                305                 310                 315                 320
Gly Arg Val Asp Thr Ile Val Phe Thr Ala Gly Val Gly Glu Asn Ala
                325                 330                 335
Gln Phe Val Arg Glu Asp Ala Leu Ala Gly Leu Glu Met Tyr Gly Ile
                340                 345                 350
Glu Ile Asp Pro Glu Arg Asn Ala Leu Pro Asn Asp Gly Pro Arg Leu
                355                 360                 365
Ile Ser Thr Asp Ala Ser Lys Val Lys Val Phe Val Ile Pro Thr Asn
                370                 375                 380
Glu Glu Leu Ala Ile Ala Arg Tyr Ala Val Lys Phe Ala
385                 390                 395

<210> SEQ ID NO 42
<211> LENGTH: 3780
<212> TYPE: DNA
<213> ORGANISM: Corynebacterium glutamicum
<220> FEATURE:
<221> NAME/KEY: CDS
<222> LOCATION: (996)..(2732)

<400> SEQUENCE: 42
```

| | | |
|---|---|---|
| taatgaggaa aaccgaaccc caccagaaga attccaacag cgcaccacca atgatcgggc | 60 |
| ctgccgcagc gccaagaatt gccacggaac cccaaatacc aattgcagtg ttgcgctcac | 120 |
| gctcatcctc aaacgtaatg cggatcagag ccaaggttgc aggcatcatc gttgccgcac | 180 |
| cgatgccaag gaaagctctc gcagcaacaa gagcccacgc agttggagca aacgcagcac | 240 |
| caagtgaagc gattccgaaa atgctcaagc ccatgaggaa catccggcgg tggccgattt | 300 |
| tgtcacccaa agtgccggta cccaaaagaa ggcccgccat gagcagggga tatgcgttga | 360 |
| tgatccacaa cgcttgggtt tcggtggctg cgagctgttc acgcagcaga gggagtgcgg | 420 |
| tgtagagaat cgagttgtct acaccgatca gaaagagacc accgctgata acggcgagga | 480 |
| aagcccaacg ttgggttttc gtaggcgctt gcgcctgtaa ggtttctgaa gtcatggatc | 540 |
| gtaactgtaa cgaatggtcg gtacagttac aactctttg ttggtgtttt agaccacggc | 600 |
| gctgtgtggc gatttaagac gtcggaaatc gtaggggact gtcagcgtgg gtcgggttct | 660 |
| ttgaggcgct tagaggcgat tctgtgaggt cactttttgt ggggtcgggg tctaaatttg | 720 |
| gccagttttc gaggcgacca gacaggcgtg cccacgatgt ttaaataggc gatcggtggg | 780 |
| catctgtgtt tggtttcgac gggctgaaac caaaccagac tgcccagcaa cgacggaaat | 840 |
| cccaaaagtg ggcatccctg tttggtaccg agtaccacc cgggcctgaa actccctggc | 900 |
| aggcgggcga agcgtggcaa caactggaat ttaagagcac aattgaagtc gcaccaagtt | 960 |
| aggcaacaca atagccataa cgttgaggag ttcag atg gca cac agc tac gca | 1013 |
|                                        Met Ala His Ser Tyr Ala | |
|                                         1               5 | |
| gaa caa tta att gac act ttg gaa gct caa ggt gtg aag cga att tat | 1061 |
| Glu Gln Leu Ile Asp Thr Leu Glu Ala Gln Gly Val Lys Arg Ile Tyr | |
|          10                  15                  20 | |
| ggt ttg gtg ggt gac agc ctt aat ccg atc gtg gat gct gtc cgc caa | 1109 |
| Gly Leu Val Gly Asp Ser Leu Asn Pro Ile Val Asp Ala Val Arg Gln | |
|          25                  30                  35 | |
| tca gat att gag tgg gtg cac gtt cga aat gag gaa gcg gcg gcg ttt | 1157 |
| Ser Asp Ile Glu Trp Val His Val Arg Asn Glu Glu Ala Ala Ala Phe | |
|          40                  45                  50 | |
| gca gcc ggt gcg gaa tcg ttg atc act ggg gag ctg gca gta tgt gct | 1205 |
| Ala Ala Gly Ala Glu Ser Leu Ile Thr Gly Glu Leu Ala Val Cys Ala | |
| 55                  60                  65                  70 | |

| | | | | | | | | | | | | | | | |
|---|---|---|---|---|---|---|---|---|---|---|---|---|---|---|---|
| gct | tct | tgt | ggt | cct | gga | aac | aca | cac | ctg | att | cag | ggt | ctt | tat | gat | 1253
| Ala | Ser | Cys | Gly | Pro | Gly | Asn | Thr | His | Leu | Ile | Gln | Gly | Leu | Tyr | Asp |
| | | | 75 | | | | | 80 | | | | | 85 | | |

```
gct tct tgt ggt cct gga aac aca cac ctg att cag ggt ctt tat gat      1253
Ala Ser Cys Gly Pro Gly Asn Thr His Leu Ile Gln Gly Leu Tyr Asp
            75                  80                  85 tcg cat cga aat ggt gcg aag gtg ttg gcc atc gct agc cat att ccg      1301
Ser His Arg Asn Gly Ala Lys Val Leu Ala Ile Ala Ser His Ile Pro
            90                  95                 100 agt gcc cag att ggt tcg acg ttc ttc cag gaa acg cat ccg gag att      1349
Ser Ala Gln Ile Gly Ser Thr Phe Phe Gln Glu Thr His Pro Glu Ile
           105                 110                 115 ttg ttt aag gaa tgc tct ggt tac tgc gag atg gtg aat ggt ggt gag      1397
Leu Phe Lys Glu Cys Ser Gly Tyr Cys Glu Met Val Asn Gly Gly Glu
120                 125                 130 cag ggt gaa cgc att ttg cat cac gcg att cag tcc acc atg gcg ggt      1445
Gln Gly Glu Arg Ile Leu His His Ala Ile Gln Ser Thr Met Ala Gly
135                 140                 145                 150 aaa ggt gtg tcg gtg gta gtg att cct ggt gat atc gct aag gaa gac      1493
Lys Gly Val Ser Val Val Val Ile Pro Gly Asp Ile Ala Lys Glu Asp
                155                 160                 165 gca ggt gac ggt act tat tcc aat tcc act att tct tct ggc act cct      1541
Ala Gly Asp Gly Thr Tyr Ser Asn Ser Thr Ile Ser Ser Gly Thr Pro
                170                 175                 180 gtg gtg ttc ccg gat cct act gag gct gca gcg ctg gtg gag gcg att      1589
Val Val Phe Pro Asp Pro Thr Glu Ala Ala Ala Leu Val Glu Ala Ile
            185                 190                 195 aac aac gct aag tct gtc act ttg ttc tgc ggt gcg ggc gtg aag aat      1637
Asn Asn Ala Lys Ser Val Thr Leu Phe Cys Gly Ala Gly Val Lys Asn
            200                 205                 210 gct cgc gcg cag gtg ttg gag ttg gcg gag aag att aaa tca ccg atc      1685
Ala Arg Ala Gln Val Leu Glu Leu Ala Glu Lys Ile Lys Ser Pro Ile
215                 220                 225                 230 ggg cat gcg ctg ggt ggt aag cag tac atc cag cat gag aat ccg ttt      1733
Gly His Ala Leu Gly Gly Lys Gln Tyr Ile Gln His Glu Asn Pro Phe
                235                 240                 245 gag gtc ggc atg tct ggc ctg ctt ggt tac ggc gcc tgc gtg gat gcg      1781
Glu Val Gly Met Ser Gly Leu Leu Gly Tyr Gly Ala Cys Val Asp Ala
            250                 255                 260 tcc aat gag gcg gat ctg ctg att cta ttg ggt acg gat ttc cct tat      1829
Ser Asn Glu Ala Asp Leu Leu Ile Leu Leu Gly Thr Asp Phe Pro Tyr
            265                 270                 275 tct gat ttc ctt cct aaa gac aac gtt gcc cag gtg gat atc aac ggt      1877
Ser Asp Phe Leu Pro Lys Asp Asn Val Ala Gln Val Asp Ile Asn Gly
280                 285                 290 gcg cac att ggt cga cgt acc acg gtg aag tat ccg gtg acc ggt gat      1925
Ala His Ile Gly Arg Arg Thr Thr Val Lys Tyr Pro Val Thr Gly Asp
295                 300                 305                 310 gtt gct gca aca atc gaa aat att ttg cct cat gtg aag gaa aaa aca      1973
Val Ala Ala Thr Ile Glu Asn Ile Leu Pro His Val Lys Glu Lys Thr
                315                 320                 325 gat cgt tcc ttc ctt gat cgg atg ctc aag gca cac gag cgt aag ttg      2021
Asp Arg Ser Phe Leu Asp Arg Met Leu Lys Ala His Glu Arg Lys Leu
            330                 335                 340 agc tcg gtg gta gag acg tac aca cat aac gtc gag aag cat gtg cct      2069
Ser Ser Val Val Glu Thr Tyr Thr His Asn Val Glu Lys His Val Pro
            345                 350                 355 att cac cct gaa tac gtt gcc tct att ttg aac gag ctg gcc gat aag      2117
Ile His Pro Glu Tyr Val Ala Ser Ile Leu Asn Glu Leu Ala Asp Lys
            360                 365                 370 gat gcg gtg ttt act gtg gat acc ggc atg tgc aat gtg tgg cat gcg      2165
Asp Ala Val Phe Thr Val Asp Thr Gly Met Cys Asn Val Trp His Ala
375                 380                 385                 390
```

-continued

| | | |
|---|---|---|
| agg tac atc gag aat ccg gag gga acg cgc gac ttt gtg ggt tca ttc<br>Arg Tyr Ile Glu Asn Pro Glu Gly Thr Arg Asp Phe Val Gly Ser Phe<br>395 400 405 | 2213 | |
| cgc cac ggc acg atg gct aat gcg ttg cct cat gcg att ggt gcg caa<br>Arg His Gly Thr Met Ala Asn Ala Leu Pro His Ala Ile Gly Ala Gln<br>410 415 420 | 2261 | |
| agt gtt gat cga aac cgc cag gtg atc gcg atg tgt ggc gat ggt ggt<br>Ser Val Asp Arg Asn Arg Gln Val Ile Ala Met Cys Gly Asp Gly Gly<br>425 430 435 | 2309 | |
| ttg ggc atg ctg ctg ggt gag ctt ctg acc gtt aag ctg cac caa ctt<br>Leu Gly Met Leu Leu Gly Glu Leu Leu Thr Val Lys Leu His Gln Leu<br>440 445 450 | 2357 | |
| ccg ctg aag gct gtg gtg ttt aac aac agt tct ttg ggc atg gtg aag<br>Pro Leu Lys Ala Val Val Phe Asn Asn Ser Ser Leu Gly Met Val Lys<br>455 460 465 470 | 2405 | |
| ttg gag atg ctc gtg gag gga cag cca gaa ttt ggt act gac cat gag<br>Leu Glu Met Leu Val Glu Gly Gln Pro Glu Phe Gly Thr Asp His Glu<br>475 480 485 | 2453 | |
| gaa gtg aat ttc gca gag att gcg gcg gct gcg ggt atc aaa tcg gta<br>Glu Val Asn Phe Ala Glu Ile Ala Ala Ala Ala Gly Ile Lys Ser Val<br>490 495 500 | 2501 | |
| cgc atc acc gat ccg aag aaa gtt cgc gag cag cta gct gag gca ttg<br>Arg Ile Thr Asp Pro Lys Lys Val Arg Glu Gln Leu Ala Glu Ala Leu<br>505 510 515 | 2549 | |
| gca tat cct gga cct gta ctg atc gat atc gtc acg gat cct aat gcg<br>Ala Tyr Pro Gly Pro Val Leu Ile Asp Ile Val Thr Asp Pro Asn Ala<br>520 525 530 | 2597 | |
| ctg tcg atc cca cca acc atc acg tgg gaa cag gtc atg gga ttc agc<br>Leu Ser Ile Pro Pro Thr Ile Thr Trp Glu Gln Val Met Gly Phe Ser<br>535 540 545 550 | 2645 | |
| aag gcg gcc acc cga acc gtc ttt ggt gga gga gta gga gcg atg atc<br>Lys Ala Ala Thr Arg Thr Val Phe Gly Gly Gly Val Gly Ala Met Ile<br>555 560 565 | 2693 | |
| gat ctg gcc cgt tcg aac ata agg aat att cct act cca tgatgattga<br>Asp Leu Ala Arg Ser Asn Ile Arg Asn Ile Pro Thr Pro<br>570 575 | 2742 | |
| tacacctgct gttctcattg accgcgagcg cttaactgcc aacatttcca ggatggcagc | 2802 | |
| tcacgccggt gcccatgaga ttgccctgcg tccgcatgtg aaaacgcaca aaatcattga | 2862 | |
| aattgcgcag atgcaggtcg acgccggtgc ccgaggatc acctgcgcaa ccattggcga | 2922 | |
| ggcggaaatt tttgccggcg caggttttac ggacatcttt attgcatatc cgctgtatct | 2982 | |
| aaccgatcat gcagtgcaac gcctgaacgc gatccccgga gaaatttcca ttggcgtgga | 3042 | |
| ttcggtagag atggcacagg cgacggcggg tttgcgggaa gatatcaagg ctctgattga | 3102 | |
| agtggattcg ggacatcgta gaagtggagt cacggcgact gcttcagaat tgagtcagat | 3162 | |
| ccgcgaggcg ctgggcagca ggtatgcagg agtgtttact tttcctgggc attcttatgg | 3222 | |
| cccgggaaat ggtgagcagg cagcagctga tgagcttcag gctctaaaca acagcgtcca | 3282 | |
| gcgacttgct ggcggcctga cttctggcgg ttcctcgccg tctgcgcagt tacagacgc | 3342 | |
| aatcgatgag atgcgaccag gcgtgtatgt gtttaacgat tcccagcaga tcacctcggg | 3402 | |
| agcatgcact gagaagcagg tggcaatgac ggtgctgtct actgtggtca gccgaaatgt | 3462 | |
| gtcagatcgc cggatcattt tggatgcggg atccaaaatc ctcagcactg ataaaccagc | 3522 | |
| atggattgat ggcaatggtt tgttctggg gaatcctgaa gcccgaatct ctgctttgtc | 3582 | |
| ggagcatcac gcaaccattt tctggccaga taaagtgcta cttccagtaa tcggggagca | 3642 | |
| gctcaacatc gtgcccaacc atgcctgcaa cgtgattaat ttggtggatg aggtctacgt | 3702 | |

```
tcgggaagcc gatggcactt tccgtacctg gaaggtagtt gcccgcggca gaaacaatta    3762
gggaaacctc ttgacctt                                                   3780
```

<210> SEQ ID NO 43
<211> LENGTH: 579
<212> TYPE: PRT
<213> ORGANISM: Corynebacterium glutamicum

<400> SEQUENCE: 43

```
Met Ala His Ser Tyr Ala Glu Gln Leu Ile Asp Thr Leu Glu Ala Gln
  1               5                  10                  15

Gly Val Lys Arg Ile Tyr Gly Leu Val Gly Asp Ser Leu Asn Pro Ile
             20                  25                  30

Val Asp Ala Val Arg Gln Ser Asp Ile Glu Trp Val His Val Arg Asn
         35                  40                  45

Glu Glu Ala Ala Ala Phe Ala Ala Gly Ala Glu Ser Leu Ile Thr Gly
     50                  55                  60

Glu Leu Ala Val Cys Ala Ala Ser Cys Gly Pro Gly Asn Thr His Leu
 65                  70                  75                  80

Ile Gln Gly Leu Tyr Asp Ser His Arg Asn Gly Ala Lys Val Leu Ala
                 85                  90                  95

Ile Ala Ser His Ile Pro Ser Ala Gln Ile Gly Ser Thr Phe Phe Gln
            100                 105                 110

Glu Thr His Pro Glu Ile Leu Phe Lys Glu Cys Ser Gly Tyr Cys Glu
        115                 120                 125

Met Val Asn Gly Gly Glu Gln Gly Glu Arg Ile Leu His His Ala Ile
    130                 135                 140

Gln Ser Thr Met Ala Gly Lys Gly Val Ser Val Val Ile Pro Gly
145                 150                 155                 160

Asp Ile Ala Lys Glu Asp Ala Gly Asp Gly Thr Tyr Ser Asn Ser Thr
                165                 170                 175

Ile Ser Ser Gly Thr Pro Val Val Phe Pro Asp Pro Thr Glu Ala Ala
            180                 185                 190

Ala Leu Val Glu Ala Ile Asn Asn Ala Lys Ser Val Thr Leu Phe Cys
        195                 200                 205

Gly Ala Gly Val Lys Asn Ala Arg Ala Gln Val Leu Glu Leu Ala Glu
    210                 215                 220

Lys Ile Lys Ser Pro Ile Gly His Ala Leu Gly Gly Lys Gln Tyr Ile
225                 230                 235                 240

Gln His Glu Asn Pro Phe Glu Val Gly Met Ser Gly Leu Leu Gly Tyr
                245                 250                 255

Gly Ala Cys Val Asp Ala Ser Asn Glu Ala Asp Leu Leu Ile Leu Leu
            260                 265                 270

Gly Thr Asp Phe Pro Tyr Ser Asp Phe Leu Pro Lys Asp Asn Val Ala
        275                 280                 285

Gln Val Asp Ile Asn Gly Ala His Ile Gly Arg Arg Thr Thr Val Lys
    290                 295                 300

Tyr Pro Val Thr Gly Asp Val Ala Ala Thr Ile Glu Asn Ile Leu Pro
305                 310                 315                 320

His Val Lys Glu Lys Thr Asp Arg Ser Phe Leu Asp Arg Met Leu Lys
                325                 330                 335

Ala His Glu Arg Lys Leu Ser Ser Val Val Glu Thr Tyr Thr His Asn
            340                 345                 350

Val Glu Lys His Val Pro Ile His Pro Glu Tyr Val Ala Ser Ile Leu
        355                 360                 365
```

```
Asn Glu Leu Ala Asp Lys Asp Ala Val Phe Thr Val Asp Thr Gly Met
    370                 375                 380

Cys Asn Val Trp His Ala Arg Tyr Ile Glu Asn Pro Glu Gly Thr Arg
385                 390                 395                 400

Asp Phe Val Gly Ser Phe Arg His Gly Thr Met Ala Asn Ala Leu Pro
                405                 410                 415

His Ala Ile Gly Ala Gln Ser Val Asp Arg Asn Arg Gln Val Ile Ala
            420                 425                 430

Met Cys Gly Asp Gly Gly Leu Gly Met Leu Leu Gly Glu Leu Leu Thr
        435                 440                 445

Val Lys Leu His Gln Leu Pro Leu Lys Ala Val Val Phe Asn Asn Ser
    450                 455                 460

Ser Leu Gly Met Val Lys Leu Glu Met Leu Val Glu Gly Gln Pro Glu
465                 470                 475                 480

Phe Gly Thr Asp His Glu Glu Val Asn Phe Ala Glu Ile Ala Ala Ala
                485                 490                 495

Ala Gly Ile Lys Ser Val Arg Ile Thr Asp Pro Lys Lys Val Arg Glu
            500                 505                 510

Gln Leu Ala Glu Ala Leu Ala Tyr Pro Gly Pro Val Leu Ile Asp Ile
        515                 520                 525

Val Thr Asp Pro Asn Ala Leu Ser Ile Pro Pro Thr Ile Thr Trp Glu
    530                 535                 540

Gln Val Met Gly Phe Ser Lys Ala Ala Thr Arg Thr Val Phe Gly Gly
545                 550                 555                 560

Gly Val Gly Ala Met Ile Asp Leu Ala Arg Ser Asn Ile Arg Asn Ile
                565                 570                 575

Pro Thr Pro

<210> SEQ ID NO 44
<211> LENGTH: 3600
<212> TYPE: DNA
<213> ORGANISM: Corynebacterium glutamicum
<220> FEATURE:
<221> NAME/KEY: CDS
<222> LOCATION: (1037)..(2542)

<400> SEQUENCE: 44
gaagcgctac ggacttcgcg ccggcgtcga cagcaatgcg tccagcatcc aagtgagtat     60
ggtgctcatc atcaatacca acgcggaact tcaccgtcac cggaatgtcc gtgccttccg    120
tagccttcac agccgcggaa acgatgtttt caaacaaacg gcgcttgtaa ggaatcgcag    180
aaccgccacc ccggcgcgtg acctttggaa ccgggcagcc aaagttcata tcaatatgat    240
ccgccaagtt ttcatcaacg atcatcttcg ccgcttcgta ggtgtacttc gggtcaaccg    300
tgtacagctg caagcttcgg ggattttcat ccggcgcgaa ggtggtcatg tgcatggttt    360
tctcattgcg ctcaacaaga gcacgcgcag tcaccatttc acagacgtac agccccgaga    420
ttgttcccgt gcgttgcatt tcctgttcac ggcacagcgt gcggaaagca acgttggtta    480
caccagccat gggggctaga accacagggg aggcaaggtc aaaggggccg attttttaaag   540 tcacctaact attgtccccc gtgaatcagg ttgggcaaaa tatttgaagc aaattgtgag    600
cagggcgcaa ctaggaaagt ggtgtgcttt cacttttttgg gggctggggt tgggttaagc    660
ttcgcgggct ctaggttgg tctgagcttt attcctgggc tttgggaggc ttgcaaacag     720
ggggcatgca aatttggggg taatgctggg ccttgaaatc ccactatcac agatagtatt    780
cgggcatttc ctgtcacgat ggtttatcct tgggacacaa catcaaagtg gggtacatca    840
```

```
tatgcttccg gttgaagtga cctatctgaa aagattggtc gaaccttgaa gcaatggtgt      900
gaactgcgtt aacgaatttt gtcggacgtt aaaatggtcg cattctgctt gctgaagtgg      960
cacacctatg tgttctgctt gggtatagca gtgcgggaaa aatttgaaaa agtccgatta     1020
cctgaggagg tattca atg tct gat cgc att gct tca gaa aag ctg cgc tcc    1072
               Met Ser Asp Arg Ile Ala Ser Glu Lys Leu Arg Ser
                 1               5                  10 aag ctc atg tcc gcc gac gag gcg gca cag ttt gtt aac cac ggt gac      1120
Lys Leu Met Ser Ala Asp Glu Ala Ala Gln Phe Val Asn His Gly Asp
         15                  20                  25 aag gtt ggt ttc tcc ggc ttc acc ggc gct ggc tac cca aag gca ctg      1168
Lys Val Gly Phe Ser Gly Phe Thr Gly Ala Gly Tyr Pro Lys Ala Leu
 30                  35                  40 cct acg gca atc gct aac cgg gct aaa gaa gca cac ggt gca ggc aac      1216
Pro Thr Ala Ile Ala Asn Arg Ala Lys Glu Ala His Gly Ala Gly Asn
 45                  50                  55                  60 gac tac gca atc gac ctg ttc act ggc gca tcg acc gcc cct gac tgc      1264
Asp Tyr Ala Ile Asp Leu Phe Thr Gly Ala Ser Thr Ala Pro Asp Cys
             65                  70                  75 gat ggc gta ctt gca gaa gct gac gct atc cgc tgg cgc atg cca tac      1312
Asp Gly Val Leu Ala Glu Ala Asp Ala Ile Arg Trp Arg Met Pro Tyr
                 80                  85                  90 gca tct gat cca atc atg cgt aac aag atc aac tcc ggc tcc atg gga      1360
Ala Ser Asp Pro Ile Met Arg Asn Lys Ile Asn Ser Gly Ser Met Gly
             95                 100                 105 tac tcc gat atc cac ctg tcc cac tcc ggc cag cag gtt gaa gag ggc      1408
Tyr Ser Asp Ile His Leu Ser His Ser Gly Gln Gln Val Glu Glu Gly
110                 115                 120 ttc ttc ggc cag ctc aac gta gct gtc att gaa atc acc cgc atc act      1456
Phe Phe Gly Gln Leu Asn Val Ala Val Ile Glu Ile Thr Arg Ile Thr
125                 130                 135                 140 gaa gag ggc tac atc atc cct tct tcc tcc gtg ggt aac aac gtt gag      1504
Glu Glu Gly Tyr Ile Ile Pro Ser Ser Ser Val Gly Asn Asn Val Glu
                145                 150                 155 tgg ctc aac gct gca gag aag gtc atc ctc gag gtt aac tct tgg cag      1552
Trp Leu Asn Ala Ala Glu Lys Val Ile Leu Glu Val Asn Ser Trp Gln
            160                 165                 170 tct gaa gac ctc gaa ggt atg cac gac atc tgg tct gtt cct gcc ctg      1600
Ser Glu Asp Leu Glu Gly Met His Asp Ile Trp Ser Val Pro Ala Leu
        175                 180                 185 cca aac cgc att gcc gtg cca atc aac aag cca ggc gac cgc atc ggt      1648
Pro Asn Arg Ile Ala Val Pro Ile Asn Lys Pro Gly Asp Arg Ile Gly
    190                 195                 200 aag acc tac atc gag ttc gac acc gac aag gtt gtt gct gtt gtt gag      1696
Lys Thr Tyr Ile Glu Phe Asp Thr Asp Lys Val Val Ala Val Val Glu
205                 210                 215                 220 acc aac acc gca gac cgc aac gca cca ttc aag cct gtc gac gac atc      1744
Thr Asn Thr Ala Asp Arg Asn Ala Pro Phe Lys Pro Val Asp Asp Ile
                225                 230                 235 tct aag aag atc gct ggc aac ttc ctc gac ttc ctg gaa agc gaa gtt      1792
Ser Lys Lys Ile Ala Gly Asn Phe Leu Asp Phe Leu Glu Ser Glu Val
            240                 245                 250 gct gca ggt cgc ctg tcc tac gac ggc tac atc atg cag tcc ggc gtg      1840
Ala Ala Gly Arg Leu Ser Tyr Asp Gly Tyr Ile Met Gln Ser Gly Val
        255                 260                 265 ggc aac gtg cca aac gcg gtg atg gca ggc ctg ctg gaa tcc aag ttt      1888
Gly Asn Val Pro Asn Ala Val Met Ala Gly Leu Leu Glu Ser Lys Phe
    270                 275                 280 gag aac atc cag gcc tac acc gaa gtt atc cag gac ggc atg gtg gac      1936
Glu Asn Ile Gln Ala Tyr Thr Glu Val Ile Gln Asp Gly Met Val Asp
```

-continued

| | | |
|---|---|---|
| Glu Asn Ile Gln Ala Tyr Thr Glu Val Ile Gln Asp Gly Met Val Asp<br>285                         290                    295                    300 | | |
| ctc atc gac gcc ggc aag atg acc gtt gca tcc gca act tcc ttc tcc<br>Leu Ile Asp Ala Gly Lys Met Thr Val Ala Ser Ala Thr Ser Phe Ser<br>                    305                    310                    315 | 1984 | |
| ctg tct cct gag tac gca gag aag atg aac aac gag gct aag cgt tac<br>Leu Ser Pro Glu Tyr Ala Glu Lys Met Asn Asn Glu Ala Lys Arg Tyr<br>                320                    325                    330 | 2032 | |
| cgc gag tcc att atc ctg cgc cca cag cag atc tct aac cac cca gag<br>Arg Glu Ser Ile Ile Leu Arg Pro Gln Gln Ile Ser Asn His Pro Glu<br>          335                    340                    345 | 2080 | |
| gtc atc cgc cgc gtt ggc ctg atc gcc acc aac ggt ctc atc gag gct<br>Val Ile Arg Arg Val Gly Leu Ile Ala Thr Asn Gly Leu Ile Glu Ala<br>350                         355                    360 | 2128 | |
| gac att tac ggc aac gtc aac tcc acc aac gtt tct ggc tcc cgc gtc<br>Asp Ile Tyr Gly Asn Val Asn Ser Thr Asn Val Ser Gly Ser Arg Val<br>365                        370                    375                    380 | 2176 | |
| atg aac ggc atc ggc ggc tcc ggc gac ttc acc cgt aac ggc tac atc<br>Met Asn Gly Ile Gly Gly Ser Gly Asp Phe Thr Arg Asn Gly Tyr Ile<br>                    385                    390                    395 | 2224 | |
| tcc agc ttc atc acc cct tca gag gca aag ggc ggc gca atc tct gcg<br>Ser Ser Phe Ile Thr Pro Ser Glu Ala Lys Gly Gly Ala Ile Ser Ala<br>                    400                    405                    410 | 2272 | |
| atc gtt cct ttc gca tcc cac atc gac cac acc gag cac gat gtc atg<br>Ile Val Pro Phe Ala Ser His Ile Asp His Thr Glu His Asp Val Met<br>          415                    420                    425 | 2320 | |
| gtt gtt atc tct gag tac ggt tac gca gac ctt cgt ggt ctg gct cca<br>Val Val Ile Ser Glu Tyr Gly Tyr Ala Asp Leu Arg Gly Leu Ala Pro<br>430                         435                    440 | 2368 | |
| cgt gag cgc gtt gcc aag atg atc ggc ctg gct cac cct gat tac cgc<br>Arg Glu Arg Val Ala Lys Met Ile Gly Leu Ala His Pro Asp Tyr Arg<br>445                       450                    455                    460 | 2416 | |
| cca ctg ctc gag gag tac tac gct cgc gca acc tcc ggt gac aac aag<br>Pro Leu Leu Glu Glu Tyr Tyr Ala Arg Ala Thr Ser Gly Asp Asn Lys<br>                    465                    470                    475 | 2464 | |
| tac atg cag acc cct cat gat ctt gca acc gcg ttt gat ttc cac atc<br>Tyr Met Gln Thr Pro His Asp Leu Ala Thr Ala Phe Asp Phe His Ile<br>                    480                    485                    490 | 2512 | |
| aac ctg gct aag aac ggc tcc atg aag gca taagttttt cttggtttag<br>Asn Leu Ala Lys Asn Gly Ser Met Lys Ala<br>          495                    500 | 2562 | |
| aaaccgccgc ctcgacaaca tttcgaggcg gcggtttctt ttattacctg ggttttgagc | 2622 | |
| gttaaattag accaggtcag gctagtgttt ggtagctaat tgagggcgat tttaataagg | 2682 | |
| ccggtgccat gtactaatat ggtctgagtt gggcctatag ctcagttggt agagctacgg | 2742 | |
| actttaatc cgcaggtctt gggttcgagt cccaatgggc ccacatctta agtacccctg | 2802 | |
| ttttggagaa tgctccgagc caggggtact tttcttttcc tcacacacag tagctgctga | 2862 | |
| gaaaaatgaa gacctttgt taggttggga gtatgaccaa cccatacgag gccttcatac | 2922 | |
| cgctcaagca tcgtacgggg attgaacccg agcacacctt ttgggaatgg gaaaacaaaa | 2982 | |
| gggttcacat tgcaaggaga cgtcgagaag cgcccgtccg cgttatcgtg gtgcatgggc | 3042 | |
| taggcaccca tagtggcgcc ctctggcccc tcgtcgcggc cattgagggc gcggacctcg | 3102 | |
| ccgcgatcga cctgcctaaa actccgcttt acgacgattg ctgcgccctt ttagaatctt | 3162 | |
| tcatctcttc cgaagacgac ggtcggccac tcatcctgat cggtgcaggc accggaggct | 3222 | |
| tgctttgcgc agaagctgca caccgcacag gactggtcgc acacgtcatt gccacctgcc | 3282 | |
| tgctcaaccc ctccgaccag ccgacgcgcc gggcactgtt caggttttca ccgctgactc | 3342 |

-continued

```
ggttgatcca aggccgcttg cgcaaccgcg aaattcccgt gaccagagtg ttgaacttca    3402
gcaaaatcag ccgcagccca gccctgagca aattgtgcgc ggccgatgaa tttagcggag    3462
catccaaaat aacctggggt ttcctcgcgt catatgtgca acacaaggcc aaactgggtg    3522
cagttcccgt cactctgatg cacctgacc acgaccttct gactcccgtt gagctcagtc     3582
tgcgtacgct ttcgcgcc                                                   3600
```

<210> SEQ ID NO 45
<211> LENGTH: 502
<212> TYPE: PRT
<213> ORGANISM: Corynebacterium glutamicum

<400> SEQUENCE: 45

```
Met Ser Asp Arg Ile Ala Ser Glu Lys Leu Arg Ser Lys Leu Met Ser
 1               5                  10                  15

Ala Asp Glu Ala Ala Gln Phe Val Asn His Gly Asp Lys Val Gly Phe
            20                  25                  30

Ser Gly Phe Thr Gly Ala Gly Tyr Pro Lys Ala Leu Pro Thr Ala Ile
        35                  40                  45

Ala Asn Arg Ala Lys Glu Ala His Gly Ala Gly Asn Asp Tyr Ala Ile
    50                  55                  60

Asp Leu Phe Thr Gly Ala Ser Thr Ala Pro Asp Cys Asp Gly Val Leu
65                  70                  75                  80

Ala Glu Ala Asp Ala Ile Arg Trp Arg Met Pro Tyr Ala Ser Asp Pro
                85                  90                  95

Ile Met Arg Asn Lys Ile Asn Ser Gly Ser Met Gly Tyr Ser Asp Ile
            100                 105                 110

His Leu Ser His Ser Gly Gln Gln Val Glu Glu Gly Phe Phe Gly Gln
        115                 120                 125

Leu Asn Val Ala Val Ile Glu Ile Thr Arg Ile Thr Glu Glu Gly Tyr
    130                 135                 140

Ile Ile Pro Ser Ser Ser Val Gly Asn Asn Val Glu Trp Leu Asn Ala
145                 150                 155                 160

Ala Glu Lys Val Ile Leu Glu Val Asn Ser Trp Gln Ser Glu Asp Leu
                165                 170                 175

Glu Gly Met His Asp Ile Trp Ser Val Pro Ala Leu Pro Asn Arg Ile
            180                 185                 190

Ala Val Pro Ile Asn Lys Pro Gly Asp Arg Ile Gly Lys Thr Tyr Ile
        195                 200                 205

Glu Phe Asp Thr Asp Lys Val Val Ala Val Val Glu Thr Asn Thr Ala
    210                 215                 220

Asp Arg Asn Ala Pro Phe Lys Pro Val Asp Ile Ser Lys Lys Ile
225                 230                 235                 240

Ala Gly Asn Phe Leu Asp Phe Leu Glu Ser Glu Val Ala Ala Gly Arg
                245                 250                 255

Leu Ser Tyr Asp Gly Tyr Ile Met Gln Ser Gly Val Gly Asn Val Pro
            260                 265                 270

Asn Ala Val Met Ala Gly Leu Leu Glu Ser Lys Phe Glu Asn Ile Gln
        275                 280                 285

Ala Tyr Thr Glu Val Ile Gln Asp Gly Met Val Asp Leu Ile Asp Ala
    290                 295                 300

Gly Lys Met Thr Val Ala Ser Ala Thr Ser Phe Ser Leu Ser Pro Glu
305                 310                 315                 320

Tyr Ala Glu Lys Met Asn Asn Glu Ala Lys Arg Tyr Arg Glu Ser Ile
```

```
                    325                 330                 335
Ile Leu Arg Pro Gln Gln Ile Ser Asn His Pro Glu Val Ile Arg Arg
            340                 345                 350

Val Gly Leu Ile Ala Thr Asn Gly Leu Ile Glu Ala Asp Ile Tyr Gly
            355                 360                 365

Asn Val Asn Ser Thr Asn Val Ser Gly Ser Arg Val Met Asn Gly Ile
            370                 375                 380

Gly Gly Ser Gly Asp Phe Thr Arg Asn Gly Tyr Ile Ser Ser Phe Ile
385                 390                 395                 400

Thr Pro Ser Glu Ala Lys Gly Gly Ala Ile Ser Ala Ile Val Pro Phe
                405                 410                 415

Ala Ser His Ile Asp His Thr Glu His Asp Val Met Val Val Ile Ser
            420                 425                 430

Glu Tyr Gly Tyr Ala Asp Leu Arg Gly Leu Ala Pro Arg Glu Arg Val
            435                 440                 445

Ala Lys Met Ile Gly Leu Ala His Pro Asp Tyr Arg Pro Leu Leu Glu
            450                 455                 460

Glu Tyr Tyr Ala Arg Ala Thr Ser Gly Asp Asn Lys Tyr Met Gln Thr
465                 470                 475                 480

Pro His Asp Leu Ala Thr Ala Phe Asp Phe His Ile Asn Leu Ala Lys
                485                 490                 495

Asn Gly Ser Met Lys Ala
            500

<210> SEQ ID NO 46
<211> LENGTH: 3423
<212> TYPE: DNA
<213> ORGANISM: Corynebacterium glutamicum
<220> FEATURE:
<221> NAME/KEY: CDS
<222> LOCATION: (1)..(3420)

<400> SEQUENCE: 46 gtg tcg act cac aca tct tca acg ctt cca gca ttc aaa aag atc ttg     48
Val Ser Thr His Thr Ser Ser Thr Leu Pro Ala Phe Lys Lys Ile Leu
  1               5                  10                  15 gta gca aac cgc ggc gaa atc gcg gtc cgt gct ttc cgt gca gca ctc     96
Val Ala Asn Arg Gly Glu Ile Ala Val Arg Ala Phe Arg Ala Ala Leu
             20                  25                  30 gaa acc ggt gca gcc acg gta gct att tac ccc cgt gaa gat cgg gga    144
Glu Thr Gly Ala Ala Thr Val Ala Ile Tyr Pro Arg Glu Asp Arg Gly
         35                  40                  45 tca ttc cac cgc tct ttt gct tct gaa gct gtc cgc att ggt acc gaa    192
Ser Phe His Arg Ser Phe Ala Ser Glu Ala Val Arg Ile Gly Thr Glu
     50                  55                  60 ggc tca cca gtc aag gcg tac ctg gac atc gat gaa att atc ggt gca    240
Gly Ser Pro Val Lys Ala Tyr Leu Asp Ile Asp Glu Ile Ile Gly Ala
 65                  70                  75                  80 gct aaa aaa gtt aaa gca gat gcc att tac ccg gga tac ggc ttc ctg    288
Ala Lys Lys Val Lys Ala Asp Ala Ile Tyr Pro Gly Tyr Gly Phe Leu
                 85                  90                  95 tct gaa aat gcc cag ctt gcc cgc gag tgt gcg gaa aac ggc att act    336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct    384
Phe Ile Gly Pro Thr Pro Glu Val Leu Asp Leu Thr Gly Asp Lys Ser
        115                 120                 125 cgc gcg gta acc gcc gcg aag aag gct ggt ctg cca gtt ttg gcg gaa    432
Arg Ala Val Thr Ala Ala Lys Lys Ala Gly Leu Pro Val Leu Ala Glu
```

```
                130                 135                 140
tcc acc ccg agc aaa aac atc gat gag atc gtt aaa agc gct gaa ggc      480
Ser Thr Pro Ser Lys Asn Ile Asp Glu Ile Val Lys Ser Ala Glu Gly
145                 150                 155                 160 cag act tac ccc atc ttt gtg aag gca gtt gcc ggt ggt gga cgc          528
Gln Thr Tyr Pro Ile Phe Val Lys Ala Val Ala Gly Gly Gly Arg
                165                 170                 175 ggt atg cgt ttt gtt gct tca cct gat gag ctt cgc aaa tta gca aca      576
Gly Met Arg Phe Val Ala Ser Pro Asp Glu Leu Arg Lys Leu Ala Thr
        180                 185                 190 gaa gca tct cgt gaa gct gaa gcg gct ttc ggc gat ggc gcg gta tat      624
Glu Ala Ser Arg Glu Ala Glu Ala Ala Phe Gly Asp Gly Ala Val Tyr
            195                 200                 205 gtc gaa cgt gct gtg att aac cct cag cat att gaa gtg cag atc ctt      672
Val Glu Arg Ala Val Ile Asn Pro Gln His Ile Glu Val Gln Ile Leu
210                 215                 220 ggc gat cac act gga gaa gtt gta cac ctt tat gaa cgt gac tgc tca      720
Gly Asp His Thr Gly Glu Val Val His Leu Tyr Glu Arg Asp Cys Ser
225                 230                 235                 240 ctg cag cgt cgt cac caa aaa gtt gtc gaa att gcg cca gca cag cat      768
Leu Gln Arg Arg His Gln Lys Val Val Glu Ile Ala Pro Ala Gln His
                245                 250                 255 ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
        260                 265                 270 tgc cgc tcc att ggt tac cag ggc gcg gga acc gtg gaa ttc ttg gtc      864
Cys Arg Ser Ile Gly Tyr Gln Gly Ala Gly Thr Val Glu Phe Leu Val
            275                 280                 285 gat gaa aag ggc aac cac gtc ttc atc gaa atg aac cca cgt atc cag      912
Asp Glu Lys Gly Asn His Val Phe Ile Glu Met Asn Pro Arg Ile Gln
290                 295                 300 gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320 gcg cag atg cgc ttg gct gct ggt gca acc ttg aag gaa ttg ggt ctg      1008
Ala Gln Met Arg Leu Ala Ala Gly Ala Thr Leu Lys Glu Leu Gly Leu
                325                 330                 335 acc caa gat aag atc aag acc cac ggt gca gca ctg cag tgc cgc atc      1056
Thr Gln Asp Lys Ile Lys Thr His Gly Ala Ala Leu Gln Cys Arg Ile
        340                 345                 350 acc acg gaa gat cca aac aac ggc ttc cgc cca gat acc gga act atc      1104
Thr Thr Glu Asp Pro Asn Asn Gly Phe Arg Pro Asp Thr Gly Thr Ile
            355                 360                 365 acc gcg tac cgc tca cca ggc gga gct ggc gtt cgt ctt gac ggt gca      1152
Thr Ala Tyr Arg Ser Pro Gly Gly Ala Gly Val Arg Leu Asp Gly Ala
370                 375                 380 gct cag ctc ggt ggc gaa atc acc gca cac ttt gac tcc atg ctg gtg      1200
Ala Gln Leu Gly Gly Glu Ile Thr Ala His Phe Asp Ser Met Leu Val
385                 390                 395                 400 aaa atg acc tgc cgt ggt tcc gac ttt gaa act gct gtt gct cgt gca      1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att      1296
Gln Arg Ala Leu Ala Glu Phe Thr Val Ser Gly Val Ala Thr Asn Ile
        420                 425                 430 ggt ttc ttg cgt gcg ttg ctg cgg gaa gag gac ttc act tcc aag cgc      1344
Gly Phe Leu Arg Ala Leu Leu Arg Glu Glu Asp Phe Thr Ser Lys Arg
            435                 440                 445 atc gcc acc gga ttc att gcc gat cac ccg cac ctc ctt cag gct cca      1392
Ile Ala Thr Gly Phe Ile Ala Asp His Pro His Leu Leu Gln Ala Pro
```

```
                                -continued
     450                455                460
cct gct gat gat gag cag gga cgc atc ctg gat tac ttg gca gat gtc   1440
Pro Ala Asp Asp Glu Gln Gly Arg Ile Leu Asp Tyr Leu Ala Asp Val
465                 470                475                480 acc gtg aac aag cct cat ggt gtg cgt cca aag gat gtt gca gct cct   1488
Thr Val Asn Lys Pro His Gly Val Arg Pro Lys Asp Val Ala Ala Pro
                485                490                495 atc gat aag ctg cct aac atc aag gat ctg cca ctg cca cgc ggt tcc   1536
Ile Asp Lys Leu Pro Asn Ile Lys Asp Leu Pro Leu Pro Arg Gly Ser
        500                505                510 cgt gac cgc ctg aag cag ctt ggc cca gcc gcg ttt gct cgt gat ctc   1584
Arg Asp Arg Leu Lys Gln Leu Gly Pro Ala Ala Phe Ala Arg Asp Leu
            515                520                525 cgt gag cag gac gca ctg gca gtt act gat acc acc ttc cgc gat gca   1632
Arg Glu Gln Asp Ala Leu Ala Val Thr Asp Thr Thr Phe Arg Asp Ala
530                535                540 cac cag tct ttg ctt gcg acc cga gtc cgc tca ttc gca ctg aag cct   1680
His Gln Ser Leu Leu Ala Thr Arg Val Arg Ser Phe Ala Leu Lys Pro
545                550                555                560 gcg gca gag gcc gtc gca aag ctg act cct gag ctt ttg tcc gtg gag   1728
Ala Ala Glu Ala Val Ala Lys Leu Thr Pro Glu Leu Leu Ser Val Glu
                565                570                575 gcc tgg ggc ggc gcg acc tac gat gtg gcg atg cgt ttc ctc ttt gag   1776
Ala Trp Gly Gly Ala Thr Tyr Asp Val Ala Met Arg Phe Leu Phe Glu
            580                585                590 gat ccg tgg gac agg ctc gac gag ctg cgc gag gcg atg ccg aat gta   1824
Asp Pro Trp Asp Arg Leu Asp Glu Leu Arg Glu Ala Met Pro Asn Val
        595                600                605 aac att cag atg ctg ctt cgc ggc cgc aac acc gtg gga tac acc ccg   1872
Asn Ile Gln Met Leu Leu Arg Gly Arg Asn Thr Val Gly Tyr Thr Pro
610                615                620 tac cca gac tcc gtc tgc cgc gcg ttt gtt aag gaa gct gcc agc tcc   1920
Tyr Pro Asp Ser Val Cys Arg Ala Phe Val Lys Glu Ala Ala Ser Ser
625                630                635                640 ggc gtg gac atc ttc cgc atc ttc gac gcg ctt aac gac gtc tcc cag   1968
Gly Val Asp Ile Phe Arg Ile Phe Asp Ala Leu Asn Asp Val Ser Gln
                645                650                655 atg cgt cca gca atc gac gca gtc ctg gag acc aac acc gcg gta gcc   2016
Met Arg Pro Ala Ile Asp Ala Val Leu Glu Thr Asn Thr Ala Val Ala
            660                665                670 gag gtg gct atg gct tat tct ggt gat ctc tct gat cca aat gaa aag   2064
Glu Val Ala Met Ala Tyr Ser Gly Asp Leu Ser Asp Pro Asn Glu Lys
        675                680                685 ctc tac acc ctg gat tac tac cta aag atg gca gag gag atc gtc aag   2112
Leu Tyr Thr Leu Asp Tyr Tyr Leu Lys Met Ala Glu Glu Ile Val Lys
690                695                700 tct ggc gct cac atc ttg gcc att aag gat atg gct ggt ctg ctt cgc   2160
Ser Gly Ala His Ile Leu Ala Ile Lys Asp Met Ala Gly Leu Leu Arg
705                710                715                720 cca gct gcg gta acc aag ctg gtc acc gca ctg cgc cgt gaa ttc gat   2208
Pro Ala Ala Val Thr Lys Leu Val Thr Ala Leu Arg Arg Glu Phe Asp
                725                730                735 ctg cca gtg cac gtg cac acc cac gac act gcg ggt ggc cag ctg gca   2256
Leu Pro Val His Val His Thr His Asp Thr Ala Gly Gly Gln Leu Ala
            740                745                750 acc tac ttt gct gca gct caa gct ggt gca gat gct gtt gac ggt gct   2304
Thr Tyr Phe Ala Ala Ala Gln Ala Gly Ala Asp Ala Val Asp Gly Ala
        755                760                765 tcc gca cca ctg tct ggc acc acc tcc cag cca tcc ctg tct gcc att   2352
Ser Ala Pro Leu Ser Gly Thr Thr Ser Gln Pro Ser Leu Ser Ala Ile
```

```
                770                 775                 780
gtt gct gca ttc gcg cac acc cgt cgc gat acc ggt ttg agc ctc gag       2400
Val Ala Ala Phe Ala His Thr Arg Arg Asp Thr Gly Leu Ser Leu Glu
785                 790                 795                 800 gct gtt tct gac ctc gag ccg tac tgg gaa gca gtg cgc gga ctg tac       2448
Ala Val Ser Asp Leu Glu Pro Tyr Trp Glu Ala Val Arg Gly Leu Tyr
                    805                 810                 815 ctg cca ttt gag tct gga acc cca ggc cca acc ggt cgc gtc tac cgc       2496
Leu Pro Phe Glu Ser Gly Thr Pro Gly Pro Thr Gly Arg Val Tyr Arg
                820                 825                 830 cac gaa atc cca ggc gga cag ttg tcc aac ctg cgt gca cag gcc acc       2544
His Glu Ile Pro Gly Gly Gln Leu Ser Asn Leu Arg Ala Gln Ala Thr
            835                 840                 845 gca ctg ggc ctt gcg gat cgt ttc gaa ctc atc gaa gac aac tac gca       2592
Ala Leu Gly Leu Ala Asp Arg Phe Glu Leu Ile Glu Asp Asn Tyr Ala
850                 855                 860 gcc gtt aat gag atg ctg gga cgc cca acc aag gtc acc cca tcc tcc       2640
Ala Val Asn Glu Met Leu Gly Arg Pro Thr Lys Val Thr Pro Ser Ser
865                 870                 875                 880 aag gtt gtt ggc gac ctc gca ctc cac ctc gtt ggt gcg ggt gtg gat       2688
Lys Val Val Gly Asp Leu Ala Leu His Leu Val Gly Ala Gly Val Asp
                    885                 890                 895 cca gca gac ttt gct gcc gat cca caa aag tac gac atc cca gac tct       2736
Pro Ala Asp Phe Ala Ala Asp Pro Gln Lys Tyr Asp Ile Pro Asp Ser
                900                 905                 910 gtc atc gcg ttc ctg cgc ggc gag ctt ggt aac cct cca ggt ggc tgg       2784
Val Ile Ala Phe Leu Arg Gly Glu Leu Gly Asn Pro Pro Gly Gly Trp
            915                 920                 925 cca gag cca ctg cgc acc cgc gca ctg gaa ggc cgc tcc gaa ggc aag       2832
Pro Glu Pro Leu Arg Thr Arg Ala Leu Glu Gly Arg Ser Glu Gly Lys
930                 935                 940 gca cct ctg acg gaa gtt cct gag gaa gag cag gcg cac ctc gac gct       2880
Ala Pro Leu Thr Glu Val Pro Glu Glu Glu Gln Ala His Leu Asp Ala
945                 950                 955                 960 gat gat tcc aag gaa cgt cgc aat agc ctc aac cgc ctg ctg ttc ccg       2928
Asp Asp Ser Lys Glu Arg Arg Asn Ser Leu Asn Arg Leu Leu Phe Pro
                    965                 970                 975 aag cca acc gaa gag ttc ctc gag cac cgt cgc cgc ttc ggc aac acc       2976
Lys Pro Thr Glu Glu Phe Leu Glu His Arg Arg Arg Phe Gly Asn Thr
                980                 985                 990 tct gcg ctg gat gat cgt gaa ttc ttc tac ggc ctg gtc gaa ggc cgc       3024
Ser Ala Leu Asp Asp Arg Glu Phe Phe Tyr Gly Leu Val Glu Gly Arg
            995                 1000                1005 gag act ttg atc cgc ctg cca gat gtg cgc acc cca ctg ctt gtt cgc       3072
Glu Thr Leu Ile Arg Leu Pro Asp Val Arg Thr Pro Leu Leu Val Arg
    1010                1015                1020 ctg gat gcg atc tct gag cca gac gat aag ggt atg cgc aat gtt gtg       3120
Leu Asp Ala Ile Ser Glu Pro Asp Asp Lys Gly Met Arg Asn Val Val
1025                1030                1035                1040 gcc aac gtc aac ggc cag atc cgc cca atg cgt gtg cgt gac cgc tcc       3168
Ala Asn Val Asn Gly Gln Ile Arg Pro Met Arg Val Arg Asp Arg Ser
                    1045                1050                1055 gtt gag tct gtc acc gca acc gca gaa aag gca gat tcc tcc aac aag       3216
Val Glu Ser Val Thr Ala Thr Ala Glu Lys Ala Asp Ser Ser Asn Lys
                1060                1065                1070 ggc cat gtt gct gca cca ttc gct ggt gtt gtc acc gtg act gtt gct       3264
Gly His Val Ala Ala Pro Phe Ala Gly Val Val Thr Val Thr Val Ala
            1075                1080                1085 gaa ggt gat gag gtc aag gct gga gat gca gtc gca atc atc gag gct       3312
Glu Gly Asp Glu Val Lys Ala Gly Asp Ala Val Ala Ile Ile Glu Ala
```

-continued

```
                  1090                1095                1100
atg aag atg gaa gca aca atc act gct tct gtt gac ggc aaa atc gat    3360
Met Lys Met Glu Ala Thr Ile Thr Ala Ser Val Asp Gly Lys Ile Asp
1105                1110                1115                1120 cgc gtt gtg gtt cct gct gca acg aag gtg gaa ggt ggc gac ttg atc    3408
Arg Val Val Val Pro Ala Ala Thr Lys Val Glu Gly Gly Asp Leu Ile
                1125                1130                1135 gtc gtc gtt tcc taa                                                3423
Val Val Val Ser
        1140

<210> SEQ ID NO 47
<211> LENGTH: 1140
<212> TYPE: PRT
<213> ORGANISM: Corynebacterium glutamicum

<400> SEQUENCE: 47

Val Ser Thr His Thr Ser Ser Thr Leu Pro Ala Phe Lys Lys Ile Leu
 1               5                  10                  15

Val Ala Asn Arg Gly Glu Ile Ala Val Arg Ala Phe Arg Ala Ala Leu
             20                  25                  30

Glu Thr Gly Ala Ala Thr Val Ala Ile Tyr Pro Arg Glu Asp Arg Gly
         35                  40                  45

Ser Phe His Arg Ser Phe Ala Ser Glu Ala Val Arg Ile Gly Thr Glu
     50                  55                  60

Gly Ser Pro Val Lys Ala Tyr Leu Asp Ile Asp Glu Ile Ile Gly Ala
 65                  70                  75                  80

Ala Lys Lys Val Lys Ala Asp Ala Ile Tyr Pro Gly Tyr Gly Phe Leu
                 85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
```

```
                305                 310                 315                 320
Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
                355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
        450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
        530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
        610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
        690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735
```

```
Leu Pro Val His Val His Thr His Asp Thr Ala Gly Gln Leu Ala
            740             745             750

Thr Tyr Phe Ala Ala Ala Gln Ala Gly Ala Asp Ala Val Asp Gly Ala
        755             760             765

Ser Ala Pro Leu Ser Gly Thr Thr Ser Gln Pro Ser Leu Ser Ala Ile
770             775             780

Val Ala Ala Phe Ala His Thr Arg Arg Asp Thr Gly Leu Ser Leu Glu
785             790             795             800

Ala Val Ser Asp Leu Glu Pro Tyr Trp Glu Ala Val Arg Gly Leu Tyr
            805             810             815

Leu Pro Phe Glu Ser Gly Thr Pro Gly Pro Thr Gly Arg Val Tyr Arg
        820             825             830

His Glu Ile Pro Gly Gly Gln Leu Ser Asn Leu Arg Ala Gln Ala Thr
    835             840             845

Ala Leu Gly Leu Ala Asp Arg Phe Glu Leu Ile Glu Asp Asn Tyr Ala
    850             855             860

Ala Val Asn Glu Met Leu Gly Arg Pro Thr Lys Val Thr Pro Ser Ser
865             870             875             880

Lys Val Val Gly Asp Leu Ala Leu His Leu Val Gly Ala Gly Val Asp
            885             890             895

Pro Ala Asp Phe Ala Ala Asp Pro Gln Lys Tyr Asp Ile Pro Asp Ser
        900             905             910

Val Ile Ala Phe Leu Arg Gly Glu Leu Gly Asn Pro Pro Gly Gly Trp
    915             920             925

Pro Glu Pro Leu Arg Thr Arg Ala Leu Glu Gly Arg Ser Glu Gly Lys
    930             935             940

Ala Pro Leu Thr Glu Val Pro Glu Glu Gln Ala His Leu Asp Ala
945             950             955             960

Asp Asp Ser Lys Glu Arg Arg Asn Ser Leu Asn Arg Leu Leu Phe Pro
            965             970             975

Lys Pro Thr Glu Glu Phe Leu Glu His Arg Arg Arg Phe Gly Asn Thr
        980             985             990

Ser Ala Leu Asp Asp Arg Glu Phe Phe Tyr Gly Leu Val Glu Gly Arg
    995             1000            1005

Glu Thr Leu Ile Arg Leu Pro Asp Val Arg Thr Pro Leu Leu Val Arg
    1010            1015            1020

Leu Asp Ala Ile Ser Glu Pro Asp Asp Lys Gly Met Arg Asn Val Val
1025            1030            1035            1040

Ala Asn Val Asn Gly Gln Ile Arg Pro Met Arg Val Arg Asp Arg Ser
            1045            1050            1055

Val Glu Ser Val Thr Ala Thr Ala Glu Lys Ala Asp Ser Ser Asn Lys
        1060            1065            1070

Gly His Val Ala Ala Pro Phe Gly Val Val Thr Val Thr Val Ala
    1075            1080            1085

Glu Gly Asp Glu Val Lys Ala Gly Asp Ala Val Ala Ile Ile Glu Ala
    1090            1095            1100

Met Lys Met Glu Ala Thr Ile Thr Ala Ser Val Asp Gly Lys Ile Asp
1105            1110            1115            1120

Arg Val Val Val Pro Ala Ala Thr Lys Val Glu Gly Gly Asp Leu Ile
            1125            1130            1135

Val Val Val Ser
            1140
```

US 7,972,823 B2

SUCCINIC ACID-PRODUCING BACTERIUM AND PROCESS FOR PRODUCING SUCCINIC ACID

CROSS-REFERENCE TO RELATED APPLICATION

This application is a Continuation of International Application No. PCT/JP2005/009232, filed May 20, 2005.

TECHNICAL FIELD

The present invention relates to a fermentation industry, and to a process for efficiently producing succinic acid by a fermentation method using a coryneform bacterium.

BACKGROUND ART

For production of non-amino organic acids including succinic acid by fermentation, usually, anaerobic bacteria such as those belonging to the genus *Anaerobiospirillum* or *Actinobacillus* are used (Patent Document 1 or 2, and Non-Patent Document 1). The use of anaerobic bacteria makes the yield of products high, while such bacteria require many nutrients for proliferation and therefore, there is a need for adding a large amount of organic nitrogen sources such as corn steep liquor (CSL) to a medium. The addition of abundant amounts of organic nitrogen sources not only leads to an increase in cost of the medium but also leads to an increase in cost of purification for isolating the product, which is uneconomical.

Furthermore, a method, which comprises culturing aerobic bacteria such as coryneform bacteria under an aerobic condition to proliferate bacterial cells and then collecting and washing the cells to use them as resting bacteria to produce succinic acid without oxygen aeration, has been known (Patent Document 3 and 4). This method is economical because the bacterial cells can grow sufficiently in a simple medium, into which a small amount of organic nitrogen is added for proliferation of bacterial cells, but this method is still to be improved in terms of the amount of generated succinic acid, the concentration thereof, and the production rate thereof per bacterial cells as well as simplification of production process, and the like.

Furthermore, when aerobic bacteria such as coryneform bacteria are cultured under oxygen-limited conditions, organic acids other than a desired substance such as lactic acid and acetic acid are excessively accumulated as by-products, resulting in suppressed growth of bacterial cells and significantly decreased productivity in fermentation. In addition, excessive amounts of counterions to neutralize the organic acids generated as by-products are required, thereby resulting in being uneconomical. To solve such problems, reduction in lactate generated as a by-product has been performed by using a coryneform bacterium having a reduced lactate dehydrogenase activity (Patent Document 5).

Even if the above-mentioned coryneform bacterium having a reduced lactate dehydrogenase activity is used, a large amount of acetic acid is generated as a by-product. As means for achieving the reduction of acetic acid in a culture medium, there have been known a method of enhancing expression of an acetic acid assimilating gene (aceP) in a bacterium belonging to the genus *Escherichia* (Patent Document 6), a method of enhancing expression of a gene encoding ACE protein in a bacterium belonging to the genus *Escherichia* (Patent Document 7), and the like. Those methods are intended to reduce generation of acetic acid as a by-product by actively assimilating acetic acid released into a culture medium. Meanwhile, as methods of suppressing generation of acetic acid as a by-product by suppressing the biosynthesis of acetic acid, there have been known a method of producing succinic acid using *Escherichia coli* in which phosphoacetyltransferase (pta) and lactate dehydrogenase (ldh) are deficient (Patent Document 8), a method of producing an amino acid using an enterobacterium in which pyruvate oxidase (poxB) is deficient, and a method of producing D-pantothenic acid using an enterobacterium in which pyruvate oxidase (poxB) is deficient (Patent Document 9).

As enzymes responsible for assimilation of acetic acid in coryneform bacteria, there have been reported acetate kinase (ack) and phosphotransacetylase (pta) (Non-Patent Document 2). On the other hand, it is assumed that not only the above-mentioned enzymes but also a plurality of enzymes such as pyruvate oxidase (poxB) (Patent Document 10), acylphosphatase (acp), aldehyde dehydrogenase, and acetyl-CoA hydrolase are responsible for generation of acetic acid, but a specific enzyme that contributes to the synthesis of acetic acid has not been clarified. Therefore, there has not been known a method of producing succinic acid using a strain of a coryneform bacterium having a decreased acetic acid biosynthetic enzyme.

Acetyl-CoA hydrolase is an enzyme to generate acetic acid from acetyl-CoA and water (3.1.2.1) and the gene sequence in *Corynebacterium glutamicum* has been predicted (Patent Document 11). However, no report has been provided for cloning of the gene and expression analysis of the gene, and its actual function has not been clarified.

Patent Document 1: U.S. Pat. No. 5,143,833
Patent Document 2: U.S. Pat. No. 5,504,004
Patent Document 3: JP11-113588A
Patent Document 4: JP11-196888A
Patent Document 5: JP11-206385A
Patent Document 6: JP06-14781A
Patent Document 7: JP07-67683A
Patent Document 8: WO 99/06532
Patent Document 9: WO 02/36797
Patent Document 10: EP1096013A
Patent Document 11: EP1108790A
Non-Patent Document 1: International Journal of Systematic Bacteriology, vol. 49, p 207-216, 1999
Non-Patent Document 2: Microbiology. 1999, February; 145 (Pt 2): 503-13

DISCLOSURE OF THE INVENTION

An object of the present invention is to provide a coryneform bacterium having an improved succinic acid-producing ability.

The inventors of the present invention have intensively studied for solving the aforementioned problems, and as a result found that succinic acid-producing ability is improved by decreasing an activity of acetyl-CoA hydrolase in a coryneform bacterium. Furthermore, they found that generation of acetic acid as a by-product is reduced by decreasing activities of phosphotransacetylase and acetate kinase in addition to the acetyl-CoA hydrolase activity, thereby accomplished the present invention.

That is, the present invention is as follows.

(1) A coryneform bacterium having a succinic acid-producing ability, wherein said bacterium has been modified so that an activity of acetyl-CoA hydrolase is decreased.

(2) The coryneform bacterium according to (1), wherein the acetyl-CoA hydrolase is a protein as described in the following (A) or (B):

(A) a protein having an amino acid sequence of SEQ ID NO: 45; or
(B) a protein having an amino acid sequence of SEQ ID NO: 45 including substitution, deletion, insertion, or addition of one or several amino acids, and having an acetyl-CoA hydrolase activity.
(3) The coryneform bacterium according to (1) or (2), wherein the acetyl-CoA hydrolase activity has been decreased by disruption of an acetyl-CoA hydrolase gene on a chromosome.
(4) The coryneform bacterium according to (3), wherein the acetyl-CoA hydrolase gene is a DNA as described in the following (a) or (b):
(a) a DNA comprising a nucleotide sequence of nucleotide numbers 1037-2542 in SEQ ID NO: 44; or
(b) a DNA that hybridizes with a nucleotide sequence of nucleotide numbers 1037-2542 in SEQ ID NO: 44 or a probe that can be prepared from the nucleotide sequence under stringent conditions, and encodes a protein having an acetyl-CoA hydrolase activity.
(5) The coryneform bacterium according to any one of (1) to (4), which has been further modified so that activities of one or both of phosphotransacetylase and acetate kinase are decreased.
(6) The coryneform bacterium according to any one of (1) to (5), wherein said bacterium has been further modified so that an activity of lactate dehydrogenase is decreased.
(7) The coryneform bacterium according to any one of (1) to (6), wherein said bacterium has been further modified so that an activity of pyruvate carboxylase is increased.
(8) A method for producing succinic acid, comprising allowing the coryneform bacterium according to any one of (1) to (7) or a treated product thereof to act on an organic raw material in a reaction liquid containing carbonate ion, bicarbonate ion, or carbon dioxide to generate and accumulate succinic acid in the reaction liquid, and collecting succinic acid from the reaction liquid.
(9) The production method according to (8), wherein the coryneform bacterium or treated product thereof is allowed to act on the organic raw material under anaerobic conditions.
(10) A method for producing a succinic acid-containing polymer, comprising the steps of producing succinic acid by the method according to (8) or (9) and polymerizing the obtained succinic acid.

DESCRIPTION OF THE PREFERRED EMBODIMENTS

Figure 1:
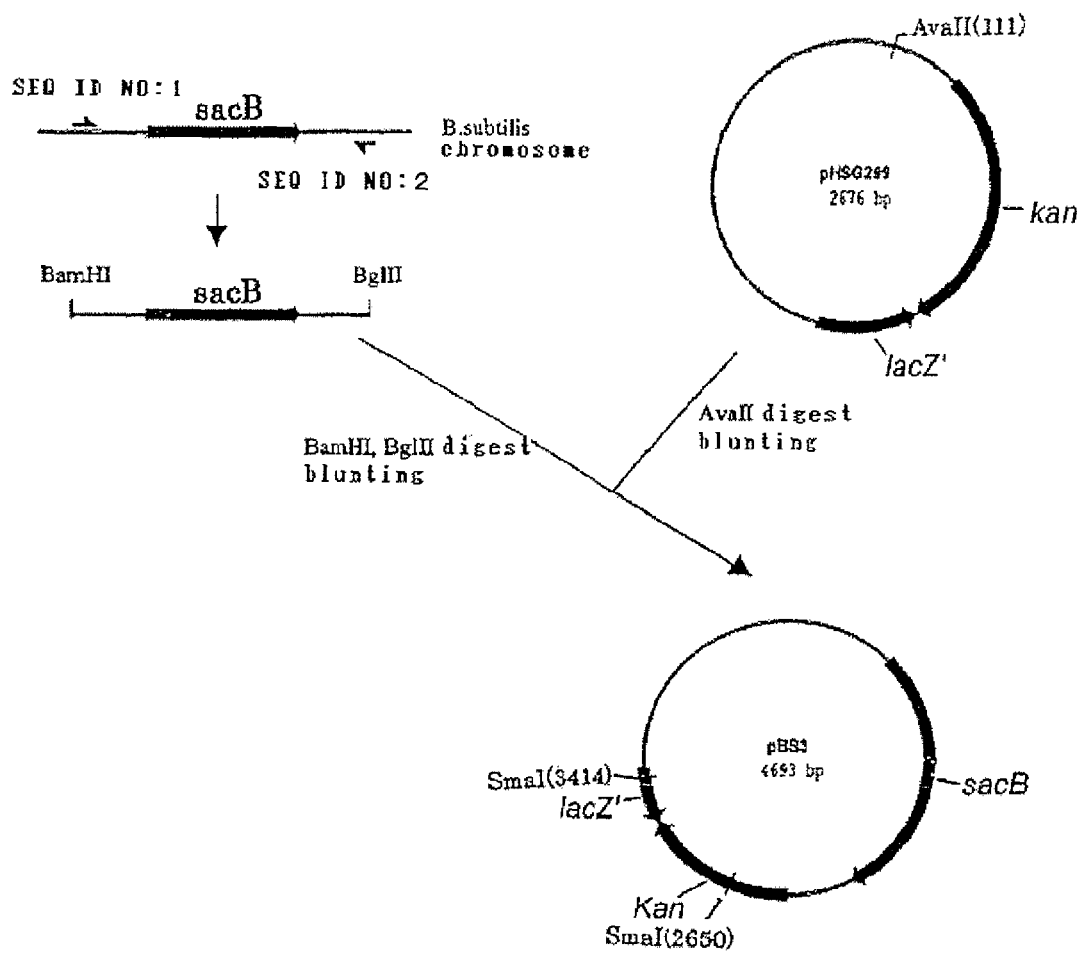
FIG. 1 shows the procedures for constructing plasmid pBS3.

Hereinafter, embodiments of the present invention will be described in detail.

<1> Coryneform Bacterium to be Used in the Present Invention

In the present invention, the term "coryneform bacterium" includes a bacterium which had been classified as the genus *Brevibacterium* but now classified as the genus *Corynebacterium* (Int. J. Syst. Bacteriol., 41, 255(1991)), and it also includes a bacterium belonging to the genus *Brevibacterium*, which is very closely related to *Corynebacterium*. Examples of such coryneform bacteria include the following.

*Corynebacterium acetoacidophlilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes*
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium selinum*
*Microbacterium ammoniaphilum*

In the present invention, the term "succinic acid-producing ability" means an ability to accumulate succinic acid in a medium when the coryneform bacterium of the present invention is cultured. The succinic acid-producing ability may be a feature inherent to a wild-type coryneform bacterium or a feature provided by breeding.

To provide the succinic acid-producing ability by breeding, there may be applied methods that have been employed in breeding of coryneform bacteria, which include acquisition of metabolic regulation mutant strains, creation of a recombinant strain having an enhanced biosynthetic enzyme for a desired substance, and the like (Amino Acid Fermentation, Japan Scientific Societies Press, the first edition published on May 30, 1986, p 77-100). In these methods, one or two or three or more features such as metabolic regulation mutations and enhancement of biosynthetic enzymes for a desired substance may be provided. Imparting properties such as metabolic regulation mutations and enhancement of biosynthetic enzymes may be combined.

Particularly preferable specific examples of a coryneform bacterium having a succinic acid-producing ability include *Brevibacterium flavum* MJ233Δldh strain having decreased lactate dehydrogenase activity (JP11-206385A), *Brevibacterium flavum* MJ233/pPCPYC strain having enhanced activity of pyruvate carboxylase or phosphoenol pyruvate carboxylase (WO 01/27258 and JP11-196887A), *Brevibacterium flavum* MJ-233 (FERM BP-1497, *Brevibacterium flavum* MJ-233 AB-41 (FERM BP-1498), *Brevibacterium ammoniagenes* ATCC6872, *Corynebacterium glutamicum* ATCC31831, and *Brevibacterium lactofermentum* ATCC13869. Since *Brevibacterium flavum* may be currently classified as *Corynebacterium glutamicum* (Lielbl, W., Ehrmann, M., Ludwig, W. and Schleifer, K. H., International Journal of Systematic Bacteriology, 1991, vol. 41, p 255-260), the aforementioned *Brevibacterium flavum* MJ-233 strain and its mutant MJ-233 AB-41 strain, are defined as the same strains as *Corynebacterium glutamicum* MJ-233 strain and *Corynebacterium glutamicum* MJ-233 AB-41 strain, respectively.

<2> Construction of the Coryneform Bacterium of the Present Invention

The coryneform bacterium of the present invention has the above-mentioned succinic acid-producing ability and has been modified so that an activity of acetyl-CoA hydrolase is decreased.

In breeding of the coryneform bacterium of the present invention, the provision of succinic acid-producing ability and the modification to decrease the acetyl-CoA hydrolase (EC 3.1.2.1) activity may be performed in any order.

The term "acetyl-CoA hydrolase (ACH) activity" means an activity to catalyze the reaction to generate acetic acid from acetyl-CoA and water. The term "modified so that activity of acetyl-CoA hydrolase is decreased" means that an activity of acetyl-CoA hydrolase is decreased as compared to a specific activity of an unmodified strain such as a wild-type coryneform bacterium. The ACH activity is preferably decreased to 50% or less per bacterial cells, more preferably 30% or less, further more preferably 10% or less per bacterial cells as compared to an unmodified strain. Here, examples of a wild-type coryneform bacterium to be used as a control include *Brevibacterium lactofermentum* ATCC13869 (wild-type strain) and *Brevibacterium lactofermentum* Δldh strain (unmodified strain). The activity of acetyl-CoA hydrolase can be determined according to the method of Gergely, J., et al. (Gergely, J., Hele, P. & Ramkrishnan, C. V. (1952) J. Biol. Chem. 198 p 323-334). The term "decreased" includes complete loss of the activity. The coryneform bacterium of the present invention preferably has an acetyl-CoA hydrolase activity lower than a wild-type or unmodified strain and more preferably has improved accumulation of succinic acid as compared to those strains.

Examples of acetyl-CoA hydrolase having the above-mentioned activity include a protein having an amino acid sequence of SEQ ID NO: 45. In addition, it may be a protein having an amino acid sequence of SEQ ID NO: 45 including a substitution, deletion, insertion or addition of one or several amino acids as long as it has an acetyl-CoA hydrolase activity. Here, for example, the term "several" means 2 to 20, preferably 2 to 10, more preferably 2 to 5.

The term "modified so that the acetyl-CoA hydrolase activity is decreased" includes decrease in the number of molecules of acetyl-CoA hydrolase per cell, decrease in the acetyl-CoA hydrolase activity per molecule, and the like. Specifically, it is achieved by inactivating a gene encoding acetyl-CoA hydrolase on a chromosome, modification of an expression regulatory sequence such as promoter or Shine-Dalgarno (SD) sequence, or the like. Examples of acetyl-CoA hydrolase gene on a chromosome include a DNA having a nucleotide sequence of nucleotide numbers 1037-2542 of SEQ ID NO: 44. It may be a DNA that hybridizes with the nucleotide sequence of nucleotide numbers 1037-2542 of SEQ ID NO: 44 or a probe that can be prepared from the nucleotide sequence under stringent conditions as long as it encodes a protein having acetyl-CoA hydrolase activity. The term "stringent conditions" means conditions in which so-called specific hybrid is formed and non-specific hybrid is not formed. It is difficult to clearly define the conditions by numeric value, but examples thereof include conditions comprising washing twice or three times at salt concentration corresponding to 1×SSC, 0.1% SDS, preferably 0.1×SSC, 0.1% SDS at 60° C.

The acetyl-CoA hydrolase gene (hereinafter, referred to as ach gene) can be cloned by synthesizing synthetic oligonucleotides based on a sequence of *Corynebacterium glutamicum* registered in GenBank (NCg12480 of GenBank Accession No. NC_003450 (complementary strand of 2729376 . . . 2730884 of NC_003450)), and performing PCR using a chromosome of *Corynebacterium glutamicum* as a template. Furthermore, there may also be used a sequence of a coryneform bacterium such as *Brevibacterium lactofermentum* having a nucleotide sequence determined by recent genome project. Chromosomal DNA can be prepared from a bacterium as a DNA donor by, for example, a method of Saito and Miura (U. Saito and K. Miura, Biochem. Biophys. Acta, 72, 619 (1963), Experimental Manual for Biotechnology, edited by The Society for Biotechnology, Japan, p 97-98, Baifukan Co., Ltd., 1992) or the like.

The ach gene thus prepared or a part thereof can be used for gene disruption. A gene to be used for gene disruption only needs to have homology that is enough to cause homologous recombination with an ach gene to be disrupted on a chromosomal DNA of a coryneform bacterium (e.g. a gene having the nucleotide sequence of nucleotide numbers 1037-2542 in SEQ ID NO: 44), so such a homologous gene may also be used. Here, the homology that is enough to cause homologous recombination is preferably not less than 70%, more preferably not less than 80%, further more preferably not less than 90%, particularly preferably not less than 95%. Further, a DNA capable of hybridizing with the above-mentioned gene under stringent conditions can cause homologous recombination. The term "stringent conditions" refers to conditions under which a so-called specific hybrid is formed and non-specific hybrid is not formed. It is difficult to clearly define the conditions by numeric value, but the conditions include, for example, conditions that comprise washing once, preferably twice or three times at salt concentrations corresponding to 1×SSC, 0.1% SDS, preferably 0.1×SSC, 0.1% SDS at 60° C.

For example, by using the above-mentioned gene, a deleted-form of ach gene, which is modified so as not to produce acetyl-CoA hydrolase that normally functions by deleting a partial sequence of the ach gene, is prepared, and a coryneform bacterium is transformed with a DNA containing the gene to cause recombination between the deleted-form of the gene and the gene on a chromosome, to thereby disrupt the ach gene on a chromosome. Such a gene disruption by gene substitution using homologous recombination has already been established, and examples thereof include a method using a linear DNA and a method using a plasmid containing a temperature-sensitive replication origin (U.S. Pat. No. 6,303,383 or JP05-007491A). Further, the above-mentioned gene disruption based on gene substitution using homologous recombination may also be performed using a non-replicating plasmid in a host.

For example, an ach gene on a chromosome of a host can be substituted by a deleted-form of ach gene in accordance with the following procedures. First, a plasmid for recombination is prepared by inserting a temperature-sensitive replication origin, deleted-form of ach gene, sacB gene encoding levansucrase and a marker gene exhibiting resistance to such a antibiotic as chloramphenicol.

Here, sacB gene encoding levansucrase is a gene which is used for efficiently selecting a strain in which a vector portion has been excised from a chromosome (Schafer, A. et al., Gene 145 (1994) 69-73). That is, when levansucrase is expressed in a coryneform bacterium, levan generated by assimilation of sucrose acts lethally on the bacterium, so the bacterium cannot grow. Therefore, if a bacterial strain in which a vector carrying levansucrase remains on a chromosome is cultured on a sucrose-containing plate, it cannot grow. As a result only a bacterial strain from which the vector has been excised can be selected on the sucrose-containing plate.

Genes each having the following sequences can be used as a sacB gene or homologous gene thereof.

*Bacillus subtilis*: sacB GenBank Accession Number X02730 (SEQ ID NO: 35)

*Bacillus amyloliquefaciens*: sacB GenBank Accession Number X52988

*Zymomonas mobilis*: sacB GenBank Accession Number L33402

*Bacillus stearothermophilus*: surB GenBank Accession Number U34874

*Lactobacillus sanfranciscensis*: frfA GenBank Accession Number AJ508391

*Acetobacter xylinus*: lsxA GenBank Accession Number AB034152

*Gluconacetobacter diazotrophicus*: lsdA GenBank Accession Number L41732

A coryneform bacterium is transformed with the above-mentioned recombinant plasmid. The transformation can be performed in accordance with a transformation method which has been previously reported. Examples of the method include, a method of increasing permeability of a DNA by treating cells of a recipient bacterium with calcium chloride as reported for *Escherichia coli* K-12 (Mandel, M. and Higa, A., J. Mol. Biol., 53, 159 (1970)) and, a method of preparing competent cells using proliferating cells for introduction of DNA as reported for *Bacillus subtilis* (Duncan. C. H., Wilson, G. A and Young, F. E, Gene, 1, 153 (1977)). Alternatively, as reported for *Bacillus subtilis*, actinomycetes and yeasts, a method of introducing a recombinant DNA into cells of a DNA recipient bacterium (Chang. S. and Choen, S. N., Molec. Gen. Genet., 168, 111 (1979); Bibb, M. J., Ward, J. M., and Hopwood, O. A., Nature, 274, 398 (1978); Hinnen, A., Hicks, J. B. and Fink, G. R., Proc. Natl. Acad. Sci. USA, 75 1929 (1978)) may also be applied. In addition, a coryneform bacterium may be transformed by the electric pulse method (Sugimoto et al., JP02-207791A).

Examples of a temperature-sensitive plasmid for a coryneform bacterium include p48K and pSFKT2 (JP2000-262288A), and pHSC4 (France Patent No. 2667875 (1992) and JP05-7491A). These plasmids are autonomously replicable in a coryneform bacterium at least at 25° C., but they are not autonomously replicable at 37° C. *Escherichia coli* AJ12571 having pHSC4 has been deposited with an Accession No. FERM P-11763 at National Institute of Bioscience and Human-Technology, Agency of industrial Science and Technology, Ministry of International Trade and Industry (currently, International Patent Organism Depositary, National Institute of Advanced Industrial Science and Technology) (Central 6, 1-1-1 Higashi, Tsukuba, Ibaraki, 305-5466 Japan) on Oct. 11, 1990, and then transferred to an international deposit under the provisions of Budapest Treaty on Aug. 26, 1991 with an Accession No. FERM BP-3524.

A transformant obtained as described above is cultured at a temperature at which the temperature-sensitive replication origin does not function (25° C.), to thereby obtain a strain into which the plasmid has been introduced. The plasmid-introduced strain is cultured at high temperature to excise the temperature-sensitive plasmid, and the bacterial strain is applied onto a plate containing an antibiotic. The temperature-sensitive plasmid cannot replicate at high temperature. Therefore, a bacterial strain from which the plasmid has been excised cannot grow on a plate containing an antibiotic, but a bacterial strain in which recombination has occurred between the ach gene on the plasmid and the ach gene on a chromosome appears at a very low frequency.

In the strain obtained by introducing the recombinant DNA into a chromosome as described above, recombination occurs with an ach gene sequence that is originally present on a chromosome, and two fusion genes of the chromosomal ach gene and the deleted-form of ach gene are inserted into a chromosome so that other portions of the recombinant DNA (vector part, temperature-sensitive replication origin and antibiotic-resistance marker) are present between the fusion genes.

Then, in order to leave only the deleted-form of ach gene on a chromosomal DNA, the gene is eliminated together with the vector portion (the temperature-sensitive replication origin and drug-resistance marker) from the chromosomal. This procedure causes a case where the normal ach gene remains on the chromosomal DNA and the deleted-form of ach gene is excised, or to the contrary, a case where the normal ach gene is excised and the deleted-form of ach gene remains on chromosomal DNA. In both cases, when culture is performed at a temperature that allows a temperature-sensitive replication origin to function, the cleaved DNA is kept in a cell as a plasmid. Next, when culture is performed at a temperature that does not allow a temperature-sensitive replication origin to function, the ach gene on the plasmid is eliminated from the cell together with the plasmid. Then, a strain in which the deleted-form of ach gene remains on the chromosome, is selected by PCR, Southern hybridization, or the like, to thereby yield a strain in which the ach gene is disrupted.

In the case where a plasmid having no replicability in a coryneform bacterium is used instead of the above-mentioned temperature-sensitive plasmid, gene disruption can also be performed in a similar way. The plasmid having no replicability in a coryneform bacterium is preferably a plasmid having a replicability in *Escherichia coli*, and examples thereof include pHSG299 (Takara Bio Inc.) and pHSG399 (Takara Bio Inc.).

Meanwhile, examples of a method of decreasing an activity of acetyl-CoA hydrolase include not only the above-mentioned genetic engineering method but also a method comprising treating a coryneform bacterium with ultraviolet irradiation or with a mutagenesis agent to be generally used for mutation such as N-methyl-N'-nitro-N-nitrosoguanidine (NTG) and nitrous acid, and selecting a bacterial strain having decreased acetyl-CoA hydrolase activity.

In the present invention, it is more effective to use a bacterial strain modified so that either or both of activities of phosphotransacetylase (hereinafter, referred to as PTA) and acetate kinase (hereinafter, referred to as ACK) are decreased in addition to the decrease in the ACH activity.

In the present invention, phosphotransacetylase (PTA) activity means an activity to catalyze a reaction to generate acetyl phosphate by transferring phosphate to acetyl-CoA (EC:2.3.1.8), and acetate kinase (ACK) means an activity to catalyze a reaction to generate acetic acid from acetyl phosphate and ADP (EC:2.7.2.1).

Decreasing these activities may be accomplished by disruption of genes encoding the above-mentioned enzymes, or by modification of an expression regulatory sequence such as a promoter and Shine-Dalgarno (SD) sequence of the genes encoding the enzymes, Gene disruption can be performed in the same way as the above-mentioned method of disrupting the ach gene.

As genes encoding the enzymes, for example, the following genes of *Corynebacterium glutamicum* deposited in GenBank may be used:

pta (phosphoacetyltransferase) gene: GenBank Accession No. NCgl2657 (complementary strand of nucleotide numbers 2936506-2937495 in NC_003450) (the nucleotide numbers 956-1942 in SEQ ID NO: 39)

ack (acetate kinase) gene: GenBank Accession No. NCgl2656 (complementary strand of nucleotide numbers 2935313-2936506 in NC_003450) (the nucleotide numbers 1945-3135 in SEQ ID NO: 39).

The phrase "phosphotransacetylase (hereinafter, referred to as PTA) activity is decreased" means that PTA activity is decreased as compared to a PTA-unmodified strain. The PTA activity is decreased than PTA-unmodified strain or a wild-type strain, and it is preferably decreased to 50% or less per bacterial cell, more preferably 10% or less per bacterial cell. The PTA activity may be completely eliminated. The decrease in PTA activity can be confirmed by determining the PTA activity by a method of Klotzsch et al. (Klotzsch H. R., Meth Enzymol. 12, 381-386 (1969)). A coryneform bacterium in which activities of both of ACH and PTA are decreased can be obtained by constructing a coryneform bacterium having decreased ACH activity and modifying it so as to decrease PTA activity. However, there is no preference in the order for performing the modification to decrease PTA activity and the modification to decrease ACH activity.

The phrase "acetate kinase (hereinafter, referred to as ACK) activity is decreased" means that ACK activity is decreased as compared to a wild-type strain or an ACK-unmodified strain. The ACK activity is decreased than ACK-unmodified strain or a wild-type strain, and it is preferably decreased to 50% or less per bacterial cell, more preferably 10% or less per bacterial cell as compared to an ACK-unmodified strain. ACK activity may be completely eliminated. The decrease in ACK activity can be confirmed by determining the ACK activity by a method of Ramponi et al. (Ramponi G., Meth. Enzymol. 42, 409-426 (1975)). A coryneform bacterium in which activities of both of ACH and ACK are decreased can be obtained by constructing a coryneform bacterium having decreased ACH activity and modifying it so as to decrease ACK activity. However, there is no preference in the order for performing the modification to decrease ACK activity and the modification to decrease ACH activity.

In the present invention, it is more effective to use a bacterial strain modified so that a lactate dehydrogenase (hereinafter, referred to as LDH) activity is decreased in addition to decrease in the above-mentioned ACH activity. The lactate dehydrogenase activity means an activity to catalyze a reaction to generate lactic acid by reducing pyruvic acid using NADH as a coenzyme. The phrase "lactate dehydrogenase activity is decreased" means that LDH activity is decreased as compared to an LDH-unmodified strain. The LDH activity is decreased than an LDH-unmodified strain or a wild-type strain, and it is preferably decreased to 50% or less per bacterial cell, preferably 10% or less per bacterial cell. LDH activity may be completely eliminated. The decrease in LDH activity can be confirmed by determining the LDH activity by a method of L. Kanarek et al. (L. Kanarek and R. L. Hill, J. Biol. Chem. 239, 4202 (1964)). A coryneform bacterium of the present invention can be obtained by preparing a coryneform bacterium having decreased LDH activity and modifying it so as to decrease ACH activity. However, there is no preference in the order for performing the modification to decrease LDH activity and the modification to decrease ACH activity.

As an ldh gene, there may be used, for example, a gene having a sequence represented by SEQ ID NO: 37, and gene disruption may be performed in a similar manner as in the case of the above-mentioned ach gene.

Furthermore, in the present invention, there may be used a bacterium modified so that an activity of pyruvate carboxylase (hereinafter, referred to as PC) is increased in addition to decrease in ACH activity. The term "pyruvate carboxylase activity is increased" means that PC activity is increased as compared to a wild-type strain or an unmodified strain such as a parent strain. PC activity can be determined by a method of Peters-Wendisch P. G et al. (Peters-Wendisch P. G. et al. Microbiology 143, 1095-1103 (1997)).

As a PC gene encoding a PC protein to be used in the method of the present invention, there may be employed a gene whose nucleotide sequence has been determined, or a gene obtained by isolating a DNA fragment that encodes a protein having PC activity from a chromosome of microorganisms, animals, plants, or the like according to the method described below and determining its nucleotide sequence. Further, after determination of the nucleotide sequence, a gene synthesized based on the sequence may be used. For example, there may be used a pyruvate carboxylase gene of *Corynebacterium glutamicum* ATCC13032 (GenBank Accession No. NCgl0659 gene: SEQ ID NO: 46). Further, there may also be used PC genes derived from the following organisms.

Human [Biochem. Biophys. Res. Comm., 202, 1009-1014, (1994)]
Mouse [Proc. Natl. Acad. Sci. USA., 90, 1766-1779, (1993)]
Rat [GENE, 165, 331-332, (1995)]
Yeast; *Saccharomyces cerevisiae* [Mol. Gen. Genet., 229, 307-315, (1991)]*Schizosaccharomyces pombe* [DDBJ Accession No.; D78170]
*Bacillus stearothermophilus* [GENE, 191, 47-50, (1997)]
*Rhizobium etli* [J. Bacteriol., 178, 5960-5970, (1996)]

A DNA fragment containing a PC gene can be expressed by inserting the DNA fragment into a suitable expression plasmid such as pUC118 (Takara Bio Inc.), and introducing into a suitable host microorganism such as *Escherichia coli* JM109 (Takara Bio Inc.). The expressed PC gene product, which is pyruvate carboxylase, can be confirmed by determining PC activity by the known method as described above in the transformant, and then comparing the determined PC activity with PC activity of a crude enzyme solution extracted from a non-transformant strain. The DNA fragment containing PC gene is inserted into a suitable plasmid such as a plasmid vector containing at least a gene responsible for replication function of the plasmid in coryneform bacteria, thereby a recombinant plasmid capable of highly expressing PC in coryneform bacteria can be obtained. Here, in the recombinant plasmid, a promoter for expression of PC gene may be a promoter of coryneform bacteria. However, it is not limited to such a promoter; and any promoter can be used as long as it has a nucleotide sequence capable of initiating transcription of PC gene.

Plasmid vectors, into which PC gene can be introduced, are not limited as long as they contain at least a gene responsible for replication function in coryneform bacteria. Specific examples thereof include: plasmid pCRY30 described in JP03-210184A; plasmids pCRY2I, pCRY2KE, pCRY2KX, pCRY31, pCRY3KE, and pCRY3KX each described in JP02-72876A and U.S. Pat. No. 5,185,262; plasmids pCRY2 and pCRY3 each described in JP01-191686A; pAM330 described in JP58-67679A; pHM1519 described in JP58-77895A; pAJ655, pAJ611, and pAJ1844 each described in JP58-192900A; pCG1 described in JP57-134500A; pCG2 described in JP58-35197A; and pCGG4 and pCG11 each described in JP57-183799A.

Of those, plasmid vectors used in host-vector system for coryneform bacteria are preferably those having a gene responsible for replication function of the plasmid in coryneform bacteria and a gene responsible for stabilization function of the plasmid in coryneform bacteria. For instance, plasmids pCRY30, pCRY2I, pCRY2KE, pCRY2KX, pCRY31, pCRY3KE, and pCRY3KX can be preferably used.

Coryneform bacteria having enhanced PC gene expression can be obtained by transforming a coryneform bacterium, for example, *Brevibacterium lactofermentum* 2256 strain (ATCC13869) with a recombinant vector prepared by inserting PC gene into an appropriate site of a plasmid vector which is replicable in aerobic coryneform bacteria as described above. Transformation can be carried out by, for example, the electric pulse method (Res. Microbiol., Vol. 144, p. 181-185, 1993). PC activity can also be increased by enhancing gene expression by introduction, substitution, amplification or the like of PC gene on a chromosome by a known homologous recombination method. By disrupting the ach gene in a strain which highly expresses the PC gene, a bacterial strain with enhanced PC activity and decreased ACH activity can be obtained. There is no preference in the order for performing modifications to decrease ACH activity and to enhance PC activity.

Moreover, in the present invention, a bacterium that has been modified so that activity of ACH, or activities of ACH, PTA and ACK is/are decreased, and further modified so that LDH activity is decreased and PC activity is increased, is particularly effectively used for production of a substance, especially for production of succinic acid.

<3> Production of Succinic Acid Using the Bacterium of the Present Invention

Succinic acid can be efficiently produced by culturing the thus obtained coryneform bacterium in a medium to produce and accumulate succinic acid in the medium and collecting succinic acid from the medium.

Upon use of the above-mentioned bacterium in reaction for producing succinic acid, the bacterium subjected to slant culture on such a solid medium as an agar medium may be used directly for the reaction, but a bacterium obtained by culturing the above-mentioned bacterium in a liquid medium (seed culture) in advance may be preferably used. Succinic acid may be produced by allowing the seed-cultured bacterium to react with an organic material while the bacterium is proliferating in a medium containing the organic raw material. In addition, succinic acid can also be produced by harvesting bacterial cells which has been proliferated and then reacting the bacterial cells with an organic raw material in reaction liquid containing the organic raw material. Further, for the purpose of using an aerobic coryneform bacterium in the method of the present invention, it is preferable to use the aerobic coryneform bacterium for the reaction after culturing the bacterium under a normal aerobic condition. The medium to be used for culture may be any medium normally used for culturing microorganisms. For instance, conventional media, which can be prepared by adding natural nutrient sources such as meat extract, yeast extract and peptone to a composition made of inorganic salts such as ammonium sulfate, potassium phosphate and magnesium sulfate, can be used. In the case of harvesting and using the bacterial cells after culture, the bacterial cells are harvested by centrifugation, membrane separation, or the like, and then used for the reaction.

In the present invention, a treated product of bacterial cells can also be used. For instance, the treated products of bacterial cells include immobilized bacterial cells which are immobilized on acrylamide, carrageenan or the like, disrupted bacterial cells, centrifugal supernatant thereof, or fractions obtained by partially purifying the supernatant with an ammonium sulfate treatment or the like.

An organic raw material to be used for the production method of the present invention is not particularly limited as long as it is a carbon source which can be assimilated by the microorganism described herein to produce succinic acid. In general, there is used a fermentable carbohydrate including: a carbohydrate such as galactose, lactose, glucose, fructose, glycerol, sucrose, saccharose, starch and cellulose; polyalcohol such as glycerin, mannitol, xylitol and ribitol. Of those, glucose, fructose and glycerol are preferable, and glucose is particularly preferable.

In addition, a saccharified starch liquid, molasses and the like, which contain any one of the above-mentioned fermentable carbohydrates, can also be used. Any one of those fermentable carbohydrates may be used alone or may be used in combination. The concentration at which the above-mentioned organic raw material is used is not particularly limited, but it is advantageous to increase the concentration as high as possible within the range that does not inhibit the production of succinic acid. The reaction is generally performed under the presence of the organic raw material in the range of 5 to 30% (w/v), preferably 10 to 20% (w/v). The organic raw material may be additionally added according to a decrease in the above-mentioned organic raw material when the reaction progresses.

The reaction liquid containing the organic raw material is not particularly limited. The reaction liquid to be used may be water, buffer, medium or the like, but the medium is most preferable. The reaction liquid is preferably one containing a nitrogen source, inorganic salts and the like. Here, the nitrogen source is not particularly limited as long as it can be assimilated by the microorganism described herein to produce succinic acid. Specific examples of the nitrogen source include various organic and inorganic nitrogen compounds such as ammonium salts, nitrate, urea, soybean hydrolysate, casein hydrolysate, peptone, yeast extract, meat extract, and corn steep liquor. Examples of the inorganic salts include various kinds of phosphoric salts, sulfate salts and metal salts of magnesium, potassium, manganese, iron, zinc, and the like. In addition, components that promote growth of bacterial cells including: vitamins such as biotin, pantothenic acid, inositol and nicotinic acid; nucleotides; and amino acids, may be added if necessary. Further, it is preferable that an appropriate amount of a commercially available antifoaming agent is added to the reaction liquid to suppress foaming at the time of reaction.

pH of the reaction liquid can be adjusted by adding sodium carbonate, sodium bicarbonate, potassium carbonate, potassium bicarbonate, magnesium carbonate, sodium hydroxide, calcium hydroxide, magnesium hydroxide, or the like. The pH for the reaction is usually 5 to 10, preferably 6 to 9.5, so the pH of the reaction liquid is adjusted within the above-mentioned range with an alkaline material, carbonate, urea, or the like during the reaction, if necessary.

The medium preferably contains carbonate ion, bicarbonate ion or carbonic acid gas (carbon dioxide). The carbonate ion or bicarbonate ion is supplied from magnesium carbonate, sodium carbonate, sodium bicarbonate, potassium carbonate, or potassium bicarbonate, which can also be used as a neutralizing agent. However, if necessary, the carbonate ion or bicarbonate ion can also be supplied from carbonic acid or bicarbonic acid, or salts thereof, or carbonic acid gas. Specific examples of the salts of carbonic acid or bicarbonic acid include magnesium carbonate, ammonium carbonate, sodium carbonate, potassium carbonate, ammonium bicarbonate, sodium bicarbonate, and potassium bicarbonate. In addition, the carbonate ion or bicarbonate ion is added at a concentration of 0.001 to 5 M, preferably 0.1 to 3 M, and more preferably 1 to 2 M. When carbonic acid gas is contained, the amount of the carbonic acid gas to be contained is 50 mg to 25 g, preferably 100 mg to 15 g, and more preferably 150 mg to 10 g per liter of the liquid.

The optimal temperature at which the bacterium to be used in the reaction grow is generally in the range of 25° C. to 35° C. On the other hand, the temperature at the time of reaction is generally in the range of 25° C. to 40° C., preferably in the range of 30° C. to 37° C. The amount of bacterial cells to be used in the reaction is not particularly limited, but the amount is adjusted in the range of 1 to 700 g/L, preferably 10 to 500 g/L, and more preferably 20 to 400 g/L. The time period of the reaction is preferably 1 to 168 hours, more preferably 3 to 72 hours.

Upon culture of the bacterium, it is necessary to supply oxygen by aeration and agitation. On the other hand, the reaction for producing succinic acid may be performed with aeration and agitation, or may be performed under an anaerobic condition with neither aeration nor supply of oxygen. Here, the term "anaerobic condition" means that the reaction is conducted while keeping the dissolved oxygen low in the liquid. In this case, it is preferable to carry out the reaction at a dissolved oxygen of 0 to 2 ppm, preferably 0 to 1 ppm, and more preferably 0 to 0.5 ppm. For that purpose, there may be used a method in which a vessel is hermetically sealed to carry out the reaction without aeration; a method in which an inert gas such as a nitrogen gas is supplied to carry out the reaction; a method in which aeration with an inert gas containing carbonic acid gas is performed; and the like.

Succinic acid accumulated in the reaction liquid (culture solution) can be isolated and purified from the reaction liquid according to a conventional procedure. To be specific, succinic acid can be isolated and purified by removing solid materials including bacterial cells through centrifugation, filtration or the like, and desalting the solution with an ion exchange resin or the like, followed by crystallization or column chromatography from the solution.

In the present invention, after production of succinic acid by the method of the present invention as described above, a polymerization reaction is carried out using the obtained succinic acid as a raw material to produce a succinic acid-containing polymer. The succinic acid-containing polymer may be a homopolymer or a copolymer with other polymer raw materials. In recent years, environment-friendly industrial products are on the increase, and polymers prepared by using raw materials of a plant origin have been attracting attention. The succinic acid to be produced in the present invention can be processed into polymers such as polyester and polyamide and then used. Specific examples of the succinic acid-containing polymer include a succinic acid-containing polyester obtained through polymerization between a diol such as butanediol or ethylene glycol and succinic acid, and a succinic acid-containing polyamide obtained through polymerization between a diamine such as hexamethylenediamine and succinic acid.

Further, succinic acid or a composition containing succinic acid which can be obtained by the production method of the present invention can be used as food additives, pharmaceuticals, cosmetics, and the like.

EXAMPLES

Hereinafter, the present invention will be described in further detail with reference to examples.

Example 1

<1> Construction of a Disruption Vector Carrying sacB Gene (A) Construction of pBS3

The sacB gene (SEQ ID NO: 35) was obtained by PCR using a chromosomal DNA of *Bacillus subtilis* as a template and SEQ ID NOS: 1 and 2 as primers. PCR was carried out using LA Taq (Takara Bio Inc.) in such a way that one cycle of heat-retention at 94° C. for 5 minutes was performed and then a cycle of denaturation at 94° C. for 30 seconds, annealing at 49° C. for 30 seconds and elongation at 72° C. for 2 minutes was repeated 25 cycles. The PCR product thus obtained was purified by a conventional procedure and then digested with BglII and BamHI, followed by blunt-ending. The fragment was inserted into a site of pHSG299 which had been digested with AvaII and blunt-ended. Competent cells of *Escherichia coli* JM109 (Takara Bio Inc.) were used for transformation with this DNA and the transformed cells were applied on an LB medium containing 25 μg/ml kanamycin (hereinafter, abbreviated as Km), followed by overnight culture. Subsequently, appeared colonies were picked up, and single colonies were isolated, thereby transformants were obtained. Plasmids were extracted from transformants, and a plasmid into which a PCR product of interest was inserted was named pBS3. FIG. 1 shows the construction procedures of pBS3.

(B) Construction of pBS4S

SmaI site in the kanamycin resistance gene sequence present on pBS3 was disrupted by crossover PCR-mediated nucleotide substitution causing no amino acid substitution to obtain a plasmid. First, PCR was carried out using pBS3 as a template and synthetic DNAs of SEQ ID NOS: 3 and 4 as primers, thereby amplified product of N-terminal region of the kanamycin resistance gene was obtained. On the other hand, to obtain amplified product of C-terminal region of the Km resistance gene, PCR was carried out using pBS3 as a template and synthetic DNAs of SEQ ID NOS: 5 and 6 as primers. The PCR was carried out using Pyrobest DNA Polymerase (Takara Bio Inc.) in such a way that one cycle of heat-retention at 98° C. for 5 minutes was performed and then a cycle of denaturation at 98° C. for 10 seconds, annealing at 57° C. for 30 seconds and elongation at 72° C. for 1 minute was repeated 25 cycles, to thereby yield a PCR product of interest. SEQ ID NOS: 4 and 5 are partially complementary to each other, and the SmaI site in the sequence is disrupted by nucleotide substitution causing no amino acid substitution. Next, to obtain a fragment of a mutant kanamycin resistance gene in which the SmaI site is disrupted, the gene products of the N-terminal and C-terminal regions of the above-mentioned kanamycin resistance gene were mixed at an approximately equimolar concentration, and PCR was carried out using the mixture of the gene products as templates and synthetic DNAs of SEQ ID NOS: 3 and 6 as primers, to thereby yield amplified product of a mutation-introduced Km resistance gene. PCR was carried out using Pyrobest DNA Polymerase (Takara Bio Inc.) in such a way that one cycle of heat-retention at 98° C. for 5 minutes was performed and then a cycle of denaturation at 98° C. for 10 seconds, annealing at 57° C. for 30 seconds and elongation at 72° C. for 1.5 minutes was repeated 25 cycles, to thereby yield a PCR product of interest.

Figure 2:
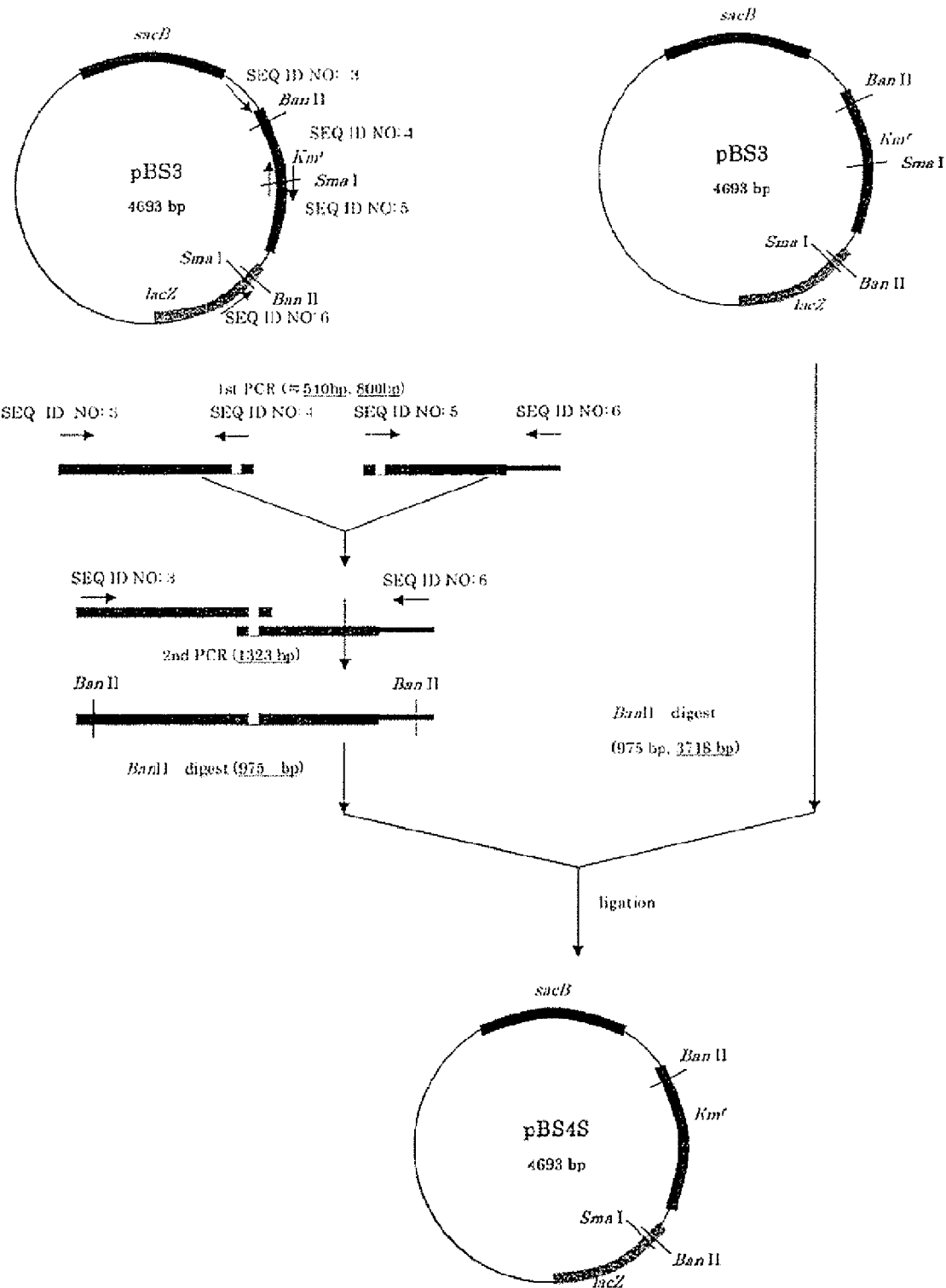
FIG. 2 shows the procedures for constructing plasmid pBS4S.

The PCR product was purified by a conventional procedure and then digested with BanII, followed by insertion into BanII site of the above-mentioned pBS3. Competent cells of *Escherichia coli* JM109 (Takara Bio Inc.) were used for transformation with this DNA and transformed cells were applied on an LB medium containing 25 μg/ml of kanamycin, followed by overnight culture. Subsequently, appeared colonies were picked up, and single colonies were isolated, thereby transformants were obtained. Plasmids were extracted from the transformants, and a plasmid into which a PCR product of interest was inserted was named pBS4S. FIG. 2 shows the construction procedures of pBS4S.

(C) Construction of pBS5T

Figure 3:
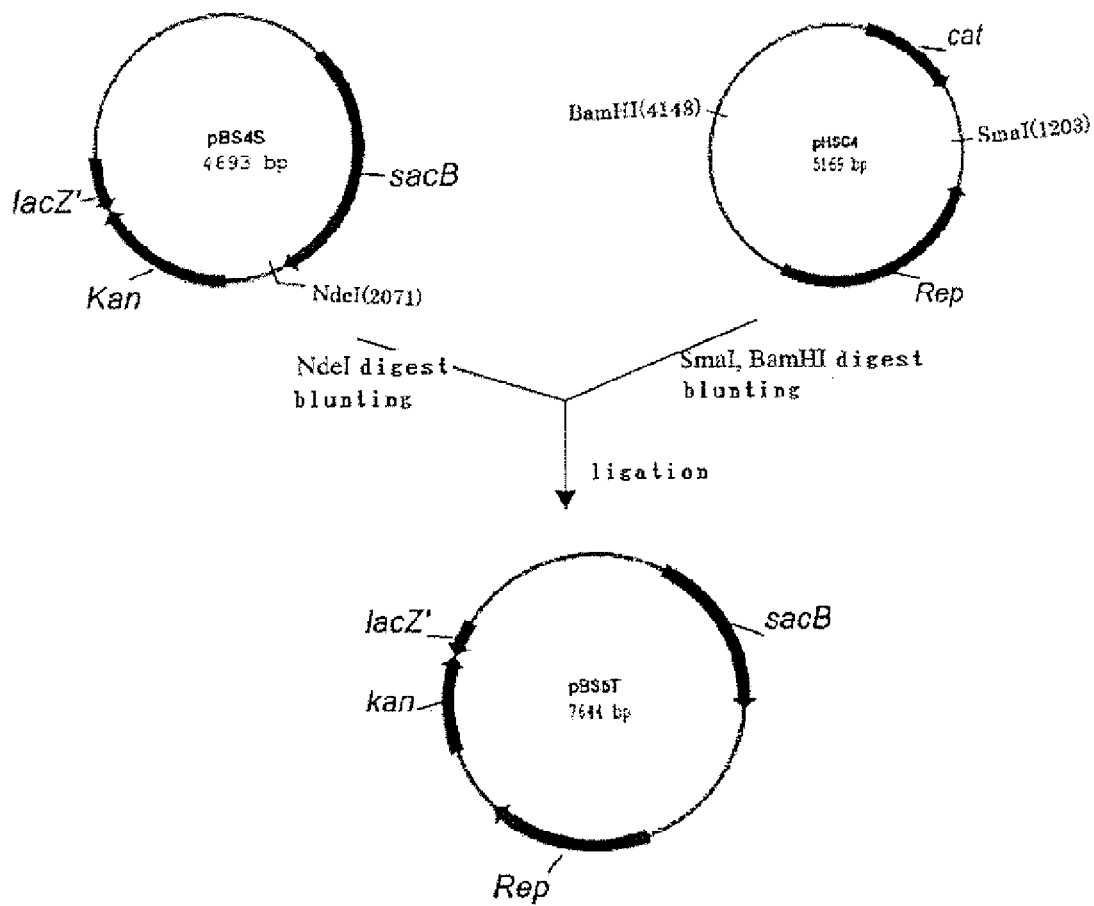
FIG. 3 shows the procedures for constructing plasmid pBS5T.

A plasmid was constructed by inserting a temperature-sensitive replication origin for a coryneform bacterium into pBS4S constructed in the above-mentioned (B). That is, a temperature-sensitive replication origin for a coryneform bacterium was obtained by digesting pHSC4 (JP05-7491 A) with BamHI and SmaI, followed by blunt-ending, and the temperature-sensitive replication origin was inserted into a blunt-ended NdeI site of pBS4S. Competent cells of *Escherichia coli* JM109 (Takara Bio Inc.) were used for transformation with this DNA and transformed cells were applied on an LB medium containing 25 µg/ml of Km, followed by overnight culture. Subsequently, appeared colonies were picked up, and single colonies were isolated, thereby transformants were obtained. Plasmids were extracted from the transformants, and a plasmid into which a PCR product of interest was inserted was named pBS5T. FIG. 3 shows the construction procedures of pBS5T.

Example 2

Construction of LDH Gene-Disrupted Strain (A) Cloning of a Fragment for Disrupting Lactate Dehydrogenase Gene A fragment of a lactate dehydrogenase gene (hereinafter; abbreviated as ldh gene) derived from *Brevibacterium lactofermentum* 2256 strain in which ORF thereof was deleted was obtained by crossover PCR using as primers synthetic DNAs designed based on the nucleotide sequence (SEQ ID NO: 37) of the gene of *Corynebacterium glutamicum* ATCC13032 (GenBank Database Accession No. NC_003450), which has already been disclosed. That is, PCR was carried out by a conventional procedure using a chromosomal DNA of *Brevibacterium lactofermentum* 2256 strain as a template and synthetic DNAs of SEQ ID NOS: 7 and 8 as primers, thereby amplified product of the N-terminal region of the ldh gene was obtained. On the other hand, to obtain amplified product of the C-terminal region of the ldh gene, PCR was carried out by a conventional procedure using a genomic DNA of *Brevibacterium lactofermentum* 2256 as a template and synthetic DNAs of SEQ ID NOS: 9 and 10 as primers. SEQ ID NO: 8 and 9 are complementary to each other and have structures for deleting the entire sequences of ldh ORF.

*Brevibacterium lactofermentum* 2256 strain is available from the American Type Culture Collection (ATCC) (Address: ATCC, P.O. Box 1549, Manassas, Va. 20108, United States of America).

Figure 4:
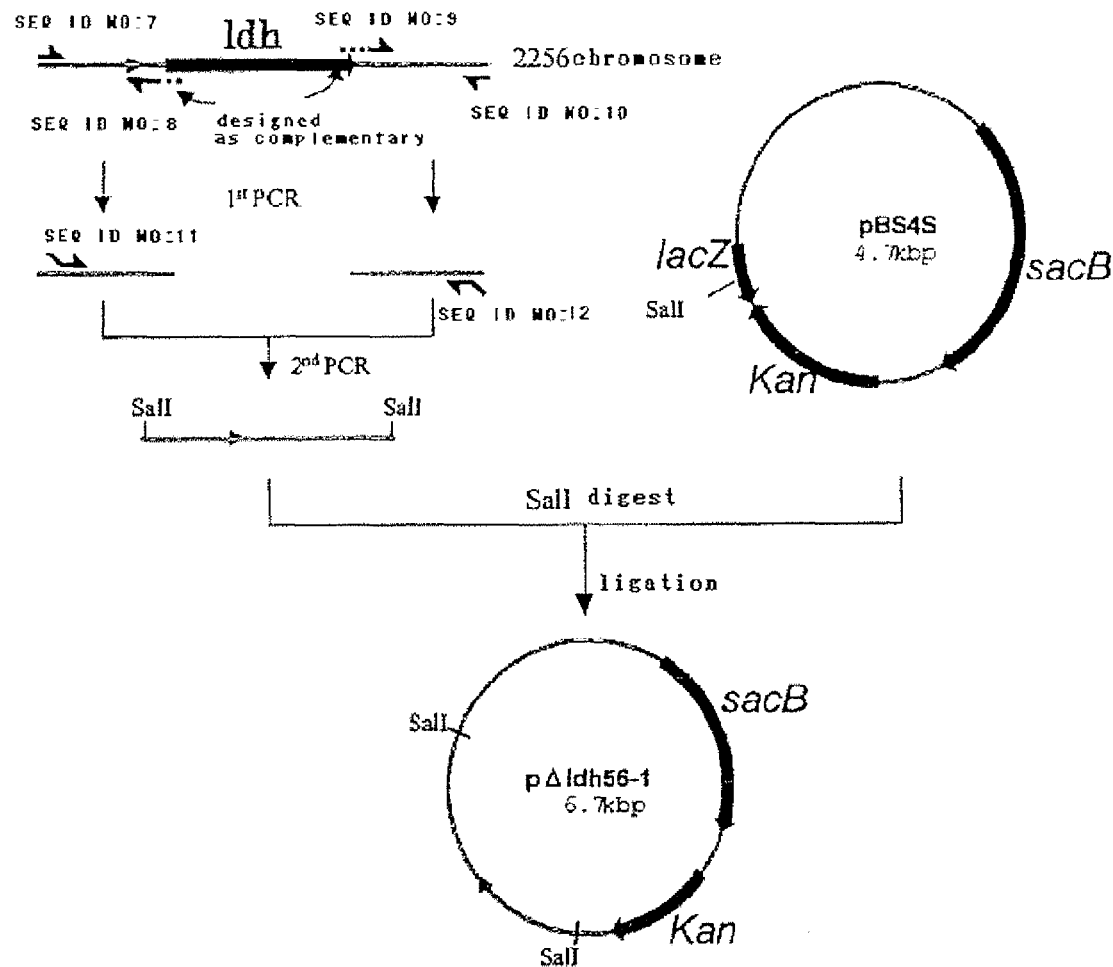
FIG. 4 shows the procedures for constructing plasmid pΔldh56-1.

Next, to obtain a fragment of the ldh gene in which its internal sequence is deleted, the above-mentioned gene products of the N-terminal and C-terminal regions of ldh were mixed at an approximately equimolar concentration, and PCR was carried out by a conventional procedure using the mixture of the gene products as templates and synthetic DNAs of SEQ ID NOS: 11 and 12 as primers, to thereby yield amplified product of the mutation-introduced ldh gene. The PCR product thus obtained was purified by a conventional procedure and then digested with SalI, followed by insertion into SalI site of the above-mentioned pBS4S. Competent cells of *Escherichia coli* JM109 (Takara Bio Inc.) were used for transformation with this DNA and transformed cells were applied on an LB medium containing 100 µM of IPTG, 40 µg/ml of X-Gal, and 25 µg/ml of Km, followed by overnight culture. Subsequently, appeared white colonies were picked up, and single colonies were isolated, thereby transformants were obtained. Plasmids were extracted from the transformants, and a plasmid into which a PCR product of interest was inserted was named pΔldh56-1. FIG. 4 shows the construction procedures of the plasmid.

(B) Preparation of ldh-Disrupted Strain

The pΔldh56-1 obtained by the above-mentioned (A) does not contain a region that enables autonomous replication in a cell of a coryneform bacterium. Therefore, when a coryneform bacterium is transformed with this plasmid, a strain in which the plasmid is integrated into a chromosome by homologous recombination appears at a very low frequency as a transformant. *Brevibacterium lactofermentum* 2256 strain was transformed using a high concentration of the plasmid pΔldh56-1 by the electric pulse method, and the transformed cells were applied on CM-Dex medium (5 g/L of glucose, 10 g/L of polypeptone, 10 g/L of yeast extract, 1 g/L of $KB_2PO_4$, 0.4 g/L of $MgSO_4 \cdot 7H_2O$, 0.01 g/L of $FeSO_4 \cdot 7H_2O$, 0.01 g/L of $MnSO_4 \cdot 7H_2O$, 3 g/L of urea, 1.2 g/L of soybean hydrolysate, pH 7.5 (KOH)) containing 25 µg/ml of kanamycin, followed by culture at 31.5° C. for about 30 hours. A strain grown on the medium contains the kanamycin resistance gene and sacB gene which are derived from the plasmid on the genome, as a result of homologous recombination between the ldh gene fragment on the plasmid and the ldh gene on a genome of *Brevibacterium lactofermentum* 2256 strain.

Next, the single cross-over recombinant was cultured at 31.5° C. overnight in CM-Dex liquid medium not containing kanamycin, and after suitable dilution, it was applied on 10% sucrose-containing Dex-S10 medium (100 g/L of sucrose, 10 g/L of polypeptone, 10 g/L of yeast extract, 1 g/L of $KH_2PO_4$, 0.4 g/L of $MgSO_4 \cdot 7H_2O$, 0.01 g/L of $FeSO_4 \cdot 7H_2O$, 0.01 g/L of $MnSO_4 \cdot 4H_2O$, 3 g/L of urea, 1.2 g/L of soybean hydrolysate, 10 µg/L of biotin, pH 7.5 (KOH)) not containing kanamycin, followed by culture at 31.5° C. for about 30 hours. As a result, about 50 strains, which were considered to become sucrose-insensitive due to elimination of the sacB gene by second homologous recombination, were obtained.

The strains thus obtained include: a strain in which ldh gene was replaced by the mutant type derived from pΔldh56-1; and a strain in which ldh gene reverted to the wild type. Whether the ldh gene is the mutant type or the wild type can be confirmed easily by directly subjecting the bacterial strains obtained by culturing on Dex-S10 agar medium to PCR and detecting their ldh gene. In PCR analysis using primers (SEQ ID NOS: 7 and 10) for amplifying ldh gene, a strain which yielded a PCR product having a smaller size than that of a product obtained by PCR using a chromosomal DNA of the 2256 strain as a template was defined as an ldh-disrupted strain and used in the following experiments. As a result of the analysis of the sucrose-insensitive strains by the above-mentioned method, a strain carrying only the mutant type gene was selected and named 2256Δ(ldh) strain. Also, the strain was used as a parent strain of the following acetic acid-biosynthetic gene-disrupted strain.

Example 3

Construction of Acetate Kinase Gene-Disrupted Strain (A) Cloning of a Fragment for Disrupting Acetate Kinase Gene A fragment of an acetate kinase gene (hereinafter, abbreviated as ack) of *Brevibacterium lactofermentum* 2256 strain in which ORF thereof was deleted was obtained by crossover PCR using as primers synthetic DNAs designed based on the nucleotide sequence (1945-3135 in SEQ ID NO: 39) of the gene of *Corynebacterium glutamicum* ATCC13032 (GenBank Database Accession No. NC_003450), which has already been disclosed. That is, PCR was carried out using a genomic DNA of *Brevibacterium lactofermentum* 2256 strain as a template and synthetic DNAs of SEQ ID NOS: 13 and 14 as primers, thereby amplified product of N-terminal region of the ack gene was obtained. On the other hand, to obtain amplified product of C-terminal region of the ack gene, PCR was carried out using a genomic DNA of *Brevibacterium lactofermentum* 2256 as a template and synthetic DNAs of SEQ ID NOS: 15 and 16 as primers. SEQ ID NO: 14 and 15 are complementary to each other. The PCR was carried out using KOD-plus-(TOYOBO) in such a way that one cycle of heat-retention at 94° C. for 2 minutes was performed and then, for the N-terminal region, a cycle of denaturation at 94° C. for 10 seconds, annealing at 55° C. for 30 seconds and elongation at 68° C. for 30 seconds, and for the C-terminal region, a cycle of denaturation at 94° C. for 10 seconds, annealing at 55° C. for 30 seconds and elongation at 68° C. for 2 minutes, were repeated 30 cycles, respectively. Next, to obtain a fragment of the ack gene in which its internal sequence is deleted, the above-mentioned gene products of the N-terminal and C-terminal regions of ack were mixed at an approximately equimolar concentration, and PCR was carried out using the mixture of the gene products as templates and synthetic DNAs of SEQ ID NOS: 17 and 18 as primers, to thereby yield amplified product of the mutation-introduced ack gene. The PCR was carried out using KOD-plus-(TOYOBO) in such a way that one cycle of heat-retention at 94° C. for 2 minutes was performed and then a cycle of denaturation at 94° C. for 10 seconds, annealing at 55° C. for 30 seconds and elongation at 68° C. for 2.5 minutes was repeated 30 cycles, to thereby yield an amplified product of the mutation-introduced ack gene of interest.

Figure 5:
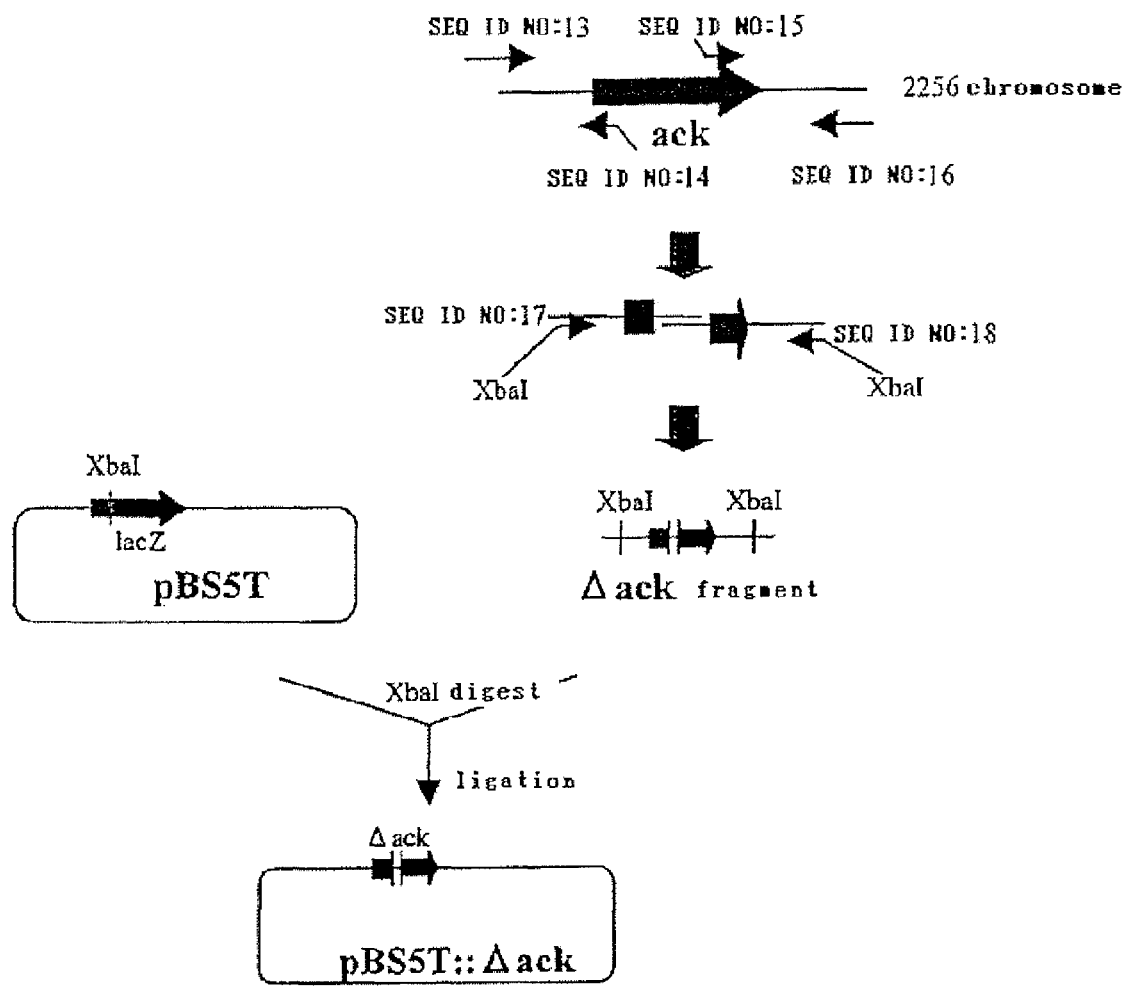
FIG. 5 shows the procedures for constructing plasmid pBS5T::Δack.

The PCR product thus obtained was purified by a conventional procedure and then digested with XbaI, followed by insertion into XbaI site in pBS5T constructed in the above-mentioned Example 1 (C). Competent cells of *Escherichia coli* JM109 (Takara Bio Inc.) were used for transformation with this DNA and transformed cells were applied on an LB medium containing 100 μM of IPTG, 40 μg/ml of X-Gal, and 25 μg/ml of kanamycin, followed by overnight culture. Subsequently, appeared white colonies were picked up, and single colonies were isolated, thereby transformants were obtained. Plasmids were extracted from the transformants, and a plasmid into which a PCR product of interest was inserted was named pBS5T::Δack. FIG. 5 shows the construction procedures of pBS5T::Δack.

(B) Preparation of ack-Disrupted Strain

The replication origin for coryneform bacteria in pBS5T::Δack obtained by the above-mentioned (A) is temperature-sensitive. That is, the plasmid is autonomously replicable in a cell of a coryneform bacterium at 25° C., but it is not autonomously replicable at 31.5° C. (or 34° C.). *Brevibacterium lactofermentum* 2256∴(ldh) strain was transformed using the plasmid by the electric pulse method, and transformed cells were applied on a CM-Dex medium containing 25 μg/ml of kanamycin, followed by culture at 25° C. for 2 nights. Appeared colonies were isolated, to thereby yield transformants. The transformants contain the plasmid. The transformants were cultured at 34° C. overnight in a CM-Dex medium (5 g/L of glucose, 10 g/L of polypeptone, 10 g/L of yeast extract, 1 g/L of $KH_2PO_4$, 0.4 g/L of $MgSO_4 \cdot 7H_2O$, 0.01 g/L of $FeSO_4 \cdot 7H_2O$, 0.01 g/L of $MnSO_4 \cdot 7H_2O$, 3 g/L of urea, 1.2 g/L of soybean hydrolysate, pH 7.5 (KOH)) not containing kanamycin and after suitable dilution, it was applied on a CM-Dex medium containing 25 μg/ml of kanamycin, followed by culture at 34° C. for about 30 hours, The strain grown on the medium contains the kanamycin resistance gene and sacB gene which are derived from the plasmid on the genome, as a result of homologous recombination between the ack gene fragment on the plasmid and the ack gene on the genome of *Brevibacterium lactofermentum* 2256Δ(ldh) strain.

Next, the singe crossover recombinant was cultured at 31.5° C. overnight in CM-Dex liquid medium not containing kanamycin, and after suitable dilution, it was applied on 10% sucrose-containing Dex-S10 medium not containing kanamycin, followed by culture at 31.5° C. for about 30 hours. As a result, about 50 strains which were considered to become sucrose-insensitive due to elimination of the sacB gene by the second homologous recombination, were obtained.

The thus obtained strains include: a strain in which ack gene was replaced by the mutant type derived from pBS5T::Δack; and a strain in which ack gene reverted to the wild type. Whether ack gene is the mutant type or the wild type can be confirmed easily by directly subjecting a bacterial strain obtained through culturing on a Dex-S10 agar medium to PCR and detecting the ack gene. Analysis of the ack gene by using primers (SEQ ID NOS: 13 and 16) for PCR amplification should result in a DNA fragment of 3.7 kb for the wild type and a DNA fragment of 2.5 kb for the mutant type having a deleted region. As a result of the analysis of the sucrose-insensitive strain by the above-mentioned method, a strain carrying only the mutant type gene was selected and named 2256Δ(ldh, ack).

Example 4

Construction of a Strain in which Acetate Kinase Gene and Phosphotransacetylase Gene are Disrupted (A) Cloning of Fragments for Disrupting Acetate Kinase Gene and Phosphotransacetylase Gene The ORFs of acetate kinase gene ("ack") and phosphotransacetylase gene (hereinafter, referred to as pta) of *Brevibacterium lactofermentum* 2256 strain have an operon structure, and both ORFs can be made deficient simultaneously. These gene fragments were obtained by cross-over PCR using as primers synthetic DNAs designed based on the nucleotide sequences of the genes of *Corynebacterium glutamicum* ATCC13032 (GenBank Database Accession No. NC_003450) (pta-ack gene; SEQ ID NO: 39). That is, PCR was carried out using a genomic DNA of *Brevibacterium lactofermentum* 2256 strain as a template, and synthetic DNAs of SEQ ID NOS: 19 and 20 as primers, to thereby yield an amplified product of N-terminal region of the pta gene. On the other hand, to yield an amplified product of C-terminal region of the ack gene, PCR was carried out using a genomic DNA of *Brevibacterium lactofermentum* 2256 strain as a template and synthetic DNAs of SEQ ID NOS: 21 and 16 as primers. SEQ ID NOS: 20 and 21 are partially complementary to each other. PCR was performed by using KOD-plus-(TOYOBO) in such a way that one cycle of heat-retention at 94° C. for 2 minutes was performed and then, for the N-terminal region, a cycle of denaturation at 94° C. for 10 seconds, annealing at 55° C. for 30 seconds and elongation at 68° C. for 30 seconds, and for the C-terminal region, a cycle of denaturation at 94° C. for 10 seconds, annealing at 55° C. for 30 seconds and elongation at 68° C. for 2 minutes, were repeated 30 cycles, respectively.

Figure 6:
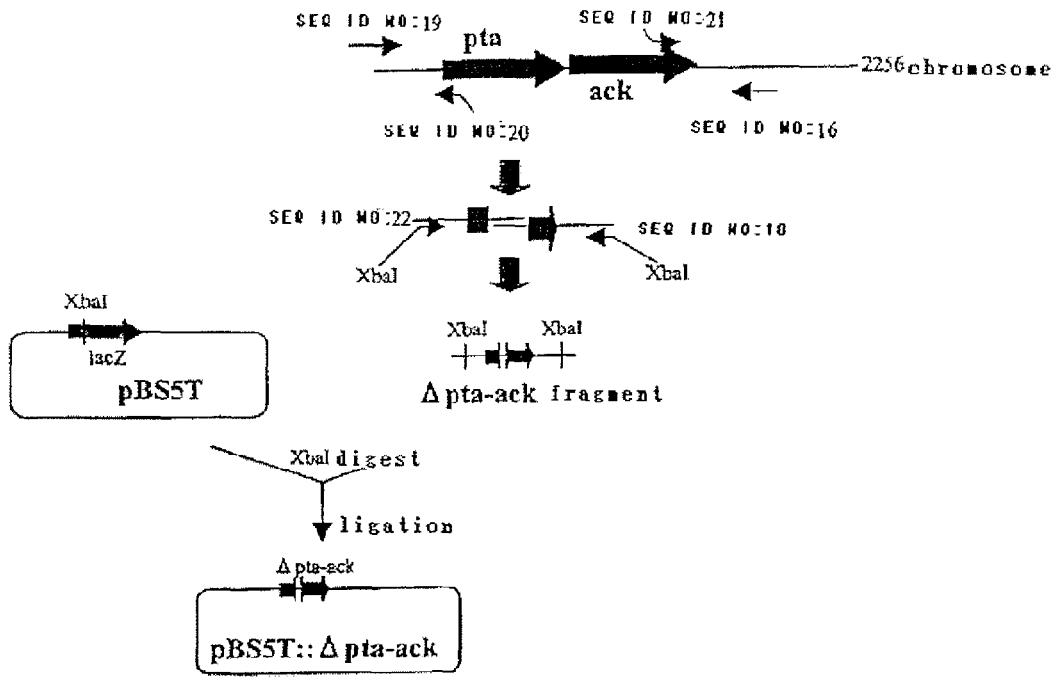
FIG. 6 shows the procedures for constructing plasmid pBS5T::Δpta-ack.

Next, to obtain a fragment of the pta-ack gene in which an internal sequence of pta and ack is deleted, the above-mentioned gene products of the N-terminal region of pta and C-terminal region of ack were mixed at an approximately equimolar concentration, and PCR was carried out using the mixture as templates and synthetic DNAs of SEQ ID NOS: 22 and 18 as primers, to thereby yield amplified product of a mutation-introduced pta-ack gene. The PCR was carried out using KOD-plus-(TOYOBO) in such a way that one cycle of heat-retention at 94° C. for 2 minutes was performed and then a cycle of denaturation at 94° C. for 10 seconds, annealing at 55° C. for 30 seconds, and elongation at 68° C. for 2.5 minutes was repeated 30 cycles, to thereby yield an amplified product of the mutation-introduced pta-ack gene of interest. The PCR product thus obtained was purified by a conventional procedure and then digested with XbaI, followed by insertion into XbaI site of pBS5T. Competent cells of *Escherichia coli* JM109 (Takara Bio Inc.) were used for transformation with this DNA and transformed cells were applied on an LB medium containing 100 μM of IPTG, 40 μg/ml of X-Gal, and 25 μg/ml of kanamycin, followed by overnight culture. Subsequently, appeared white colonies were picked up, and single colonies were then isolated, thereby transformants were obtained. Plasmids were extracted from the transformants, and a plasmid into which a PCR product of interest was inserted was named pBS5T::Δpta-ack. FIG. 6 shows the construction procedures of pBS5T::Δpta-ack.

(B) Preparation of pta-ack-Disrupted Strain

The replication origin for coryneform bacteria in pBSST.:: Δpta-ack obtained by the above-mentioned (A) is temperature-sensitive. That is, the plasmid is autonomously replicable in a cell of a coryneform bacterium at 25° C., but it is not autonomously replicable at 31.5° C. (or 34° C.). *Brevibacterium lactofermentum* 2256Δ(ldh) strain was transformed using the plasmid by the electric pulse method, and transformed cells were applied on a CM-Dex medium containing 25 μg/ml of kanamycin, followed by culture at 25° C. for 2 nights. Appeared colonies were isolated, to thereby yield transformants. The transformants have the plasmid. The transformants were cultured at 34° C. overnight in a CM-flex liquid medium not containing kanamycin, and after suitable dilution, it was applied on a CM-Dex liquid medium containing 25 μg/ml of kanamycin, followed by culture at 34° C. for about 30 hours. The strain grown on the medium contains the kanamycin resistance gene and sacB gene which are derived from the plasmid on the genome, as a result of homologous recombination between the pta-ack gene fragment on the plasmid and the pta-ack gene on genome of *Brevibacterium lactofermentum* 2256Δ(ldh) strain.

Next, the single crossover recombinant was cultured at 31.5° C. overnight in CM-flex liquid medium not containing kanamycin, and after suitable dilution, it was applied on 10% sucrose-containing Dex-S10 medium not containing kanamycin, followed by culture at 31.5° C. for about 30 hours. As a result, about 50 strains, which were considered to become sucrose-insensitive due to elimination of sacB gene by the second homologous recombination, were obtained.

The thus obtained strains include: a strain in which pta and ack genes were replaced by the mutant type derived from pBS5T::Δpta-ack; and a strain in which pta and ack genes were reverted to the wild type. Whether the pta and ack genes are the mutant type or the wild type can be confirmed easily by directly subjecting a bacterial strain obtained through culture on a Dex-S10 agar medium to PCR and detecting the pta and ack genes. Analysis of the pta-ack gene by using primers (SEQ ID NOS: 19 and 16) for PCR amplification should result in a DNA fragment of 5.0 kb for the wild type and a DNA fragment of 2.7 kb for the mutant type having a deleted region.

As a result of the analysis of the sucrose-insensitive strain by the above-mentioned method, a strain carrying only the mutant type gene was selected and named 2256Δ(ldh, pta, ack).

Example 5

Construction of Pyruvate Oxidase Gene-Disrupted Strain (A) Cloning of a Fragment for Disrupting Pyruvate Oxidase Gene A fragment of a pyruvate oxidase gene (hereinafter, abbreviated as poxB) of *Brevibacterium lactofermentum* 2256 strain in which ORF thereof was deleted was obtained by crossover PCR using as primers synthetic DNAs designed based on the nucleotide sequence (SEQ ID NO: 42) of the gene of *Corynebacterium glutamicum* ATCC13032 (GenBank Database Accession No. NC_003450), which has already been disclosed. That is, PCR was carried out using a genomic DNA of *Brevibacterium lactofermentum* 2256 strain as a template and synthetic DNAs of SEQ ID NOS: 23 and 24 as primers, thereby amplified product of N-terminal region of the poxB gene was obtained.

On the other hand, to obtain amplified product of C-terminal region of the poxB gene, PCR was carried out using a genomic DNA of *Brevibacterium lactofermentum* 2256 strain as a template and synthetic DNAs of SEQ ID NOS: 25 and 26 as primers. SEQ ID NOS: 24 and 25 are complementary to each other. The PCR was carried out using KOD-plus-(TOYOBO) in such a way that one cycle of heat-retention at 94° C. for 2 minutes was performed and then a cycle of denaturation at 94° C. for 10 seconds, annealing at 55° C. for 30 seconds and elongation at 68° C. for 40 seconds was repeated 30 cycles for both the N-terminal region and the C-terminal region. Next, to obtain a fragment of poxB gene in which its internal sequence is deleted, the above-mentioned gene products of N-terminal and C-terminal regions of poxB were mixed at an approximate equimolar concentration, and PCR was carried out using the mixture as templates and synthetic DNAs of SEQ ID NOS: 27 and 28 as primers, to thereby yield amplified product of a mutation-introduced poxB gene. The PCR was carried out using KOD-plus-(TOYOBO) in such a way that one cycle of heat-retention at 94° C. for 2 minutes was performed, and then a cycle of denaturation at 94° C. for 10 seconds, annealing at 55° C. for 30 seconds and elongation at 68° C. for 70 seconds was repeated 30 cycles, to thereby yield an amplified product of the mutation-introduced poxB gene of interest.

Figure 7:
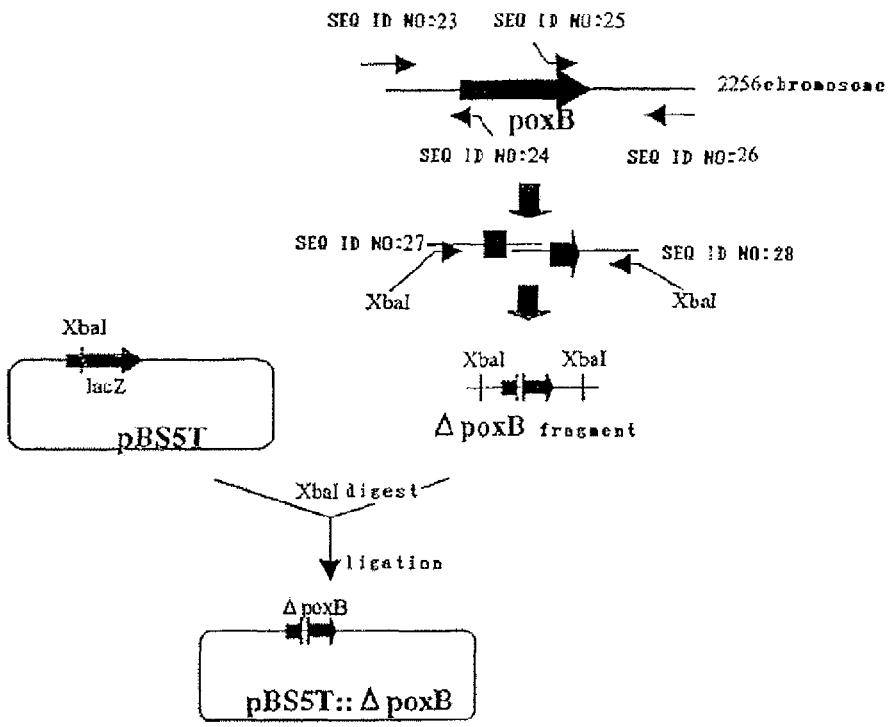
FIG. 7 shows the procedures for constructing plasmid pBS5T::ΔpoxB.

The PCR product thus obtained was purified by a conventional procedure and then digested with XbaI, followed by insertion into XbaI site of pBS5T constructed in Example 1 (C) as described above. Competent cells of *Escherichia coli* JM109 (Takara Bio Inc.) were used for transformation with this DNA and transformed cells were applied on an LB medium containing 100 μM of IPTG; 40 μg/ml of X-Gal, and 25 μg/ml of kanamycin, followed by overnight culture. Subsequently, appeared white colonies were picked up, and single colonies were isolated, thereby transformants were obtained. Plasmids were extracted from the transformants, and a plasmid in which a PCR product of interest was inserted was named pBS5T::ΔpoxB. FIG. 7 shows the construction procedures of pBS5T::ΔpoxB.

(B) Preparation of poxB-Disrupted Strain

The replication origin for coryneform bacteria in pBS5T:: ΔpoxB obtained in Example 5 (A) as described above is temperature-sensitive. That is, the plasmid is autonomously replicable in a cell of a coryneform bacterium at 25° C., but it is not autonomously replicable at 31.5° C. (or 34° C.). *Brevibacterium lactofermentum* 2256Δ(ldh, pta, ack) strain was transformed using the plasmid by the electric pulse method, and the transformed cells were applied on a CM-Dex medium containing 25 µg/ml of kanamycin, followed by culture at 25° C. for 2 nights. Appeared colonies were isolated, to thereby yield transformants. The transformants should have the plasmid.

The transformants were cultured at 34° C. overnight in a CM-Dex liquid medium not containing kanamycin, and after suitable dilution, it was applied on a CM-Dex medium containing 25 µg/ml of kanamycin, followed by culture at 34° C. for about 30 hours. In a strain grown on the medium, the kanamycin resistance gene and sacB gene which are derived from the plasmid are inserted into the genome, as a result of homologous recombination between the poxB gene fragment on the plasmid and the poxB gene on the genome of *Brevibacterium lactofermentum* 2256Δ(ldh, pta, ack) strain. Next, the single crossover recombinant was cultured at 31.5° C. overnight in CM-Dex liquid medium not containing kanamycin, and after suitable dilution, it was applied on 10% sucrose-containing Dex-S10 medium not containing kanamycin, followed by culture at 31.5° C. for about 30 hours. As a result, about 50 strains, which were considered to become sucrose-insensitive due to elimination of sacB gene by the second homologous recombination, were obtained.

The obtained strains include: a strain in which poxB gene was replaced by the mutant type derived from pBS5T::ΔpoxB; and a strain in which poxB gene reverted to the wild type. Whether the poxB gene is the mutant type or the wild type can be confirmed easily by directly subjecting a bacterial strain obtained through culture on a Dex-S10 agar medium to PCR and detecting the poxB gene. A DNA fragment of 2.4 kb for the wild type and a DNA fragment of 1.2 kb for the mutant type having the deleted region can be detected by analysis of the poxB gene with primers (SEQ ID NOS: 23 and 26) for PCR amplification. As a result of the analysis of the sucrose-insensitive strain by the above-mentioned method, a strain carrying only the mutant type gene was selected and named 2256Δ(ldh, pta, ack, poxB).

Example 6

Figure 8:
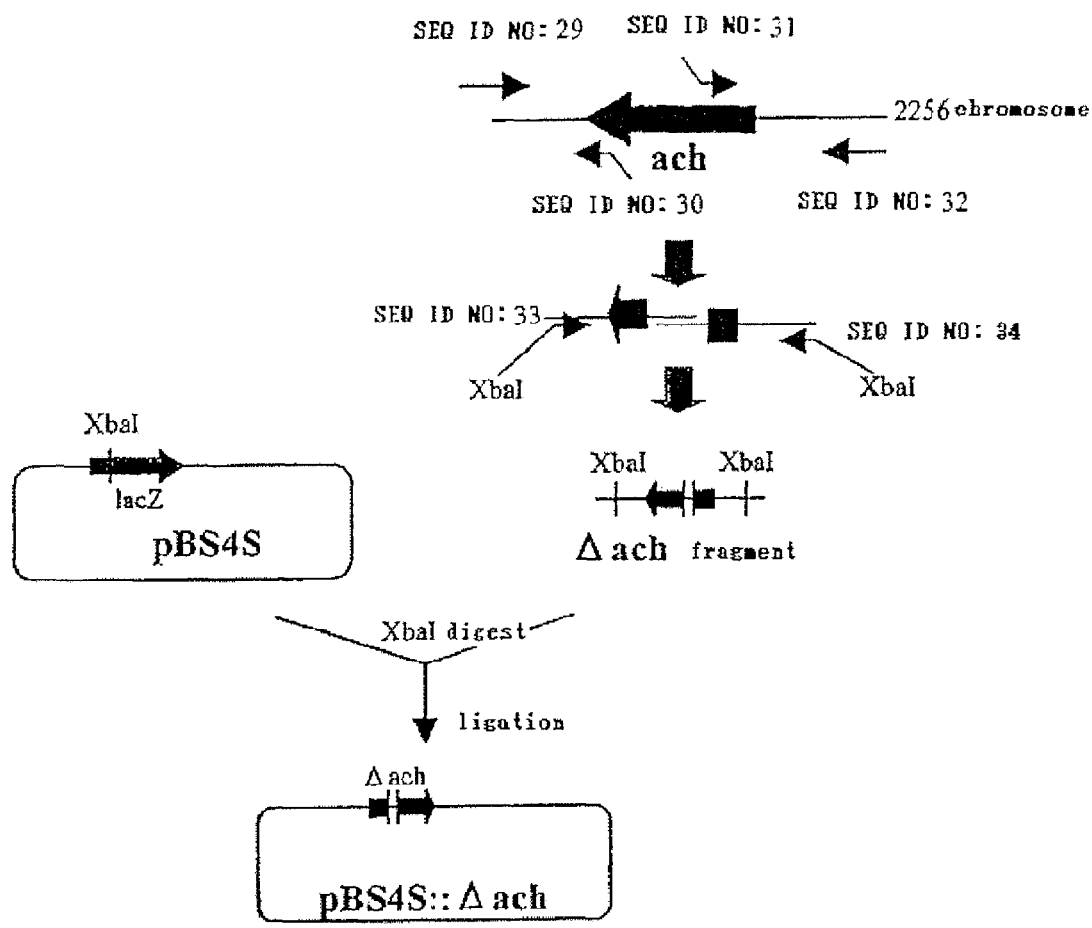
FIG. 8 shows the procedures for constructing plasmid pBS4S::Δach.

Construction of Acetyl-CoA Hydrolase Gene-Disrupted Strain (A) Cloning of a Fragment for Disrupting Acetyl-CoA Hydrolase Gene A fragment of acetyl-CoA hydrolase gene (hereinafter, abbreviated as ach) of *Brevibacterium lactofermentum* 2256 strain in which ORF thereof was deleted was obtained by crossover PCR using as primers synthetic DNAs designed based on the nucleotide sequence (SEQ ID NO: 44) of the gene of *Corynebacterium glutamicum* ATCC13032 (GenBank Database Accession No. NC_003450), which has already been disclosed. That is, PCR was carried out using a genomic DNA of *Brevibacterium lactofermentum* 2256 strain as a template and synthetic DNAs of SEQ ID NOS: 29 and 30 as primers, thereby amplified product of C-terminal region of the ach gene was obtained. On the other hand, to obtain amplified product of N-terminal region of the ach gene, PCR was carried out using a genomic DNA of *Brevibacterium lactofermentum* 2256 as a template and synthetic DNAs of SEQ ID NOS: 31 and 32 as primers. SEQ ID NO: 30 and 31 are complementary to each other. The PCR was carried out using KOD-plus-(TOYOBO) in such a way that one cycle of heat-retention at 94° C. for 2 minutes was performed and then a cycle of denaturation at 94° C. for 10 seconds, annealing at 55° C. for 30 seconds and elongation at 68° C. for 50 seconds was repeated 30 cycles for the N-terminal region and the C-terminal region. Next, to obtain a fragment of the ach gene in which an internal sequence is deleted, the above-mentioned gene products of the N-terminal and C-terminal regions of ach were mixed at an approximately equimolar concentration, and PCR was carried out using the mixture as templates and synthetic DNAs of SEQ ID NOS: 33 and 34 as primers, to thereby yield amplified product of a mutation-introduced ach gene. The PCR was carried out using KOD-plus-(TOYOBO) in such a way that one cycle of heat-retention at 94° C. for 2 minutes was performed and then a cycle of denaturation at 94° C. for 10 seconds, annealing at 55° C. for 30 seconds and elongation at 68° C. for 90 seconds was repeated 30 cycles, to thereby yield an amplified product of the mutation-introduced ach gene of interest. The PCR product thus obtained was purified by a conventional procedure and digested with XbaI, followed by insertion into XbaI site of pBS4S constructed in Example 1 (B) as described above. Competent cells of *Escherichia coli* JM109 (Takara Bio Inc.) were used for transformation with this DNA and transformed cells were applied on an LB medium containing 100 µM of IPTG, 40 µg/ml of X-Gal, and 25 µg/ml of kanamycin, followed by overnight culture. Subsequently, appeared white colonies were picked up, and single colonies were isolated, thereby transformants were obtained. Plasmids were extracted from the transformants, and a plasmid in which a PCR product of interest was inserted was named pBS4S::Δach. FIG. 8 shows the construction procedures of pBS4S::Δach.

(B) Preparation of ach-Disrupted Strain

The pBS4S::Δach obtained in the above-mentioned (A) does not include a region which enables autonomous replication in a cell of a coryneform bacterium, so when a coryneform bacterium is transformed with the plasmid, a strain in which the plasmid is integrated into a chromosome by homologous recombination appears at a very low frequency as a transformant. *Brevibacterium lactofermentum* 2256Δ(ldh) strain, 2256Δ(ldh, pta, ack) strain and 2256Δ(ldh, pta, ack, poxB) strain were transformed by using a high concentration of the plasmid pBS4S::Δach by the electric pulse method, and transformed cells were applied on a CM-Dex medium containing 25 µg/ml kanamycin, followed by culture at 31.5° C. for about 30 hours. In the strain grown on the medium, the kanamycin resistance gene and sacB gene derived from the plasmid are inserted on the genome as a result of homologous recombination between the ach gene fragment on the plasmid and the ach gene on the genome of each of *Brevibacterium lactofermentum* 2256Δ(ldh) strain, 2256Δ(ldh, pta, ack) strain and 2256Δ(ldh, pta, ack, poxB) strain.

Next, the single crossover recombinant was cultured at 31.5° C. overnight in CM-Dex liquid medium not containing kanamycin, and after suitable dilution, it was applied on 10% sucrose-containing Dex-S10 medium not containing kanamycin, followed by culture at 31.5° C. for about 30 hours, As a result, about 50 strains, which were considered to become sucrose-insensitive due to elimination of sacB gene by the second homologous recombination, were obtained.

The thus obtained strains include: a strain in which ach gene was replaced by the mutant type derived from pBS4S::Δach; and a strain in which ach gene reverted to the wild type. Whether the ach gene is the mutant type or the wild type can be confirmed easily by directly subjecting a bacterial strain obtained through culture in a Dex-S10 agar medium to PCR and detecting the ach gene. Analysis of the ach gene by using primers (SEQ ID NOS: 29 and 32) for PCR amplification should result in a DNA fragment of 2.9 kb for the wild type and a DNA fragment of 1.4 kb for the mutant type having a deleted region. As a result of the analysis of the sucrose-insensitive strain by the above-mentioned method, a strain carrying only the mutant type gene was selected and strains obtained from 2256Δ(ldh), 2256Δ(ldh, pta, ack), and 2256Δ (ldh, pta, ack, poxB) were named 2256Δ(ldh, ach), 2256Δ (ldh, pta, ack, ach), and 2256Δ(ldh, pta, ack, poxB, ach), respectively.

Example 7

Succinic Acid Production by the ach-Disrupted Strain (A) Evaluation of Culture of the ach-Deficient Strain

*Brevibacterium lactofermentum* 2256Δ(ldh) strain and 2256Δ(ldh, ach) strain were used for culture for producing succinic acid as follows. Bacterial cells of the 2256Δ(ldh) strain and 2256Δ(ldh, ach) strain obtained by culturing them on a CM-Dex plate medium were inoculated into 3 ml of a seed medium (10 g/L of glucose, 2.5 g/L of $(NH_4)_2SO_4$, 0.5 g/L of $KH_2PO_4$, 0.25 g/L of $MgSO_4 \cdot 7H_2O$, 2 g/L of urea, 0.01 g/L of $FeSO_4 \cdot 7H_2O$, 0.01 g/L of $MnSO_4 \cdot 7H_2O$, 50 μg/L of biotin, 100 μg/L of VB1.HCl, 15 mg/L of protocatechuic acid, 0.02 mg/L of $CuSO_4$, and 10 mg/L of $CaCl_2$, with pH 7.0 (KOH)). Shaking culture was performed in a test tube at 31.5° C. for about 15 hours under an aerobic condition.

After that, 3 ml of a main medium (70 g/L of glucose, 5 g/L of $(NH_4)_2SO_4$, 2 g/L of $KH_2PO_4$, 3 g/L of urea, 0.01 g/L of $FeSO_4 \cdot 7H_2O$, 0.01 g/L of $MnSO_4 \cdot 7H_2O$, 200 μg/L of biotin, 200 μg/L of VB1.HCl, 40 g/L of MOPS, 50 g/L of $MgCO_3$, with pH 6.8 (NaOH)) was added into the tube. For preventing aeration, the succinic acid production culture was carried out while the tube was sealed hermetically with a silicon cap. The culture was performed by shaking at 31.5° C. for about 24 hours and terminated before sugar in the medium was exhausted.

After completion of the culture, the accumulation amounts of succinic acid and by-product acetic acid in the medium were analyzed by liquid chromatography after the culture liquid had been suitably diluted. A column obtained by connecting two pieces of Shim-pack SCR-102H (Shimadzu) in series was used, and the sample was eluted at 40° C. by using 5 mM p-toluene sulfonic acid. The eluent was neutralized by using 20 mM Bis-Tris aqueous solution containing 5 mM p-toluene sulfonic acid and 100 μM of EDTA. Succinic acid and acetic acid were each measured by determining the electric conductivity by means of CDD-10AD (Shimadzu). The obtained results are shown in Table 1.

It was found that yield of the 2256Δ(ldh, ach) strain improved by about 6% as compared to the 2256Δ(ldh) strain as a parent strain.

TABLE 1

Production of succinic acid and acetic acid in ACH-disrupted strain

| Strains | OD620 nm(×51) | Consumed sugar (g/L) | Yield of succinic acid (%) | Acetic acid (/succinic acid, %) |
|---|---|---|---|---|
| 2256Δldh | 0.366 | 35.8 | 57.1 | 9.2 |
| 2256Δ(ldh, ach) | 0.353 | 31.4 | 63.1 | 17.4 |

(B) Evaluation of Culture of the ach, pta and ack-Disrupted Strain

*Brevibacterium lactofermentum* 2256Δ(ldh) strain and 2256Δ(ldh, ach, pta, ack) strain were used for culture for producing succinic acid as follows. The bacterial cells of the 2256Δ(ldh) strain and 2256Δ(ldh, ach, pta, ack) strain obtained by culturing them on a CM-Dex plate medium were inoculated into 3 ml of the above-mentioned seed medium. Shaking culture was performed in a test tube at 31.5° C. for about 15 hours under an aerobic condition.

After that, 3 ml of the above-mentioned main medium was added into the test tube. For preventing aeration, the succinic acid production culture was carried out while the tube was sealed hermetically with a silicon cap. The culture was performed by shaking at 31.5° C. for about 24 hours and terminated before sugar in the medium was exhausted.

After completion of the culture, the accumulation amounts of succinic acid and by-product acetic acid in the culture medium were analyzed by liquid chromatography after the culture medium had been suitably diluted. A column obtained by connecting two pieces of Shim-pack SCR-102H (Shimadzu) in series was used, and the sample was eluted at 40° C. by using 5 mM of p-toluene sulfonic acid. The eluent was neutralized by using 20 mM of Bis-Tris aqueous solution containing 5 mM of p-toluene sulfonic acid and 100 μM of EDTA. The succinic acid and by-product acetic acid were each measured by determining the electric conductivity by means of CDD-10AD (Shimadzu). The obtained results are shown in Table 2.

In the case of 2256Δ(ldh, ach, pta, ack) strain, the succinic acid production level was equal to the parent strain 2256Δ (ldh), but the level of acetic acid with respect to succinic acid was reduced to about one third of 2256Δ(ldh, ach) strain and to about half of 2256Δ(ldh) strain, which revealed that production of acetic acid as a by-product drastically decreased. This result and the above-mentioned result described in (A) indicated that eliminating or decreasing either PTA-ACK or ACH activity is ineffective for reducing acetic acid, but acetic acid is drastically reduced by eliminating or decreasing all these activities. Meanwhile, it is easily assumed that eliminating or decreasing the activity of PTA or ACK together with ACH activity is effective for reducing acetic acid. As for succinic acid production, eliminating or decreasing only ACH activity was found to be effective.

TABLE 2

Production of succinic acid and acetic acid in the strain in which ACH, PTA and ACK have been disrupted in combination

| Strains | OD620 (×51) | Consumed sugar (g/L) | Yield of succinic acid (%) | Acetic acid (/succinic acid %) |
|---|---|---|---|---|
| 2256Δldh | 0.342 | 31.8 | 57.3 | 11.9 |
| 2256Δ(ldh, ach) | 0.364 | 33.0 | 63.6 | 17.3 |
| 2256Δ(ldh, ach, pta, ack) | 0.347 | 39.0 | 58.3 | 6.1 |

(C) Evaluation of Culture of the ach, pta, ack and poxB-Disrupted Strain

*Brevibacterium lactofermentum* 2256Δ(ldh) strain, 2256Δ (ldh, pta-ack, ach) strain and 2256Δ(ldh, pta-ack, poxB, ach) strain were used for culture for producing succinic acid as follows. The bacterial cells of the 2256Δ(ldh), 2256Δ(ldh, pta-ack, ach) strain and 2256Δ(ldh, pta-ack, poxB, ach) strain obtained by culturing them on a CM-Dex plate medium were inoculated into 3 ml of the above-mentioned seed medium, and shaking culture in a test tube was performed at 31.5° C. for about 15 hours under an aerobic condition.

After that, 3 ml of the above-mentioned main medium was added into the tube. For preventing aeration, the succinic acid production culture was carried out while the tube was sealed hermetically with a silicon cap. The culture was performed by shaking at 31.5° C. for about 24 hours and terminated before sugar in the medium was exhausted. After completion of the culture, the accumulation amounts of succinic acid and by-product acetic acid in the medium were analyzed by liquid chromatography after the medium had been suitably diluted. A column obtained by connecting two pieces of Shim-pack SCR-102H (Shimadzu) in series, and the sample was eluted at 40° C. by using 5 mM of p-toluene sulfonic acid. The eluent was neutralized by using 20 mM of Bis-Tris aqueous solution containing 5 mM of p-toluene sulfonic acid and 100 µM of EDTA. The succinic acid and by-product acetic acid were each measured by determining the electric conductivity by means of CDD-10AD (Shimadzu), The obtained results are shown in Table 3.

In the case of 2256Δ(ldh, pta, ack, ach, poxB) strain prepared by further disrupting poxB in the 2256Δ(ldh, pta, ack, ach) strain, acetic acid was further decreased by about 40% as compared to the parent 2256Δ(ldh, pta, ack, ach) strain. The result revealed that eliminating or decreasing ach activity together with activities of all or any of pta, ack and poxB is effective for reducing acetic acid.

TABLE 3

Production of succinic acid and acetic acid in the strain in which ACH, PTA, ACK and POXB have been decreased in combination

| Strains | OD620 (×51) | Consumed sugar (g/L) | Yield of succinic acid (%) | Acetic acid (/succinic acid %) |
|---|---|---|---|---|
| 2256Δldh | 0.342 | 31.8 | 57.3 | 11.9 |
| 2256Δ(ldh, pta, ack, ach) | 0.347 | 39 | 58.4 | 6.1 |
| 2256Δ(ldh, pta, ack, poxB, ach) | 0.372 | 39.8 | 56.1 | 3.6 |

INDUSTRIAL APPLICABILITY

Use of the bacterium of the present invention enables efficient production of succinic acid. Succinic acid is useful as a raw material for a biodegradable polymer and the like.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2004-150658, is incorporated by reference herein in its entirety.

The invention claimed is:

1. A method for producing succinic acid, comprising allowing a coryneform bacterium, or immobilized bacterial cells or disrupted bacterial cells thereof, to act on a carbohydrate fermentable by said coryneform bacterium in a reaction liquid containing a carbonate ion, a bicarbonate ion, or carbon dioxide to generate and accumulate succinic acid in the reaction liquid, and collecting succinic acid from the reaction liquid, wherein said coryneform bacterium is *Corynebacterium glutamicum* or *Brevibacterium flavum* and has been modified so that an activity of acetyl-CoA hydrolase is decreased by making an acetyl-CoA hydrolase gene on the chromosome of said coryneform bacterium deficient, or by modification of an expression regulatory sequence of an acetyl-CoA hydrolase gene on the chromosome of said coryneform bacterium, wherein the acetyl-CoA hydrolase gene is a DNA as described in the following (a) or (b):
   (a) a DNA comprising nucleotides 1037-2542 in SEQ ID NO: 44; or
   (b) a DNA that hybridizes with nucleotides 1037-2542 in SEQ ID NO: 44 under stringent conditions comprising washing at a salt concentration corresponding to 0.1× SSC, 0.1% SDS at 60° C., and encodes a protein having an acetyl-CoA hydrolase activity.

2. The method according to claim 1, wherein the coryneform bacterium is, or immobilized bacterial cells or disrupted bacterial cells thereof are, allowed to act on the carbohydrate under anaerobic conditions.

3. A method for producing a succinic acid-containing polymer, comprising producing succinic acid by the method according to claim 1 and polymerizing the obtained succinic acid.

4. The method according to claim 1, wherein the acetyl-CoA hydrolase is a protein as described in the following (A) or (B):
   (A) a protein having an amino acid sequence of SEQ ID NO: 45; or
   (B) a protein having an amino acid sequence of SEQ ID NO: 45 including substitution, deletion, insertion, or addition of one to 20 amino acids, and having an acetyl Co-A hydrolase activity.

5. The method according to claim 1, wherein the acetyl-CoA hydrolase activity has been decreased by disruption of an acetyl-CoA hydrolase gene on a chromosome.

6. The method according to claim 1, wherein said bacterium has been further modified so that an activity of lactate dehydrogenase is decreased by making a lactate dehydrogenase gene on the chromosome of said coryneform bacterium deficient, or by modification of an expression regulatory sequence of a lactate dehydrogenase gene on the chromosome of said coryneform bacterium, wherein the lactate dehydrogenase is a protein as described in the following (C) or (D):
   (C) a protein having an amino acid sequence of SEQ ID NO: 38; or
   (D) a protein having an amino acid sequence of SEQ ID NO: 38 including substitution, deletion, insertion, or addition of one to 20 amino acids, and having a lactate dehydrogenase activity.

7. The method according to claim 6, wherein said bacterium has been further modified so that activities of one or both of phosphotransacetylase and acetate kinase are decreased by making a phosphotransacetylase gene and/or an acetate kinase gene on the chromosome of said coryneform bacterium deficient, or by modification of an expression regulatory sequence of a phosphotransacetylase gene and/or an acetate kinase gene on the chromosome of said coryneform bacterium, wherein the phosphotransacetylase is a protein as described in the following (E) or (F):
   (E) a protein having an amino acid sequence of SEQ ID NO: 40; or
   (F) a protein having an amino acid sequence of SEQ ID NO: 40 including substitution, deletion, insertion, or addition of one to 20 amino acids, and having phosphotransacetylase activity,
   and wherein the acetate kinase is a protein as described in the following (G) or (H):
   (G) a protein having an amino acid sequence of SEQ ID NO: 41; or
   (H) a protein having an amino acid sequence of SEQ ID NO: 41 including substitution, deletion, insertion, or addition of one to 20 amino acids, and having an acetate kinase activity.

* * * * *